(12) United States Patent
Barbion et al.

(10) Patent No.: US 11,530,227 B2
(45) Date of Patent: Dec. 20, 2022

(54) HETEROCYCLIC COMPOUNDS AND THEIR USE IN PREVENTING OR TREATING BACTERIAL INFECTIONS

(71) Applicant: MUTABILIS, Romainville (FR)

(72) Inventors: Julien Barbion, Sannois (FR); Audrey Caravano, Enghien les Bains (FR); Sophie Chasset, Nandy (FR); Francis Chevreuil, Chantilly (FR); Nicolas Lecointe, Paris (FR); Frédéric Le Strat, Combs la Ville (FR); Chrystelle Oliveira, Saint Prix (FR); Christophe Simon, Chevilly Larue (FR)

(73) Assignee: MUTABILIS, Romainville (FR)

( * ) Notice: Subject to any disclaimer, the term of this patent is extended or adjusted under 35 U.S.C. 154(b) by 0 days.

(21) Appl. No.: 17/263,664

(22) PCT Filed: Jul. 30, 2019

(86) PCT No.: PCT/EP2019/070444
§ 371 (c)(1),
(2) Date: Jan. 27, 2021

(87) PCT Pub. No.: WO2020/025587
PCT Pub. Date: Feb. 6, 2020

(65) Prior Publication Data
US 2021/0277019 A1 Sep. 9, 2021

(30) Foreign Application Priority Data

Jul. 30, 2018 (EP) ..................................... 18306028

(51) Int. Cl.
*C07D 495/18* (2006.01)
*C07D 471/18* (2006.01)
*C07D 471/22* (2006.01)
*C07D 495/22* (2006.01)
*A61P 31/04* (2006.01)

(52) U.S. Cl.
CPC ............ *C07D 495/18* (2013.01); *A61P 31/04* (2018.01); *C07D 471/18* (2013.01); *C07D 471/22* (2013.01); *C07D 495/22* (2013.01)

(58) Field of Classification Search
CPC .. C07D 471/18; C07D 471/22; C07D 495/18; C07D 495/22
See application file for complete search history.

(56) References Cited

U.S. PATENT DOCUMENTS

2005/0245505 A1    11/2005   Aszodi et al.

FOREIGN PATENT DOCUMENTS

| WO | 2004052891 A1 | 6/2004 |
| WO | 2014141132 A1 | 9/2014 |
| WO | 2017109025 A1 | 6/2017 |

*Primary Examiner* — Susanna Moore
(74) *Attorney, Agent, or Firm* — Thompson Coburn LLP; Steven M. Ritchey

(57) ABSTRACT

The present invention relates to compounds of formula (I) and their use for treating or preventing a bacterial infection or as an antibacterial agent and/or as a β-lactamase inhibitor.

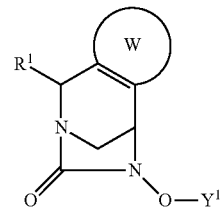

22 Claims, No Drawings

HETEROCYCLIC COMPOUNDS AND THEIR USE IN PREVENTING OR TREATING BACTERIAL INFECTIONS

CROSS-REFERENCE TO RELATED APPLICATIONS

This application is a U.S. National Phase application of PCT/EP2019/070444 filed on Jul. 30, 2019, claiming the benefit of European Application No. 18306028.4, filed on Jul. 30, 2018, both of which are incorporated herein by reference in their entireties.

The present invention relates to heterocyclic compounds, their process of preparation, pharmaceutical compositions comprising these compounds and use thereof, optionally in combination with other antibacterial agents and/or beta-lactam compounds, for the prevention or treatment of bacterial infections. The present invention also relates to the use of these compounds as β-lactamase inhibitors and/or as antibacterial agents.

It has been described that there is a continuous evolution of antibacterial resistance which could lead to bacterial strains against which known antibacterial compounds are inefficient.

There is thus a need to provide effective compounds and composition that can overcome bacterial antibiotic resistance.

The objective of the present invention is to provide heterocyclic compounds that can be used as antibacterial agents and/or beta-lactamase inhibitors.

An objective of the present invention is also to provide heterocyclic compounds that can be used for the prevention or for the treatment of bacterial infections.

Another objective of the present invention is to provide heterocyclic compounds that can overcome bacterial antibiotic resistance.

An objective of the invention is also to provide pharmaceutical compositions comprising such heterocyclic compounds, optionally in combination with one or more other antibacterial agent, for the prevention or for the treatment of bacterial infections and which can overcome bacterial antibiotic resistance.

Other objectives will appear throughout the description of the invention.

The present invention thus provides a compound of formula (I)

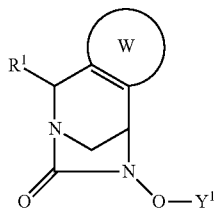

(I)

wherein

W represents a 8- to 10-membered aromatic or partially unsaturated bicycle optionally comprising one or more heteroatom chosen independently in the group consisting of O, N, N($T^2$), S and/or optionally substituted by one or more $T^1$;

$R^1$ is chosen in the group consisting of H, $(CH_2)_m CN$, $(CH_2)_m C(=O)NR^2R^3$, $(CH_2)_m C(=O)NR^4NR^2R^3$, $(CH_2)_m C(=O)NR^2OR^3$, $(CH_2)_p OR^2$, $(CH_2)_p NR^2R^3$, $(CH_2)_p NR^4 C(=NR^4)N(R^4)_2$, $(CH_2)_m C(=NOZ^4)NZ^1Z^2$, $(CH_2)_p$-(5 to 6-membered heteroaryl comprising 1 or 4 heteroatoms independently chosen in the group consisting of N, O or S);

m is an integer from 0 to 6;

p is an integer from 1 to 6;

$R^2$ and $R^3$, identical or different, are chosen in the group consisting of H, linear or branched (C1-C6)alkyl, (C3-C11)cycloalkyl, (C6-C10)aryl, 4- to 6-membered heterocyclyl comprising 1 to 2 heteroatom chosen independently in the group consisting of N, O or S, 5- to 10-membered heteroaryl comprising 1 to 4 heteroatom chosen independently in the group consisting of N, O or S, C(=O)(linear or branched C1-C6)alkyl, C(=O)(4 to 6-membered heterocyclyl comprising 1 to 2 heteroatom chosen independently in the group consisting of N, O or S) or form together with the nitrogen atom to which they are linked a 4- to 6-membered heterocyclyl comprising 1 to 2 heteroatom chosen independently in the group consisting of N, O or S, wherein the alkyl, cycloalkyl, aryl, heterocyclyl and heteroaryl are optionally substituted by one or more $R^5$;

$R^4$, each identical or different, is independently chosen in the group consisting of H, linear or branched (C1-C6)alkyl, wherein the alkyl is optionally substituted by one or more $R^5$;

$R^5$, each identical or different, is chosen in the group consisting of OH, O-(linear or branched-C1-C6)alkyl, $NH_2$, NH(linear or branched C1-C6)alkyl, N[(linear or branched C1-C6)Alkyl]$_2$, C(=O)$NH_2$, C(=O)NH(linear or branched C1-C6)alkyl, C(=O)N[linear or branched (C1-C6)alkyl]$_2$;

$Y^1$ is chosen in the group consisting of $SO_3H$, CHFC(=O)$Y^2$, $CF_2C(=O)Y^2$, $SO_3(C1-C6)alkyl-C(=O)O(C1-C6)alkyl$;

$Y^2$ is chosen in the group consisting of OH, O(C1-C6)alkyl linear or branched, O(C3-C11)cycloalkyl, O-(4 to 6-membered heterocyclyl comprising 1 or 2 heteroatom chosen independently in the group consisting of N, O and S); $NY^3Y^4$, wherein the alkyl, cycloalkyl and heterocyclyl are optionally substituted by one or more $Y^5$;

$Y^3$ and $Y^4$, each identical or different, is chosen in the group consisting of linear or branched (C1-C6)alkyl, linear or branched O(C1-C6)alkyl, (C3-C11)cycloalkyl, 4 to 6-membered heterocyclyl comprising 1 or 2 heteroatoms chosen independently in the group consisting of N, O or S, or form together with the nitrogen atom to which they are linked a 4- to 6-membered heterocyclyl comprising 1 or 2 heteroatoms chosen independently in the group consisting of N, O or S; wherein the alkyl, cycloalkyl and heterocyclyl is optionally substituted by one or more $Y^5$ $Y^5$, each identical or different, is chosen in the group consisting of linear or branched (C1-C6)alkyl, (C3-C6)cycloalkyl, linear or branched O(C1-C6)alkyl, linear or branched O(C1-C6)alkyl-O(C1-C6)alkyl, linear or branched (C1-C6)alkyl-O(C1-C6)alkyl; and O(C3-C6)cycloalkyl;

$T^1$ is chosen in the group consisting of halogen, $(CH_2)_m$—CN, $(CH_2)_m$—$OX^1$, $(CH_2)_m$—$C(=O)NX^1X^2$, $(CH_2)_m$—C(=O)$NX^1OX^2$, $(CH_2)_m$—$C(=O)NX^1NX^2X^3$, $(CH_2)_m$—C(=NOX$^1$)$X^2$, $(CH_2)_m$—$C(=NX^1)NX^2X^3$, $(CH_2)_m$—$NX^1X^2$, $(CH_2)_m$—$NX^1C(=O)X^2$, $(CH_2)_m$—$NX^1C(=O)NX^2X^3$, $(CH_2)_m$—$NX^1S(=O)_2NX^2X^3$, $(CH_2)_m$—$NX^1S(=O)_2X^2$, $(CH_2)_m$—$NX^1C(=NX^2)NX^2X^3$, $(CH_2)_m$—$NX^1C(=NX^2)X^2$, $(CH_2)_m$—$S(=O)_2NX^1X^2$, linear or branched (C1-C6)alkyl, (C3-C6)cycloalkyl, $(CH_2)_m$-aryl, $(CH_2)_m$-(5- to 6-membered heteroaryl comprising from 1 to 4 heteroatom chosen independently in the group consisting of N, O or S), $(CH_2)_m$-(4- to 6-membered heterocyclyl comprising from 1 to 2 heteroatom chosen independently in the group consisting of N, O or S), wherein the alkyl, cycloalkyl, aryl, heteroaryl and heterocyclyl are optionally substituted by one or more $X^4$;

$T^2$ is chosen in the group consisting of H, $(CH_2)_n$—CN, $(CH_2)_n$—$OX^1$, $(CH_2)_m$—C(=O)$X^1$, $(CH_2)_m$—C(=O)$NX^1X^2$, $(CH_2)_m$—C(=O)$NX^1OX^2$, $(CH_2)_m$—C(=O)$NX^1NX^2X^3$, $(CH_2)_m$—C(=$NOX^1$)$X^2$, $(CH_2)_m$—C(=$NX^1$)$NX^2X^3$, $(CH_2)_n$—$NX^1X^2$, $(CH_2)_n$—$NX^1$C(=O)$X^2$, $(CH_2)_n$—$NX^1$C(=O)$NX^2X^3$, $(CH_2)_n$—$NX^1$S(=O)$_2$$NX^2X^3$, $(CH_2)_n$—$NX^1$S(=O)$_2$$X^2$, $(CH_2)_n$—$NX^1$C(=$NX^2$)$NHX^3$, $(CH_2)_n$—$NX^1$C(=$NX^2$)$X^2$, $(CH_2)_m$—S(=O)$_2$$NX^2X^3$, linear or branched (C1-C6)alkyl, (C3-C6)cycloalkyl, $(CH_2)_m$-aryl, $(CH_2)_m$-(5- to 6-membered heteroaryl comprising from 1 to 4 heteroatom chosen independently in the group consisting of N, O or S), $(CH_2)_m$-(4- to 6-membered heterocyclyl comprising from 1 to 2 heteroatom chosen independently in the group consisting of N, O or S) wherein the alkyl, cycloalkyl, aryl, heteroaryl and heterocyclyl are optionally substituted by one or more $X^4$;

$X^1$, $X^2$ and $X^3$, each identical or different, are chosen in the group consisting of H, linear or branched (C1-C6)alkyl, (C3-C6)cycloalkyl, (C2-C6)alkyl-$NZ^1Z^2$, (C2-C6)alkyl-NHC(=$NZ^1$)$NHZ^2$, (C2-C6)alkyl-NHC(=$NZ^1$)$Z^2$, (C2-C6)alkyl-$NZ^1$C(=O)$Z^2$, (C2-C6)alkyl-$OZ^1$, (C1-C6)alkyl-C(=$NZ^1$)$NHZ^2$, (C1-C6)alkyl-$CONZ^1Z^2$, (C1-C6)alkyl-$COOZ^1$, $(CH_2)_m$-aryl, $(CH_2)_m$-(5- to 6-membered heteroaryl comprising from 1 to 4 heteroatom chosen independently in the group consisting of N, O and S), $(CH_2)_m$-(4- to 6-membered heterocyclyl comprising from 1 to 2 heteroatom chosen independently in the group consisting of N, O and S), or form together with the nitrogen atom to which they are linked a 4- to 6-membered heterocyclyl comprising 1 or 2 heteroatom chosen independently in the group consisting of N, O or S, wherein the alkyl, cycloalkyl, aryl, heteroaryl and heterocyclyl are optionally substituted by one or more $Z^3$;

$X^4$, each identical or different, is chosen in the group consisting of H, Halogen, linear or branched (C1-C6)alkyl, (C3-C6)cycloalkyl, $(CH_2)_m$—$NZ^1Z^2$, $(CH_2)_m$—NHC(=$NZ^1$)$NHZ^2$, $(CH_2)_m$—NHC(=$NZ^1$)H, $(CH_2)_m$—$NZ^1$C(=O)$Z^2$, $(CH_2)_m$—$OZ^1$, $(CH_2)_m$—C(=$NZ^1$)$NHZ^2$, $(CH_2)_m$—$CONZ^1Z^2$, $(CH_2)_m$—$COOZ^1$, $(CH_2)_m$-aryl, $(CH_2)_m$-(5- to 6-membered heteroaryl comprising from 1 to 4 heteroatom chosen independently in the group consisting of N, O and S), $(CH_2)_m$-(4- to 6-membered heterocyclyl comprising from 1 to 2 heteroatom chosen independently in the group consisting of N, O and S), wherein the alkyl, cycloalkyl, aryl, heteroaryl and heterocyclyl are optionally substituted by one or more $Z^3$;

$Z^1$ and $Z^2$, identical or different, are chosen in the group consisting of H, linear or branched (C1-C6)alkyl, (C3-C6) cycloalkyl, (C2-C6)alkyl-N($Z^4$)$_2$, (C2-C6)alkyl-NHC(=$NZ^4$)$NHZ^5$, (C2-C6)alkyl-NHC(=$NZ^4$)$Z^5$, (C2-C6)alkyl-$NZ^4$C(=O)$Z^4$, (C2-C6)alkyl-$OZ^4$, (C1-C6)alkyl-C(=NH)$NHZ^4$, (C1-C6)alkyl-CON($Z^4$)$_2$, (C1-C6)alkyl-$COOZ^4$;

$Z^3$, each identical or different, is chosen in the group consisting of H, halogen, linear or branched (C1-C6)alkyl, (C3-C6)cycloalkyl, $(CH_2)_m$—N($Z^4$)$_2$, $(CH_2)_m$—NHC(=$NZ^4$)$NHZ^5$, $(CH_2)_m$—NHC(=$NZ^4$)$Z^5$, $(CH_2)_m$—$NZ^4$C(=O)$Z^4$, $(CH_2)_m$—$OZ^4$, $(CH_2)_m$—C(=$NZ^4$)$NHZ^5$, $(CH_2)_m$—CON($Z^4$)$_2$, $(CH_2)_m$—$COOZ^4$;

$Z^4$, each identical or different, is chosen in the group consisting of H, linear or branched (C1-C6)alkyl, (C3-C6) cycloalkyl, n is an integer from 2 to 6;

any sulphur atom present within a heterocycle can be oxidized to form a S=O group or a S(O)$_2$ group;

any nitrogen atom present within a heterocycle or present within group wherein it is trisubstituted thus forming a tertiary amino group, can be further quaternized by a methyl group;

and a racemate, an enantiomer, a diastereoisomer, a geometric isomer or a pharmaceutically acceptable salt thereof.

Preferably:

$R^1$ is chosen in the group consisting of H, $(CH_2)_m$CN, $(CH_2)_m$C(=O)$NR^2R^3$, $(CH_2)_m$C(=O)$NR^4NR^2R^3$, $(CH_2)_m$C(=O)$NR^2OR^3$, $(CH_2)_p$$OR^2$, $(CH_2)_p$$NR^2R^3$, $(CH_2)_p$$NR^4$C(=$NR^4$)N($R^4$)$_2$, $(CH_2)_p$-(5- to 6-membered heteroaryl comprising 1 or 4 heteroatoms independently chosen in the group consisting of N, O or S) and/or $Y^1$ is chosen in the group consisting of $SO_3H$, CHFC(=O)$Y^2$, $CF_2$C(=O)$Y^2$.

The present invention also relates to compounds of formula (I*)

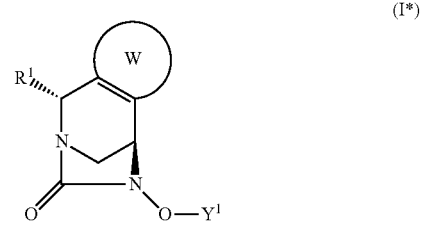

wherein $R^1$, W and $Y^1$ are as defined for formula (I).

Preferably, the compound of the invention are of formula (IA) or (IA*)

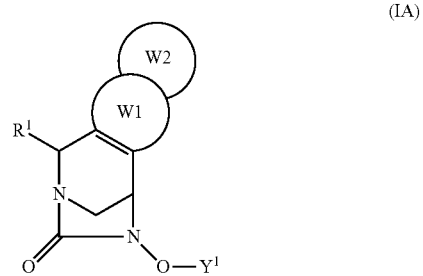

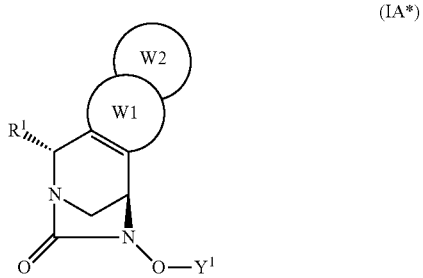

wherein

W1 is a 5- to 6-membered ring, aromatic or partially unsaturated, optionally substituted by one or more $T^1$ and comprising optionally one or more heteroatom independently selected from the group consisting of O, N, N($T^2$), S;

W2 is a 5- to 6-membered ring, aromatic or partially unsaturated, optionally substituted by one or more $T^1$ and comprising optionally one or more heteroatom independently selected from the group consisting of O, N, N($T^2$), S, $R^1$, $Y^1$, $T^1$ and $T^2$ being as defined above.

In one embodiment, in the compounds of formula (IA) or (IA*):
W1 represents a 5-membered ring, aromatic or partially unsaturated, optionally substituted by one or more $T^1$ and comprising 1 or 2 heteroatom independently selected from the group consisting of O, N, $N(T^2)$, S and
W2 represents a 5- to 6-membered ring, aromatic or partially unsaturated, optionally substituted by one or more $T^1$ and comprising optionally one or more heteroatom independently selected from the group consisting of O, N, $N(T^2)$, S
$T^1$ and $T^2$ being as defined above.

In another embodiment, in the compounds of formula (IA) or (IA*):
W1 represents a 6-membered ring, aromatic or partially unsaturated, optionally substituted by one or more $T^1$ and comprising optionally 1 or 2 heteroatom independently selected from the group consisting of O, N, $N(T^2)$, S
W2 represents a 5- to 6-membered ring, aromatic or partially unsaturated, optionally substituted by one or more $T^1$ and comprising optionally one or more heteroatom independently selected from the group consisting of O, N, $N(T^2)$, S
$T^1$ and $T^2$ being as defined above.

In one preferred embodiment, in compounds of formula (IA) or (IA*):
W1 represents a thiazole, thiophene, pyrrole, pyrrole for which one N atom is substituted by $T^2$ or imidazole, optionally substituted by one or more $T^1$;
W2 represents a 5- to 6-membered ring, aromatic or partially unsaturated, optionally substituted by one or more $T^1$ and comprising optionally one or more heteroatom independently selected from the group consisting of O, N, $N(T^2)$, S
$T^1$ and $T^2$ being as defined above.

In one preferred embodiment, in compounds of formula (IA) or (IA*):
W1 represents a phenyl, pyridine, pyrazine or thiazine, optionally substituted by one or more $T^1$;
W2 represents a 5- to 6-membered ring, aromatic or partially unsaturated, optionally substituted by one or more $T^1$ and comprising optionally one or more heteroatom independently selected from the group consisting of O, N, $N(T^2)$, S
$T^1$ and $T^2$ being as defined above.

In one preferred embodiment, in compounds of formula (IA) or (IA*):
W1 represents a thiazole, thiophene, pyrrole, pyrrole for which one N atom is substituted by $T^2$ or imidazole, optionally substituted by one $T^1$
W2 represents a imidazole, imidazole for which one N atom is substituted by $T^2$, triazole, triazole for which one N atom is substituted by $T^2$, pyrrole, pyrrole for which one N atom is substituted by $T^2$, pyrazole, Pyrazole for which one N atom is substituted by $T^2$, dihydropyrrole, dihydropyrrole for which one N atom is substituted by $T^2$, thiazole, optionally substituted by one or more $T^1$
$T^1$ and $T^2$ being as defined above.

In one preferred embodiment, in compounds of formula (IA) or (IA*):
W1 represents a thiazole, thiophene, pyrrole, pyrrole for which one N atom is substituted by $T^2$ or imidazole, optionally substituted by one $T^1$
W2 represents a phenyl, pyridine, pyridazine, pyrimidine, pyrazine or tetrahydropyridine for which one N atom is substituted by $T^2$, optionally substituted by one $T^1$
$T^1$ and $T^2$ being as defined above.

In one preferred embodiment, in compounds of formula (IA) or (IA*):
W1 represents a phenyl, pyridine, pyrazine or thiazine, optionally substituted by one or more $T^1$
W2 represents a imidazole, imidazole for which one N atom is substituted by $T^2$, triazole, triazole for which one N atom is substituted by $T^2$, pyrrole, pyrrole for which one N atom is substituted by $T^2$, pyrazole, Pyrazole for which one N atom is substituted by $T^2$, dihydropyrrole, dihydropyrrole for which one N atom is substituted by $T^2$, thiazole, optionally substituted by one or more $T^1$
$T^1$ and $T^2$ being as defined above.

In one preferred embodiment, in compounds of formula (IA) or (IA*):
W1 represents a phenyl, pyridine, pyrazine or thiazine, optionally substituted by one or more $T^1$
W2 represents a phenyl, pyridine, pyridazine, pyrimidine, pyrazine or tetrahydropyridine for which one N atom is substituted by $T^2$, optionally substituted by one $T^1$
$T^1$ and $T^2$ being as defined above.

W1 is preferably chosen in the group consisting of:
  a phenyl group optionally substituted by one or more $T^1$;
  5 to 6-membered heterocycle aromatic or partially unsaturated, comprising from 1 to 2 heteroatom independently chosen in the group consisting of N, $N(T^2)$, S or O, preferably N, $N(T^2)$, S, optionally substituted by one or more $T^1$;
W2 is preferably chosen in the group consisting of:
  a phenyl group optionally substituted by one or more $T^1$;
  5 to 6-membered heterocycle aromatic or partially unsaturated, optionally substituted by one or more $T^1$, comprising from 1 to 3 heteroatom independently chosen in the group consisting of N, $N(T^2)$, S or O, preferably N, $N(T^2)$, S, optionally substituted by one or more $T^1$
$T^1$ and $T^2$ being as defined above.

In another embodiment, in the compounds of formula (IA) or (IA*)
W1 is preferably chosen in the group consisting of:
  5 to 6-membered heterocycle aromatic or partially unsaturated, optionally substituted by one or more $T^1$, comprising at least one S atom and optionally comprising a further heteroatom chosen in the group consisting of O, N, $N(T^2)$, S, preferably $N(T^2)$;
  5 to 6-membered heterocycle aromatic or partially unsaturated, optionally substituted by one or more $T^1$, comprising one N or $N(T^2)$ group;
  a phenyl group optionally substituted by one or more $T^1$;
W2 is preferably chosen in the group consisting of:
  a phenyl group optionally substituted by one or more $T^1$;
  5 to 6-membered heterocycle aromatic or partially unsaturated, optionally substituted by one or more $T^1$, comprising at least one N atom or N(T2) group and optionally comprising at least a further heteroatom chosen in the group consisting of O, N, $N(T^2)$, S, preferably N, $N(T^2)$ or S;
$T^1$ and $T^2$ being as defined above.

In one preferred embodiment, in compounds of formula (IA) or (IA*):
W1 represents a 5-membered ring, aromatic or partially unsaturated, optionally substituted by one or more $T^1$ and comprising 1 or 2 heteroatom independently selected from the group consisting of O, N, $N(T^2)$, S and
W2 represents a 5- to 6-membered ring, aromatic or partially unsaturated, optionally substituted by one or more $T^1$ and comprising optionally one or more heteroatom independently selected from the group consisting of O, N, $N(T^2)$, S
$T^1$ and $T^2$ being as defined above.

Preferably, the compounds of formula (I) according to the invention chosen among compound of formula

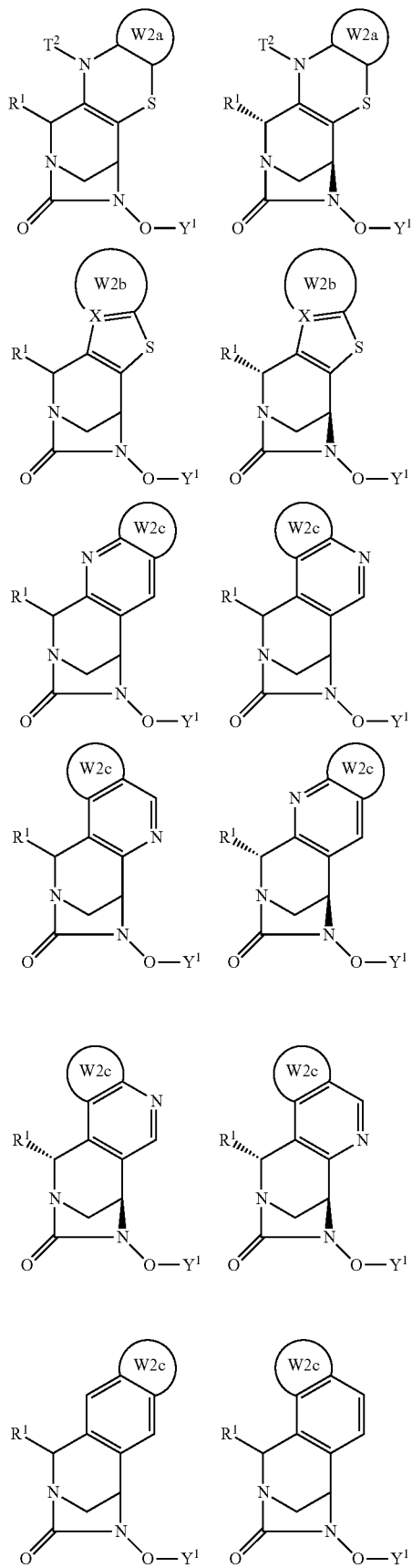
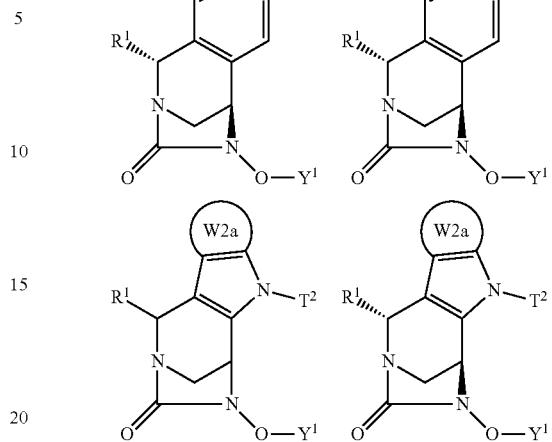

wherein

W2a, W2b, W2c are independently chosen among 5- to 6-membered ring, aromatic or partially unsaturated, optionally substituted by one or more $T^1$ and comprising optionally one or more heteroatom independently selected from the group consisting of O, N, N($T^2$), S, X is chosen from C or N;

$R^1$, $Y^1$, $T^1$ and $T^2$ being as defined above.

Preferably, the compounds of formula (I) according to the invention chosen among compound of formula

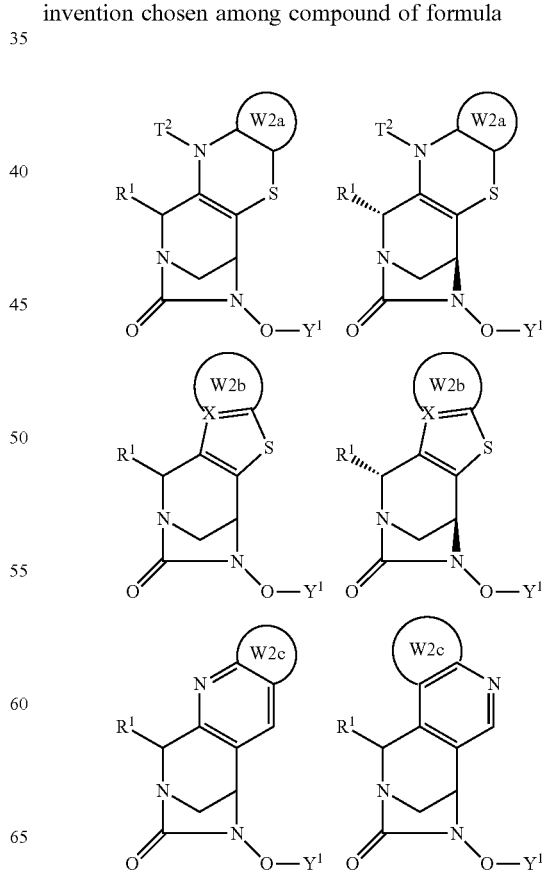

-continued

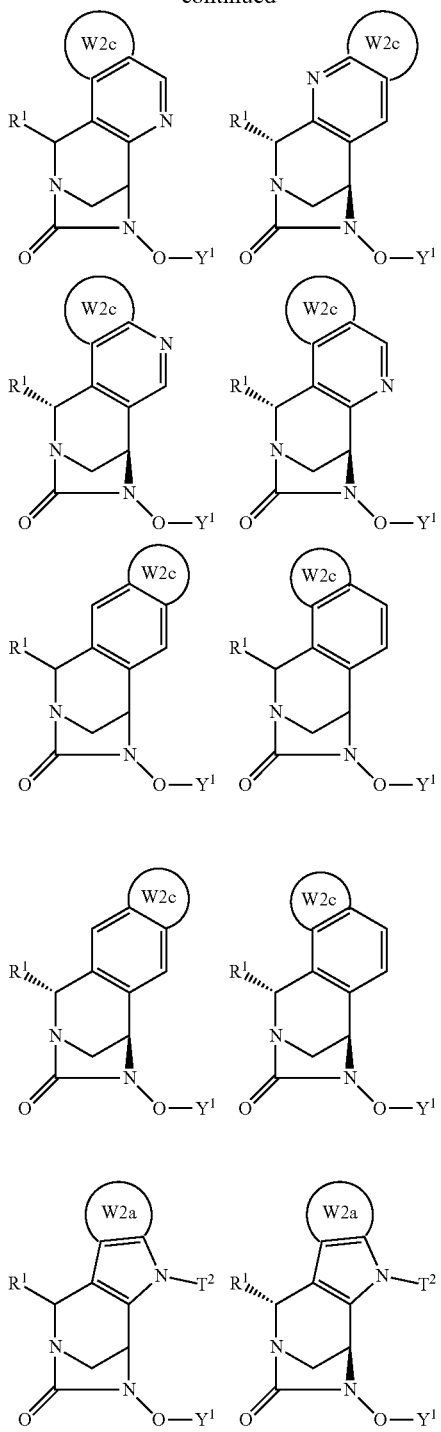

wherein

W2a is chosen in the group consisting of phenyl or pyridinyl

X is chosen from C or N;

W2b and W2c are chosen in the group consisting of phenyl, 5 to 6-membered heterocycle, aromatic or partially unsaturated, optionally substituted by one or more $T^1$, comprising 1 to 3 heteroatom independently chosen in the group consisting of N(T), N or S;

$R^1$, $Y^1$, $T^1$ and $T^2$ being as defined above.

Preferably, the compounds of the invention are of formula

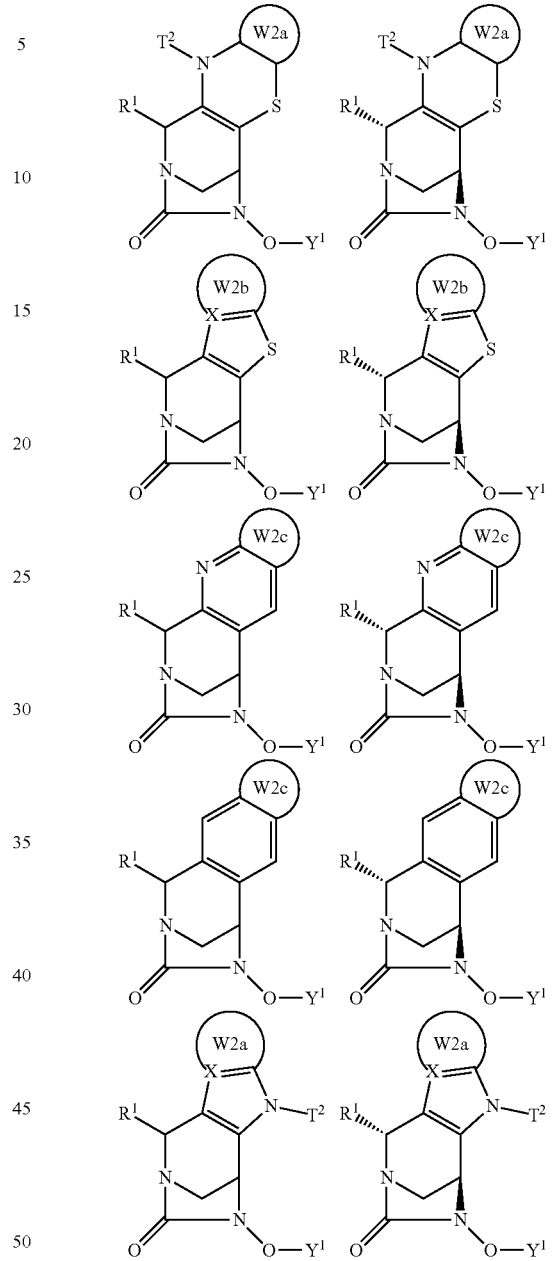

Wherein $T^2$, $Y^1$ and $R^1$ are as defined above;

W2a is chosen among phenyl, pyridinyl,

X is C and W2b is tetrahydropyridine wherein the N atom is substituted by $T^2$, dihydropyrrole wherein the N atom is substituted by $T^2$, phenyl, pyrazine or pyridinyl, X is N and W2b is triazole or imidazole;

W2c is phenyl, pyridine, imidazole or triazole; $T^2$ is as defined above.

It should be understood, when X is N and W2b is triazole or imidazole that one of the N atom of the triazole or imidazole is X.

Preferably, in the compounds of the invention:

$R^1$ is chosen in the group consisting of H, CN, C(=O)NR²R³, C(=O)NHNHR², C(=O)NHOR², (CH₂)OR², (CH$_2$)NHR$^2$, (CH$_2$)NR$^4$C(=NR$^4$)N(R$^4$)$_2$, C(=NOZ$^4$) NZ$^1$Z$^2$, (CH$_2$)(5- to 6-membered heteroaryl comprising 1 to 4 heteroatom independently chosen in the group consisting of N, O or S);

R$^2$ and R$^3$, identical or different, are chosen in the group consisting of H, linear or branched (C1-C6)alkyl, (4- to 6-membered heterocyclyl comprising 1 or 2 heteroatom independently chosen in the group consisting of N, O or S), C(=O)(4- to 6-membered heterocyclyl comprising 1 or 2 heteroatom independently chosen in the group consisting of N, O or S);

R$^4$, each identical or different, is independently chosen in the group consisting of H, linear or branched (C1-C6)alkyl, wherein the alkyl is optionally substituted by one or more R$^5$;

R$^5$, each identical or different, is chosen in the group consisting of OH, O(linear or branched-C1-C6)alkyl, NH$_2$, NH(linear or branched C1-C6)alkyl, N[(linear or branched C1-C6)Alkyl]$_2$, C(=O)NH$_2$, C(=O)NH(linear or branched C1-C6)alkyl, C(=O)N[linear or branched (C1-C6)alkyl]$_2$;

Y$^2$ is chosen in the group consisting of OH, O(C1-C6)alkyl linear or branched, O-(4- to 10-membered)heterocyclyl comprising 1 or 2 heteroatom chosen in the group consisting of N, O and S; wherein the alkyl, heterocyclyl are optionally substituted by one or more Y$^5$;

Y$^5$, each identical or different, is chosen in the group consisting of linear or branched (C1-C6)alkyl, linear or branched O(C1-C6)alkyl, linear or branched O(C1-C6)alkyl-O(C1-C6)alkyl, linear or branched (C1-C6)alkyl-O(C1-C6)alkyl.

Preferably, in the compounds of the invention:

R$^1$ is chosen in the group consisting of H, CN, C(=O)NR$^2$R$^3$, C(=O)NHNHR$^2$, C(=O)NHOR$^2$, (CH$_2$)OR$^2$, (CH$_2$)NHR$^2$, (CH$_2$)NR$^4$C(=NR$^4$)N(R$^4$)$_2$, (CH$_2$)(5- to 6-membered heteroaryl comprising 1 to 4 heteroatom independently chosen in the group consisting of N, O or S);

R$^2$ and R$^3$, identical or different, are chosen in the group consisting of H, linear or branched (C1-C6)alkyl, (4- to 6-membered heterocyclyl comprising 1 or 2 heteroatom independently chosen in the group consisting of N, O or S), C(=O)(4- to 6-membered heterocyclyl comprising 1 or 2 heteroatom independently chosen in the group consisting of N, O or S);

R$^4$, each identical or different, is independently chosen in the group consisting of H, linear or branched (C1-C6)alkyl, wherein the alkyl is optionally substituted by one or more R$^5$;

R$^5$, each identical or different, is chosen in the group consisting of OH, O(linear or branched-C1-C6)alkyl, NH$_2$, NH(linear or branched C1-C6)alkyl, N[(linear or branched C1-C6)Alkyl]$_2$, C(=O)NH$_2$, C(=O)NH(linear or branched C1-C6)alkyl, C(=O)N[linear or branched (C1-C6)alkyl]$_2$;

Y$^2$ is chosen in the group consisting of OH, O(C1-C6)alkyl linear or branched, O-(4- to 10-membered)heterocyclyl comprising 1 or 2 heteroatom chosen in the group consisting of N, O and S; wherein the alkyl, heterocyclyl are optionally substituted by one or more Y$^5$;

Y$^5$, each identical or different, is chosen in the group consisting of linear or branched (C1-C6)alkyl, linear or branched O(C1-C6)alkyl, linear or branched O(C1-C6)alkyl-O(C1-C6)alkyl, linear or branched (C1-C6)alkyl-O(C1-C6)alkyl.

In one embodiment Y$^2$ represents O—CY$^6$Y$^7$Y$^8$ wherein Y$^6$, Y$^7$ and Y$^8$, identical or different, represent (C1-C3)-alkyl, (C3-C6)-cycloalkyl, (C4-C8)-heterocycloalkyl comprising from 1 to 2 heteroatoms chosen among N—Y$^{10}$, O or S, a group CH$_2$—O—(C1-C3)-alkyl, or a group CH$_2$—O—(CH$_2$)$_2$—O—(C1-C3)-alkyl, wherein the alkyl, cycloalkyl and heterocycloalkyl is optionally substituted by one or more Y$^9$; or Y$^6$ and Y$^7$ could form together with the carbon atom to which they are linked a (C3-C6)-cycloalkyl or a (C4-C8)-heterocycloalkyl comprising from 1 to 2 heteroatoms chosen among N—Y$^{10}$, O or S, wherein the cycloalkyl and heterocycloalkyl is optionally substituted by one or more Y$^9$;

Y$^{10}$ represents (C1-C6)-alkyl, (C3-C6)-cycloalkyl, C(=O)(C1-C6)-alkyl or C(=O)(C3-C6)-cycloalkyl;

Y$^9$ represents (C1-C6)-alkyl, (C3-C6)-cycloalkyl, O(C1-C6)-alkyl or O(C3-C6)-cycloalkyl.

In one embodiment, in the compounds of the invention Y$^2$ is chosen among

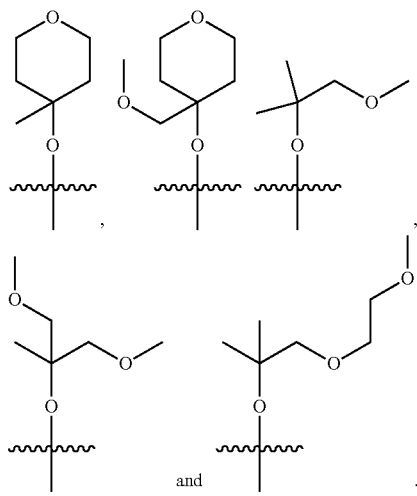

and .

The term "alkyl", as used herein, refers to an aliphatic-hydrocarbon group which may be straight or branched, having 1 to 3 carbon atoms in the chain unless specified otherwise. Preferred alkyl groups have 1 or 2 carbon atoms in the chain. Specific examples of alkyl groups include, but are not limited to, methyl, ethyl, n-propyl, isopropyl. Preferably, the alkyl group is methyl or ethyl.

The term "cycloalkyl" refers to a saturated monocyclic or bicyclic non-aromatic hydrocarbon ring of 3 to 11 carbon atoms, preferably 3 to 4 carbon atoms, which can comprise one or more unsaturation. Specific examples of monocyclic cycloalkyl groups include cyclopropyl, cyclobutyl, cyclopentyl, cyclohexyl, cyclopentenyl, cyclohexenyl. Preferably, the cycloalkyl group is cyclopropyl or cyclobutyl.

Aryl relates to an aromatic mono or bicycle comprising from 6 to 10 carbon atom. An example of aryl is phenyl, naphtyl, preferably phenyl.

The term "heterocyclyl", as used herein and without contrary definition specifically mentioned, either alone or in combination with another radical, refers to a monocyclic saturated or partially unsaturated non-aromatic ring containing from 4 to 10 atom, of which at least one atom, preferably 1 or 2 atom, of the ring is a heteroatom such as N, O, S, S(O) or S(O)$_2$. Preferably, the heterocycle is a monocyclic saturated or partially unsaturated non-aromatic ring containing from 4 to 6 atom of which at least one atom, preferably 1 or 2 atom, of the ring is a heteroatom such as N, O, S, S(O) or S(O)$_2$. The carbon atoms of the heterocyclyl can also be oxidized to form a C(O) group. Suitable heterocycles are also disclosed in the Handbook of Chemistry and Physics, 76th Edition, CRC Press, Inc., 1995-1996, pages 2-25 to 2-26. Exemplary heterocyclyl groups include but are not limited to azetidinyl, oxetanyl, oxazolyl, oxazolidinyl, oxadiazolyl, pyrrolyl, pyrrolidinyl, pyridyl, dihydropyridinyl, tetrahydropyridinyl, piperidinyl, morpholinyl, pyrazolyl, pyrimidinyl, pyrazinyl, tetrazolyl, imidazolyl, thienyl, thiazolyl, furanyl, thiadiazolyl, isothiazolyl, triazolyl, tetrazolyl, pyrazolyl, isoxazolyl, 2-pyrrolidinonyl, imidazol-2,4-dione, 1,2,4-oxadiazol-5-one, 1,5-dihydropyrrolyl-2-one, pyrazinone, pyridazinone, pyridone, pyrimidone, dioxanyl, pyrrolidinyl, imidazolidinyl, pyranyl, tetrahydrofuranyl, dioxolanyl, dihydropyranyl, tetrahydropyranyl. Without contrary definition specifically mentioned, the heterocyclyl can be carbon or nitrogen linked.

Heteroaryl as used herein and without contrary definition specifically mentioned, either alone or in combination with another radical, refers to an aromatic monocyclic heterocyclyl ring comprising from 5 to 6 atoms of which at least one atom, preferably from 1 to 4 atom, of the ring is a heteroatom such as N, O, S, S(O) or $S(O)_2$. Without contrary definition specifically mentioned, the heteroaryl can be carbon or nitrogen linked. Examples of heteroaryl are furanyl, imidazolyl, isothiazolyl, isoxazolyl, oxazolyl, pyrazinyl, pyrazolyl, pyridazinyl, pyrimidinyl, pyridinyl, pyrrolyl, tetrazolyl, thiadiazolyl, thiazolyl, thienyl, triazolyl, etc.

Moreover some compounds according to this invention may contain a basic amino group and thus may form an inner zwitterionic salt (or zwitterion) with the acidic group —$OSO_3H$, —$OCFHCO_2H$ or —$OCF_2CO_2H$ and such inner zwitterionic salts are also included in this invention.

The expression "optionally substituted" means "non-substituted or substituted by chemical groups that are further defined" or "unsubstituted or substituted chemical groups that are further defined".

The term "racemate" is employed herein to refer to an equal amount of two specific enantiomers.

The term "enantiomer" is employed herein to refer to one of the two specific stereoisomers which is a non-superimposable mirror image with one other but is related to one other by reflection.

The compounds according to the invention may include one or more asymmetric carbon atoms and may thus exist in the form of optical isomers as well as in the form of racemic or non-racemic mixtures thereof. The compounds according to the invention can be utilized as a single isomer or as a mixture of stereochemical isomeric forms. Diastereoisomers, i.e., non-superimposable stereochemical isomers can be separated by conventional means such as chromatography, distillation, crystallization or sublimation. The optical isomers (enantiomers) can be obtained by using optically active starting materials, by resolution of the racemic mixtures according to conventional processes, for example by formation of diastereoisomeric salts by treatment with an optically active acid or base or by using chiral chromatography column.

As used herein, the expression "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids or aminohydroxyl-O-sulfonic acid; and the like. The pharmaceutically acceptable salts of the present invention can be synthesized from the parent compound which comprises a basic or an acidic moiety, by conventional chemical methods. Furthermore, the expression "pharmaceutically acceptable salt" refers to relatively non-toxic, inorganic and organic acid or base addition salts of the compounds of the present invention. These salts can be prepared in situ during the final isolation and purification of the compounds. In particular, the acid addition salts can be prepared by separately reacting the purified compound in its purified form with an organic or inorganic acid and by isolating the salt thus formed. Among the examples of acid addition salts are the hydrobromide, hydrochloride, hydroiodide, sulfamate, sulfate, bisulfate, phosphate, nitrate, acetate, propionate, succinate, oxalate, valerate, oleate, palmitate, stearate, laurate, borate, benzoate, lactate, tosylate, citrate, maleate, fumarate, tartrate, naphthylate, mesylate, glucoheptanate, glucoronate, glutamate, lactobionate, malonate, salicylate, methylenebis-b-hydroxynaphthoate, gentisic acid, isethionate, di-p-toluoyltartrate, ethanesulfonate, benzenesulfonate, cyclohexyl sulfamate, quinateslaurylsulfonate salts, and the like. Examples of base addition salts include ammonium salts such as tromethamine, meglumine, epolamine, etc, metal salts such as sodium, lithium, potassium, calcium, zinc or magnesium salts with organic bases such as dicyclohexylamine salts, N-methyl-D-glucamine. Lists of suitable salts may be found in Remington's Pharmaceutical Sciences, 17th ed., Mack Publishing Company, Easton, Pa., 1985, p. 1418, P. H. Stahl, C. G. Wermuth, Handbook of Pharmaceutical salts—Properties, Selection and Use, Wiley-VCH, 2002 and S. M. Berge et al. "Pharmaceutical Salts" J. Pharm. Sci, 66: p. 1-19 (1977).

Compounds according to the invention also include isotopically-labelled compounds wherein one or more atoms is replaced by an atom having the same atomic number, but an atomic mass or mass number different from the atomic mass or mass number usually found in nature. Examples of isotopes suitable for inclusion in the compounds described above and are not limited to $^2H$, $^3H$, $^{11}C$, $^{13}C$, $^{14}C$, $^{18}F$, $^{19}F$, $^{13}N$, $^{15}N$, $^{33}S$, $^{34}S$, $^{35}S$, $^{36}S$, $^{17}O$ or $^{18}O$. Isotopically-labelled compounds are useful in drug and/or substrate tissue distribution studies. Substitution with heavier isotopes such as deuterium ($^2H$) affords greater metabolic stability (for example increased in vivo half-life or reduced dosage requirements). Isotopically-labelled compounds are prepared by any suitable method or by processes using an appropriate isotopically-labelled reagent in replacement of the non-labelled reagent otherwise employed.

The invention provides compounds having antibacterial properties and/or compounds acting as β-lactamase inhibitors.

The invention also provides a process for the preparation of a compound according to the invention.

The compounds of the present invention of formula (I) can be prepared by the following reaction Schemes 1-9.

Scheme 1: General pathway of synthesis
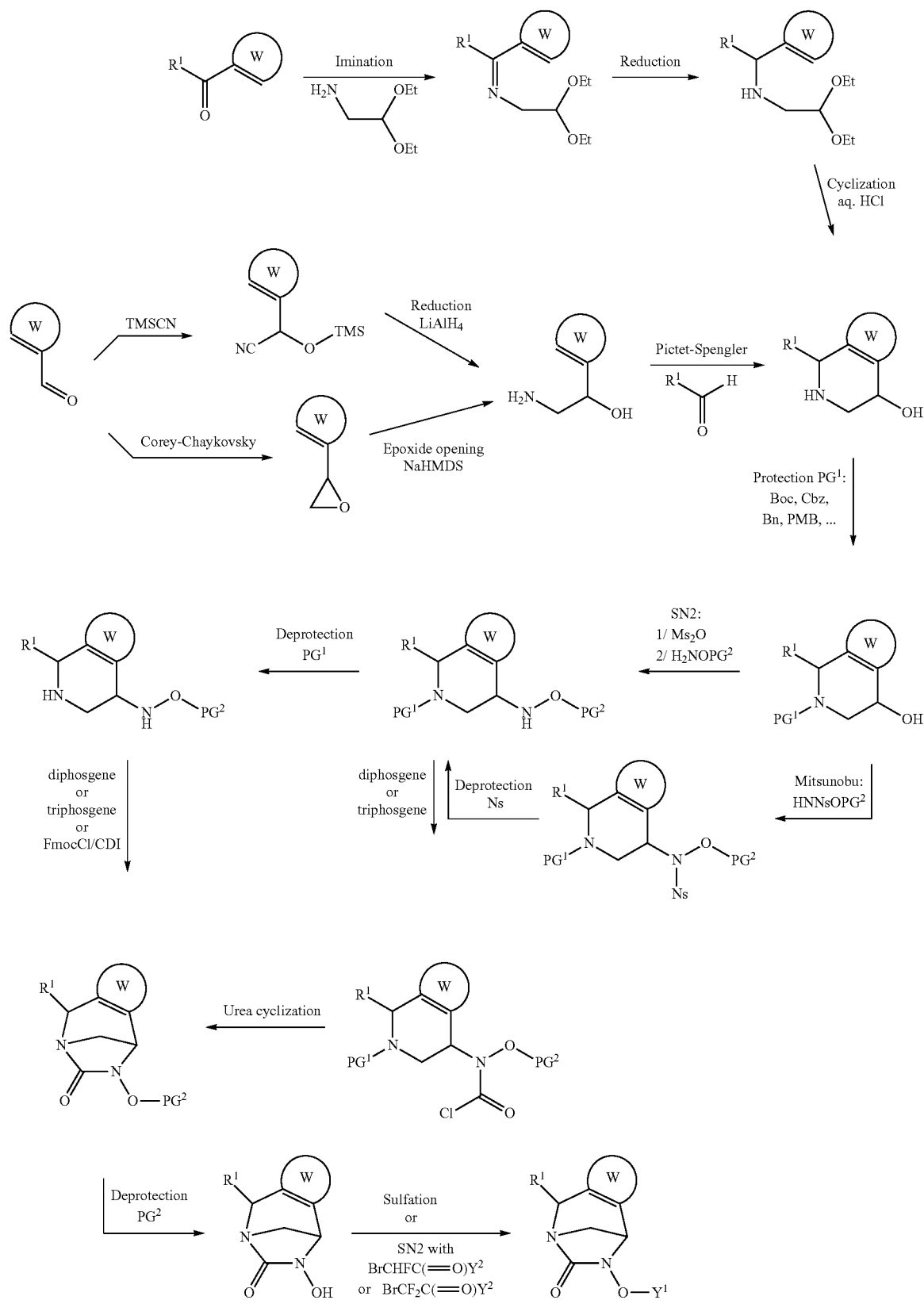

Scheme 2: $R^1$ introduction, route A
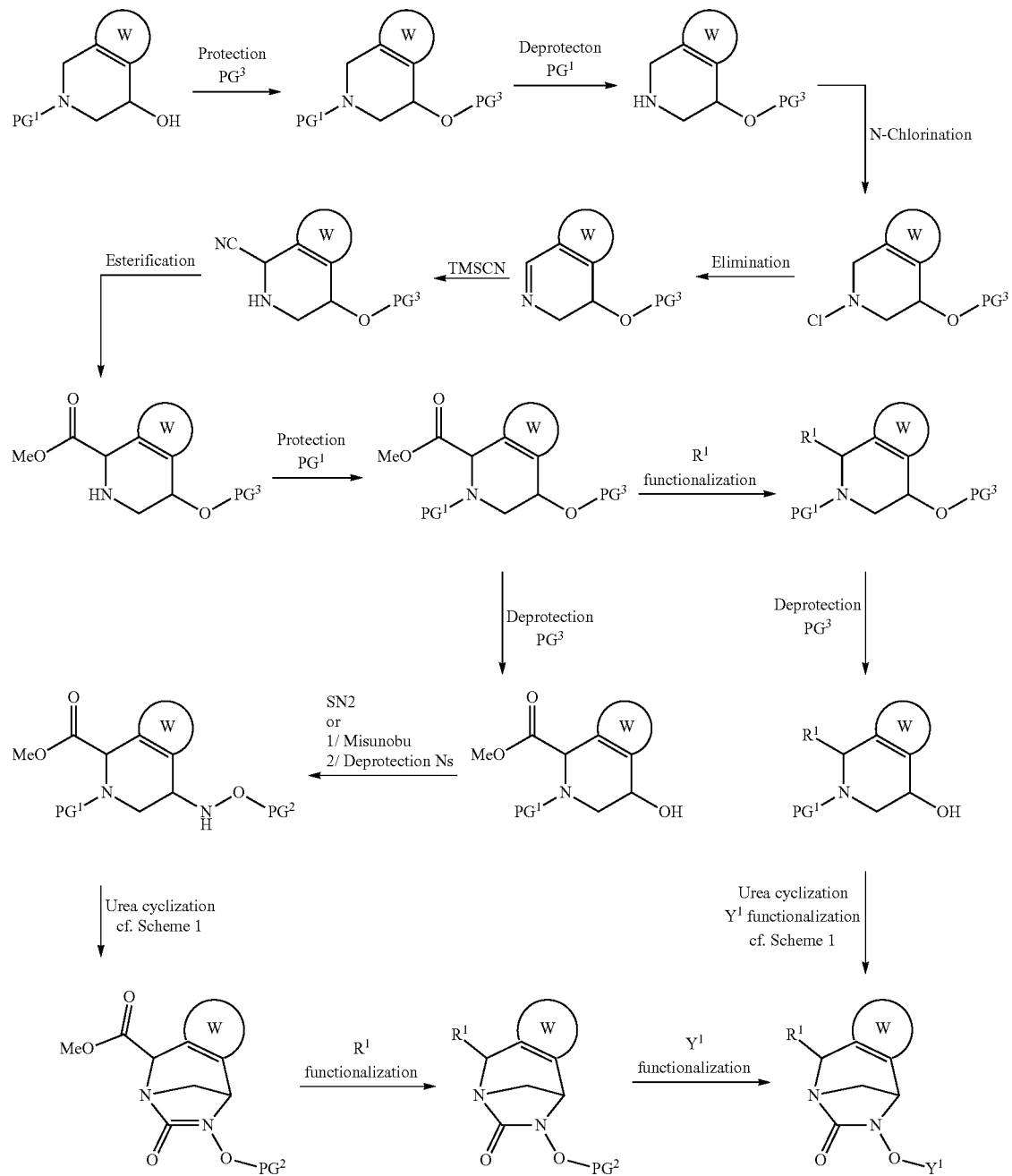
Scheme 3: $R^1$ introduction, route B
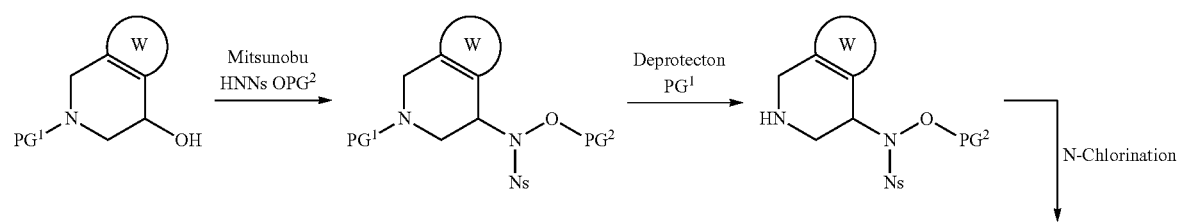

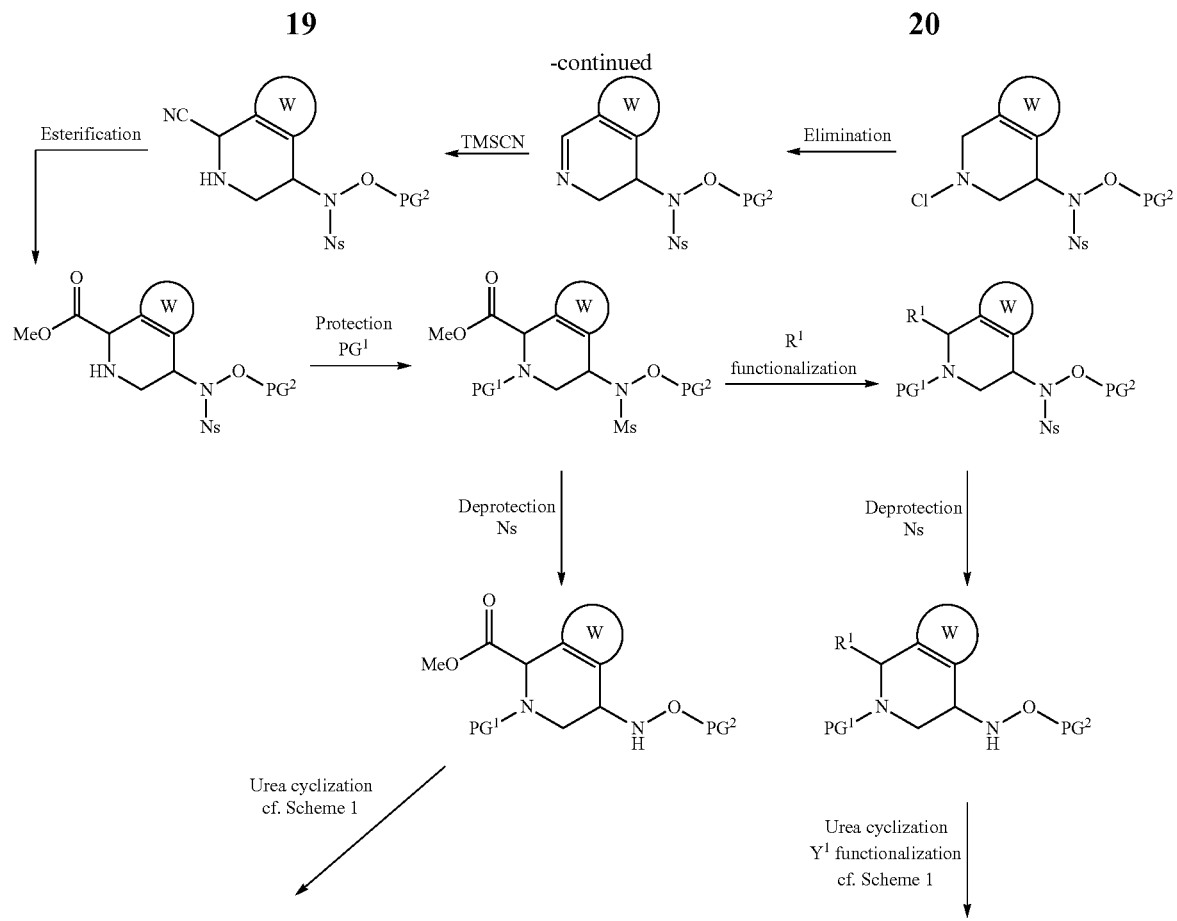
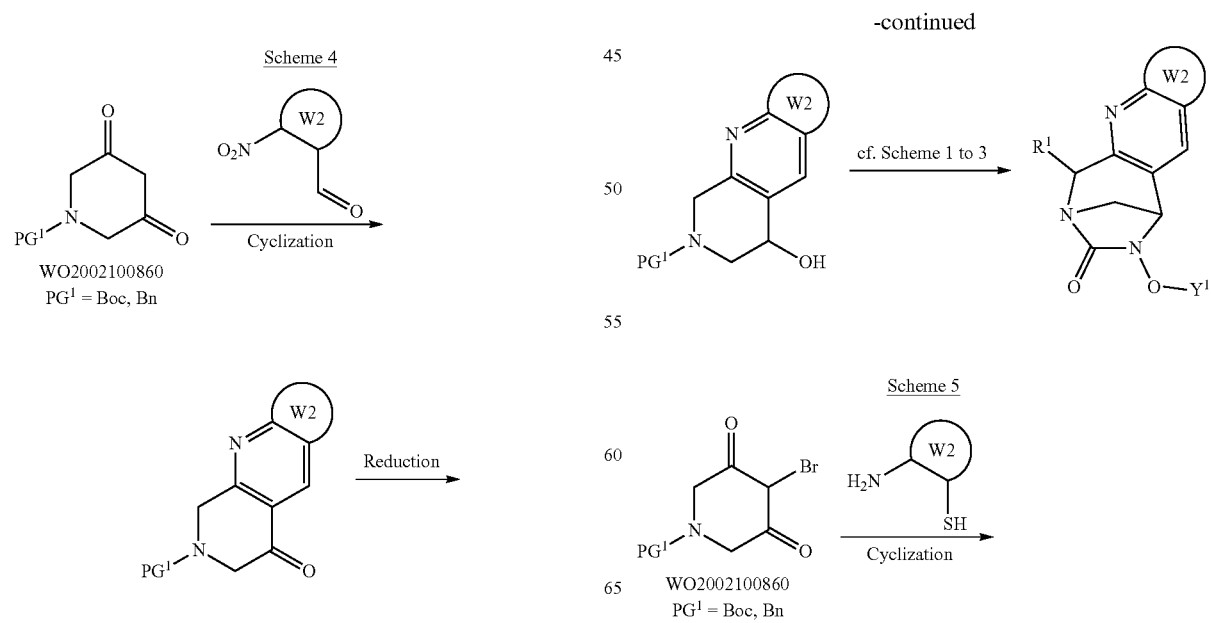

-continued
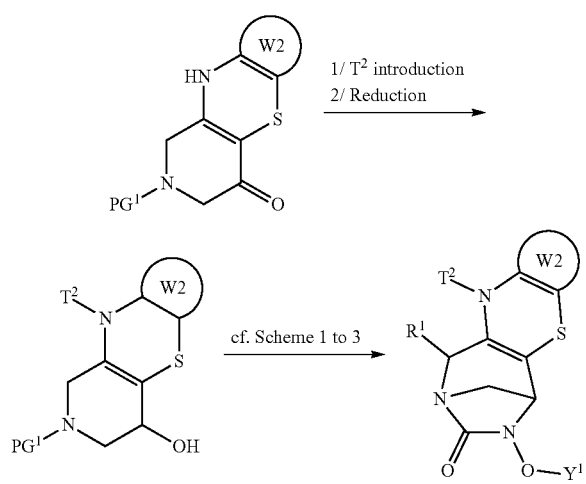
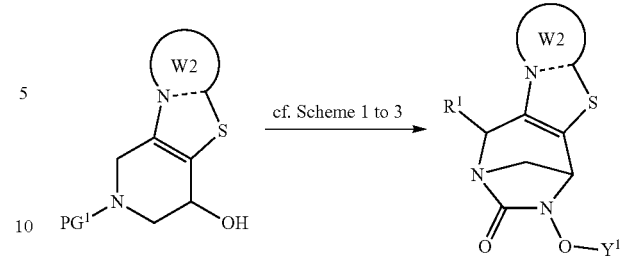
Scheme 6
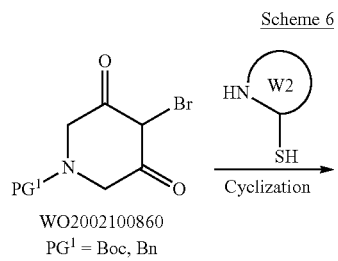
Scheme 7
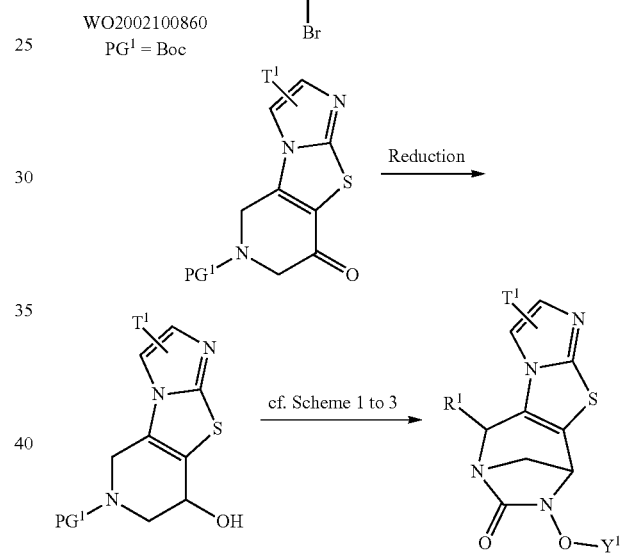
Scheme 8
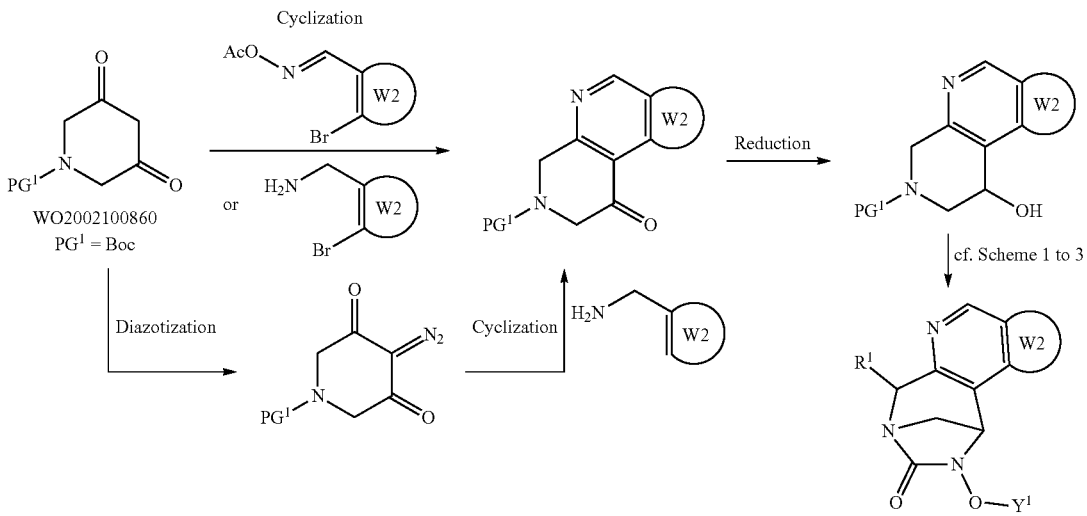

Scheme 9

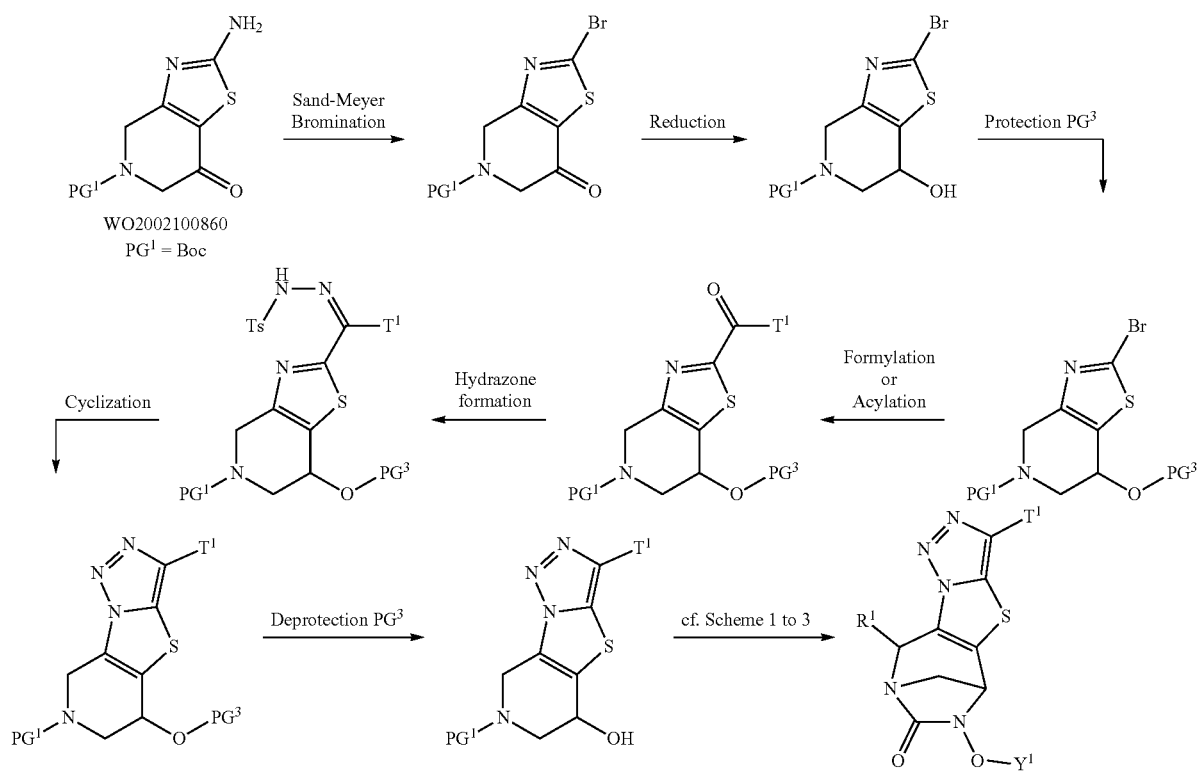

The invention also provides the use of the compounds according to the invention in the control of bacteria. The compound according to the invention is then usually used in combination with at least one pharmaceutically acceptable excipient.

The expression "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also provides a composition, preferably a pharmaceutical composition, comprising at least one compound according to the invention in mixture with a pharmaceutically acceptable excipient. The composition according to the invention may thus comprise at least one compound selected from compounds of formulae (I), (I*), (IA), (IA*) in mixture with a pharmaceutically acceptable excipient.

The composition according to the invention can further comprise at least one or more antibacterial agent(s), preferably at least one of these antibacterial agents is a beta-lactam.

The term "beta-lactam" or "β-lactam" refers to antibacterial compounds comprising a β-lactam unit, i.e. a β-lactam chemical group or moiety.

The term "pharmaceutically acceptable carrier" or "pharmaceutically acceptable excipient" is employed for any excipient, solvent, dispersion medium, absorption retardant, diluent or adjuvant etc., such as preserving or antioxidant agents, fillers, binders, disintegrating agents, wetting agents, emulsifying agents, suspending agents, solvents, dispersion media, coatings, antibacterial agents, isotonic and absorption delaying agents and the like, that does not produce a secondary reaction, for example an allergic reaction, in humans or animals. Typical, non-limiting examples of excipients include mannitol, lactose, magnesium stearate, sodium saccharide, talcum, cellulose, sodium crosscarmellose, glucose, gelatine, starch, lactose, dicalcium phosphate, sucrose, kaolin, magnesium carbonate, wetting agents, emulsifying agents, solubilizing agents, sterile water, saline, pH buffers, non-ionic surfactants, lubricants, stabilizing agents, binding agents and edible oils such as peanut oil, sesame oils and the like. In addition, various excipients commonly used in the art may be included. Pharmaceutically acceptable carriers or excipients are well known to a person skilled in the art, and include those described in Remington's Pharmaceutical Sciences (Mack Publishing Company, Easton, USA, 1985), Merck Index (Merck & Company, Rahway, N.J.), Gilman et al (Eds. The pharmacological basis of therapeutics, 8th Ed., Pergamon press, 1990). Except insofar as any conventional media or adjuvant is incompatible with the active ingredient according to the invention, its use in the therapeutic compositions is contemplated.

The expression "antibacterial agent" as used herein, refers to any substance, compound or their combination capable of inhibiting, reducing or preventing growth of bacteria, inhibiting or reducing ability of bacteria to produce infection in a subject, or inhibiting or reducing ability of bacteria to multiply or remain infective in the environment, or decreasing infectivity or virulence of bacteria.

The antibacterial agent can be selected among the following families: aminoglycosides, beta-lactams, glycylcyclines, tetracyclines, quinolones, fluoroquinolones, glycopeptides, lipopeptides, macrolides, ketolides, lincosamides, streptogramins, oxazolidinones and polymyxins alone or in mixture. Preferably, the further antibacterial agent is selected among the beta-lactam families, and more preferably among penicillin, cephalosporins, penems, carbapenems and monobactam, alone or in mixture.

Among the penicillin the antibacterial agent is preferably selected in the group consisting of amoxicillin, ampicillin, azlocillin, mezocillin, apalcillin, hetacillin, bacampicillin, carbenicillin, sulbenicillin, temocillin, ticarcillin, piperacillin, mecillinam, pivmecillinam, methicillin, ciclacillin, talampacillin, aspoxicillin, oxacillin, cloxacillin, dicloxacillin, flucloxacillin, nafcillin, and pivampicillin, alone or in mixture.

Among the cephalosporin, the antibacterial agent is preferably selected in the group consisting of cefatriazine, cefiderocol, cefazolin, cefoxitin, cephalexin, cephradine, ceftizoxime, cephacetrile, cefbuperazone, cefprozil, ceftobiprole, ceftobiprole medocaril, ceftaroline, ceftaroline fosaminyl, cefalonium, cefminox, ceforanide, cefotetan, ceftibuten, cefcapene pivoxil, cefditoren pivoxil, cefdaloxime cefroxadine, ceftolozane and S-649266, cephalothin, cephaloridine, cefaclor, cefadroxil, cefamandole, cefazolin, cephalexin, cephradine, ceftizoxime, cephacetrile, cefotiam, cefotaxime, cefsulodin, cefoperazone, cefmenoxime, cefmetazole, cephaloglycin, cefonicid, cefodizime, cefpirome, ceftazidime, ceftriaxone, cefpiramide, cefbuperazone, cefozopran, cefepime, cefoselis, cefluprenam, cefuzonam, cefpimizole, cefclidine, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbef, and latamoxef, alone or in mixture.

Among the carbapenem, the antibacterial agent is preferably selected in the group consisting of imipenem, doripenem, meropenem, biapenem, ertapenem and panipenem, alone or in mixture.

Among the monobactam, the antibacterial agent is preferably selected in the group consisting of aztreonam, tigemonam, LYS228, carumonam, BAL30072 and nocardicin A, alone or in mixture.

The present invention also relates to a composition comprising at least a compound of formulae (I), (I*), (IA), (IA*) according to the invention and ceftazidime.

The present invention also provides a kit comprising:
a pharmaceutical composition according to the invention, and
at least one other composition comprising one or more antibacterial agents, preferably at least one of these antibacterial agents is a beta-lactam.

The two compositions can each be prepared separately with one specific pharmaceutically acceptable carrier, and can then be mixed, especially extemporaneously.

The present invention also relates to a kit comprising:
a pharmaceutical composition comprising at least a compound of formulae (I) or (I*), according to the invention; and
a pharmaceutical composition comprising ceftazidime.

The present invention also refers to a compound selected within the compounds of formulae (I), (I*), (IA), (IA*) according to the invention for its use as a medicine.

The present invention also refers to a compound selected within the compounds of formulae (I), (I*), (IA), (IA*) according to the invention for its use for the preparation of a medicine.

The present invention also refers to a compound selected within the compounds of formulae (I), (I*), (IA), (IA*) according to the invention for its use as an antibacterial agent.

The present invention also refers to the use of a compound selected within the compounds of formulae (I), (I*), (IA), (IA*) according to the invention or to the use of a pharmaceutical composition according to the invention for the preparation of an antibacterial agent comprising medicine.

The present invention also refers to the use of a compound selected within the compounds of formulae (I), (I*), (IA), (IA*) according to the invention or to the use of a pharmaceutical composition according to the invention for the preparation of a beta-lactamase inhibitor comprising medicine.

The present invention also refers to the use of a compound selected within the compounds of formulae (I), (I*), (IA), (IA*) according to the invention or to the use of a pharmaceutical composition according to the invention for the preparation of a medicine comprising an antibacterial agent and a beta-lactamase inhibitor.

The present invention also refers to the use of a compound selected within the compounds of formulae (I), (I*), (IA), (IA*) according to the invention or to the use of a pharmaceutical composition according to the invention or to the use of a kit according to the invention for the treatment or for the prevention of at least one bacterial infection.

The present invention also refers to the use of a compound selected within the compounds of formulae (I), (I*), (IA), (IA*) according to the invention or to the use of a pharmaceutical composition according to the invention or to the use of a kit according to the invention for the preparation of a medicine useful in the treatment or in the prevention of at least one bacterial infection.

The terms "prevention", "prevent" and "preventing" as used herein are intended to mean the administration of a compound or composition according to the invention in order to prevent infection by bacteria or to prevent occurrence of related infection and/or diseases.

The terms "prevention", "prevent" and "preventing" also encompass the administration of a compound or composition according to the present invention in order preventing at least one bacterial infection, by administration to a patient susceptible to be infected, or otherwise at a risk of being infected by this bacteria.

The terms "treatment", "treat" and "treating" as used herein are intended to mean in particular the administration of a treatment comprising a compound or composition according to the invention to a patient suffering from an infection. The terms "treatment", "treat" and "treating" as used herein, also refer to administering a compound or composition according to the invention, optionally in combination with one or more further antibacterial agent, in order:
to reduce or to eliminate either bacterial infection or one or more symptoms associated with a bacterial infection, or
to retard the progression of a bacterial infection or of one or more symptoms associated with a bacterial infection, or
to reduce the severity of a bacterial infection or of one or more symptoms associated with a bacterial infection, or
to suppress the clinical manifestation of a bacterial infection, or
to suppress the manifestation of adverse symptoms caused by a bacterial infection.

The expression "infection" or "bacterial infection" as used herein, include the presence of bacteria, in or on a subject, which, if its growth were inhibited, would result in a benefit to the subject. As such, the term "infection" or "bacterial infection" in addition to referring to the presence of bacteria also refer to normal flora, which is not desirable. The term "infection" includes infection caused by bacteria. Examples of such bacterial infections are urinary tract infection (UTI), kidney infections (pyelonephritis), gynecological and obstetrical infections, respiratory tract infection (RTI), acute exacerbation of chronic bronchitis (AECB), Community-acquired pneumonia (CAP), hospital-acquired pneumonia (HAP), ventilator associated pneumonia (VAP), intra-abdominal pneumonia (IAI), acute otitis media, acute sinusitis, sepsis, catheter-related sepsis, chancroid, chlamydia, skin infections, bacteremia.

The term "growth" as used herein, refers to the growth of one or more microorganisms and includes reproduction or population expansion of a microorganism, such as bacteria. The term also includes maintenance of on-going metabolic processes of a microorganism, including processes that keep the microorganism alive.

According to the invention, bacteria are chosen amongst gram-positive bacteria or gram-negative bacteria, preferably gram-negative bacteria. According to the invention, bacteria can be also chosen among bacteria producing "beta-lactamase" or "β-lactamase". These bacteria are well known by the person skilled in the art. The term "beta-lactamase" or "β-lactamase" as used herein, refers to any enzyme or protein or any other substance that is able to break down a beta-lactam ring. The term "beta-lactamase" or "β-lactamase" includes enzymes that are produced by bacteria and that have the ability to hydrolyze, either partially or completely, the beta-lactam ring present in a compound such as an antibacterial agent.

Among the gram-positive bacteria, the bacteria according to the invention is preferably chosen among *Staphylococcus, Streptococcus, Staphylococcus* species (including *Staphylococcus aureus, Staphylococcus epidermidis*), *Streptococcus* species (including *Streptococcus pneumonia, Streptococcus agalactiae*), *Enterococcus* species (including *Enterococcus faecalis* and *Enterococcus faecium*).

Among the gram-negative bacteria, the bacteria according to the invention is preferably chosen among *Acinetobacter* species (including *Acinetobacter baumannii*), *Citrobacter* species, *Escherichia* species (including *Escherichia coli*), *Haemophilus* influenza, *Morganella morganii, Klebsiella* species (including *Klebsiella pneumonia*), *Enterobacter* species (including *Enterobacter cloacae*), *Neisseria gonorrhoeae, Burkholderia* species (including *Burkholderia cepacia*), (*Proteus* species (including *Proteus mirabilis*), *Serratia* species (including *Serratia marcescens*), *Pseudomonas aeruginosa*.

The invention thus preferably refers to a compound selected within the compounds of formulae (I), (I*), (IA), (IA*) according to the invention or to a pharmaceutical composition according to the invention or to a kit according to the invention for its use for the treatment or for the prevention of a bacterial infection, preferably caused by bacteria producing one or more beta-lactamases. Preferably, the bacteria are chosen amongst gram-positive bacteria or gram-negative bacteria, more preferably gram-negative bacteria.

The present invention also refers to the use of a compound selected within the compounds of formulae (I), (I*), (IA), (IA*) according to the invention or to a pharmaceutical composition according to the invention for the preparation of a medicine for the treatment or for the prevention of a bacterial infection, preferably caused by bacteria producing one or more beta-lactamases. Preferably, the bacteria are chosen amongst gram-positive bacteria or gram-negative bacteria, more preferably gram-negative bacteria.

The present invention also refers to a kit according to the invention, for its simultaneous, separated or sequential administration to a patient in need thereof in the treatment or in the prevention of bacterial infections, preferably caused by bacteria producing one or more beta-lactamases. Preferably, the bacteria are chosen amongst gram-positive bacteria or gram-negative bacteria, more preferably gram-negative bacteria.

The present invention also refers to a compound selected within the compounds of formulae (I), (I*), (IA), (IA*) according to the invention for its use in combination with one or more further antibacterial agents, preferably at least one of the further antibacterial agents being a beta lactam compound, for the treatment or for the prevention of bacterial infections, preferably caused by bacteria producing one or more beta-lactamases. Preferably, the bacteria are chosen amongst gram-positive bacteria or gram-negative bacteria, more preferably gram-negative bacteria, and wherein a compound selected within the compounds of formulae (I) or (I*) according to the invention and the further antibacterial agent are administered simultaneously, separately or sequentially.

The present invention also refers to the use of a compound selected within the compounds of formulae (I), (I*), (IA), (IA*) according to the invention or of a pharmaceutical composition according to the invention or of a kit according to the invention for the prevention or for the treatment of bacterial infections, preferably of a bacterial infection, preferably caused by bacteria producing one or more beta-lactamases. Preferably, the bacteria are chosen amongst gram-positive bacteria or gram-negative bacteria, more preferably gram-negative bacteria.

The present invention also relates to a method for the treatment or prevention of bacterial infections, preferably caused by bacteria producing one or more beta-lactamases comprising the administration of a therapeutically effective amount of a compound selected within the compounds of formulae (I), (I*), (IA), (IA*) according to the invention, or of a pharmaceutical composition according to the invention or of a kit according to the invention to a patient in need thereof. Preferably, the bacteria are chosen amongst gram-positive bacteria or gram-negative bacteria, more preferably gram-negative bacteria.

The term "patient" means a person or an animal at risk of being infected by bacteria or, a person or an animal being infected by bacteria, preferably by gram-positive and by gram-negative bacteria, more preferably by gram-negative bacteria. As used herein, the term "patient" refers to a warm-blooded person or animal such as a mammal, preferably a human or a human child, who is afflicted with, or has the potential to be afflicted with one or more infections and conditions described herein. The identification of those subjects who are in need of treatment of herein-described diseases and conditions is well within the ability and knowledge of one skilled in the art. A veterinarian or a physician skilled in the art can readily identify, by the use of clinical tests, physical examination, medical or family history or biological and diagnostic tests, those subjects who are in need of such a treatment.

The expression "therapeutically effective amount" or "pharmaceutically effective amount" as used herein, refer to an amount of a compound according to the invention, which when administered to a patient in need thereof, is sufficient to effect treatment for disease-states, conditions, or disorders for which the compound has utility. Such an amount would be sufficient to elicit the biological or medical response of a tissue system, or patient that is sought by a researcher or a clinician. The amount of a compound according to the invention which constitutes a "therapeutically effective amount" will vary, notably depending on the compound itself and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a "therapeutically effective amount" can be determined by one of ordinary skilled in the art having regard to its own knowledge, and this disclosure. Preferably, the compound according to the invention is administered in an amount comprised between 0.1 to 30 g per day.

The compound according to the invention may be provided in an aqueous physiological buffer solution for parenteral administration. The compound of the present invention is also capable of being administered in unit dose forms, wherein the expression "unit dose" means a single dose which is capable of being administered to a patient, and which can be readily handled and packaged, remaining as a physically and chemically stable unit dose comprising either the active compound itself, or as a pharmaceutically acceptable composition, as described herein. The compound provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via trans-dermal patches.

The pharmaceutical composition may be conveniently administered in unit dosage form and may be prepared by any method well-known in the pharmaceutical art, for example, as described in Remington: The Science and Practice of Pharmacy, 20th ed.; Gennaro, A. R., Ed.; Lippincott Williams & Wilkins: Philadelphia, Pa., 2000.

Preferred formulations include pharmaceutical compositions wherein a compound according to the present invention is formulated for oral or parenteral administration.

For oral administration, tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings and flavorings. In addition, the active compounds may be incorporated into fast dissolved, modified-release or sustained-release preparations and formulations, and wherein such sustained-release formulations are preferably bi-modal. Preferred tablets contain lactose, cornstarch, magnesium silicate, crosscarmellose sodium, povidone, magnesium stearate or talc in any combination.

Liquid preparations for parenteral administration include sterile aqueous or non-aqueous solutions, suspensions and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compound. Intravenous vehicles can include fluid and nutrient replenishers, electrolyte replenishers, such as those based on Ringer's dextrose, and the like. Other potentially useful parenteral delivery systems for the active compound include ethylene-vinyl acetate copolymer particles, osmotic pumps, implantable infusion systems and liposomes.

Alternative modes of administration include formulations for inhalation, which include such means as dry powder, aerosol, or drops. They may be aqueous solutions comprising, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, and may include a salicylate.

Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations.

Formulations suitable for transdermal administration can be presented as discrete patches and can be lipophilic emulsions or buffered, aqueous solutions, dissolved and/or dispersed in a polymer or an adhesive.

EXAMPLES

The following examples are provided for the purpose of illustrating the present invention and by no means should be interpreted to limit the scope of the present invention.

Preparation of the compounds and biological activity:
Abbreviations or symbols used herein include:
ACHN: 1,1'-azobis(cyclohexanecarbonitrile)
ACN: acetonitrile
AcOH: acetic acid
Bn: benzyl
Boc: tert-butoxycarbonyl
Boc$_2$O: tert-butoxycarbonyl anhydride
BocON: [2-(tert-butoxycarbonyloxyimino)-2-phenylacetonitrile]
bs: broad singlet
Burgess reagent: methyl N-(triethylammoniosulfonyl)carbamate
CDI: 1,1'-Carbonyldiimidazole
CFU: colony-forming units
CLSI: clinical laboratory standards institute
d: doublet DBU: 1,8-diazabicyclo[5.4.0]undec-7-ene
DCM: dichloromethane
dd: double doublet
ddd: double double doublet
ddt: double double triplet
dq: double quartet
dt: double triplet
DTAD: di-tert-butylazodicarboxylate
DEAD: diethyl azodicarboxylate
Dess-Martin periodinane: 1,1,1-tris(acetyloxy)-1,1-dihydro-1,2-benziodoxol-3-(1H)-one
DHP 3,4-dihydro-2H-pyran
DIAD: diisopropyl azodicarboxylate
DIPEA: N,N-diisopropylethylamine
DMAP: 4-dimethylaminopyridine
DMF: N,N-dimethylformamide
DMSO: dimethylsulfoxide
EtOAc: ethyl acetate
Et$_2$O: diethyl ether
Fmoc-Cl: 9-Fluorenylmethyl chloroformate
h: hours
HATU: 1-[Bis(dimethylamino)methylene]-1H-1,2,3-triazolo[4,5-b]pyridinium-3-oxid hexafluorophosphate
m: multiplet
min: minutes
MeOH: methanol
MeONa: sodium methoxide
MIC: minimum inhibitory concentration
MS: mass spectrometry
MsCl: methanesulfonyl chloride
MTBE: tert-butyl methyl ether NBS: N-bromosuccinimide
NMR: nuclear magnetic resonance spectroscopy
Ns: nosyl, nitrobenzenesulfonyl
Pd(Ph$_3$)$_4$: tetrakis(triphenylphosphine)palladium(0)
PG: protective group
PhSH: thiophenol
PMe$_3$: trimethylphosphine
PPh$_3$: triphenylphosphine
Ppm: parts per million
q: quartet
rt: room temperature
s: singlet
SEM: [2-(trimethylsilyl)ethoxy]methyl
t: triplet
TBAF: tetra-n-butylammonium fluoride
TBDMSCl: tert-butyldimethylsilyl chloride
TBDMSOTf: trifluoromethanesulfonic acid tert-butyldimethylsilyl ester
TBSOTf: trimethylsilyl trifluoromethanesulfonate
tBuOK: potassium tert-butoxide
TEA: triethylamine
TFA: trifluoroacetic acid
THF: tetrahydrofuran
THP: tetrahydropyranyl
TLC: thin layer chromatography
TMSI: Iodotrimethylsilane Example 1: Synthesis of Sodium (2,5-methano-3-oxo-1,5-dihydrobenzothiopheno[2,3-e][1,3]diazepin-4-yl) sulfate

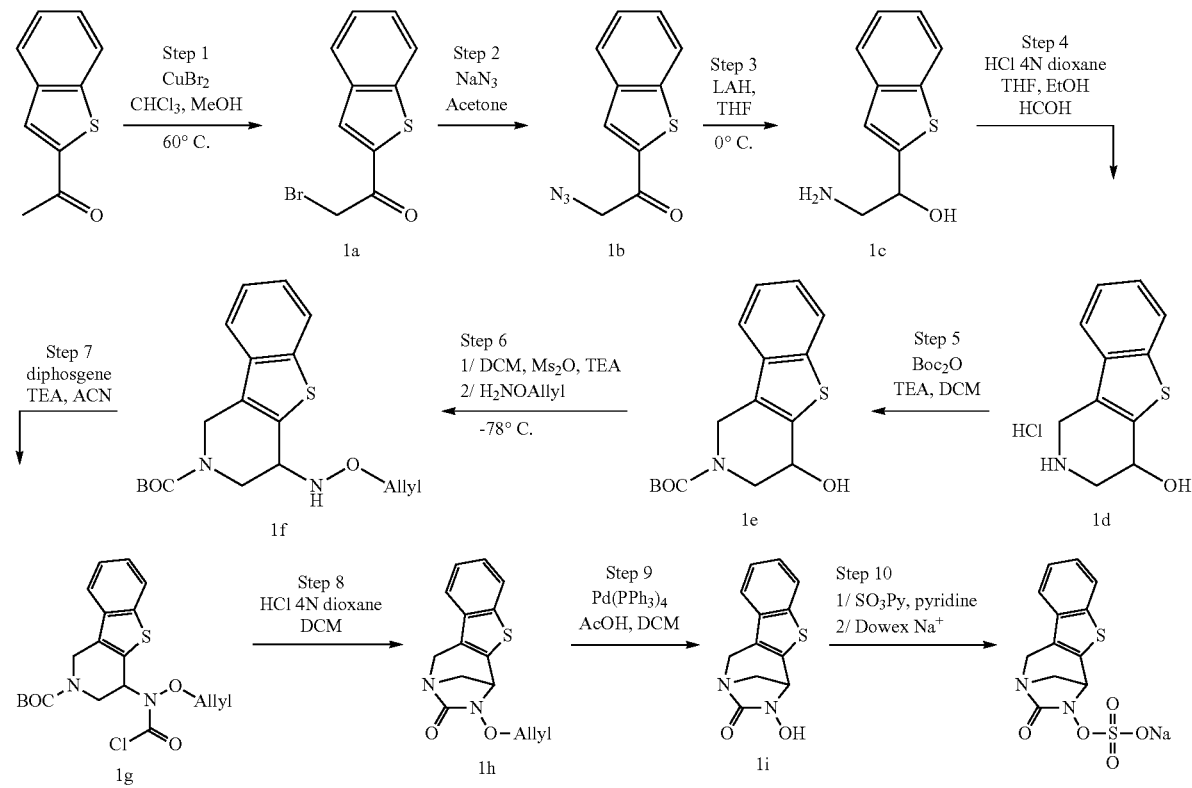

Step 1: Preparation of Intermediate 1-(benzothiophen-2-yl)-2-bromo-ethanone (1a)

1-(benzothiophen-2-yl)ethanone (5 g, 28.36 mmol) was solubilized into a mixture of $CHCl_3$/MeOH (5/1) under argon atmosphere. Copper(II) bromide (12.7 g, 56.74 mmol), was added and the mixture was warmed at 60° C. for 16 h. The reaction was evaporated and the residue was triturated with MTBE and pentane. The precipitate was filtrated to give intermediate (1a) (6.9 g, 27.04 mmol, 95%) slightly contaminated by di-brominated byproduct. MS m/z ([M+H]$^+$) 255 (bromine isotopy).

Step 2: Preparation of Intermediate 2-azido-1-(benzothiophen-2-yl)ethanone (1b)

Intermediate (1a) (6.9 g, 27.04 mmol) was solubilized into acetone (200 mL). Sodium azide (1.76 g, 27.04 mmol) was added and the mixture was stirred for 16 h at rt. The precipitate was filtered on Celite and the filtrate was evaporated. The residue was triturated successively with MTBE and pentane and then filtered to give intermediate (1b) (4.04 g, 18.42 mmol, 68%). MS m/z ([M+Na]$^+$) 240. $^1$H NMR (400 MHz, $CDCl_3$): δ (ppm) 4.57 (s, 2H), 7.42-7.47 (m, 1H), 7.49-7.54 (m, 1H), 7.88-7.94 (m, 2H), 7.98 (s, 1H).

Step 3: Preparation of Intermediate 2-amino-1-(benzothiophen-2-yl)ethanol (1c)

To a solution of intermediate (1 b) (1.92 g, 8.76 mmol) in THF (78 mL) under inert atmosphere at 0° C. was dropped a solution of LAH (2N in THF) (9.6 mL, 19.2 mmol). After stirring for 1 h, the mixture was quenched with ice and HCl 1N. The colored impurities were extracted with DCM. Then the aqueous layer was neutralized with NaOH 1N and the product was extracted with EtOAc. The organic layer was dried over $Na_2SO_4$, filtered and concentrated. The residue was triturated with $Et_2O$ to give intermediate (1c) as an off-white solid (1.40 g, 7.24 mmol, 82%). MS m/z ([M-OH]$^+$) 176. $^1$H NMR (400 MHz, $CDCl_3$: δ (ppm) 2.02 (bs, 2H), 3.03 (dd, J=6.7, 12.8 Hz, 1H), 3.14 (dd, J=4.1, 12.8 Hz, 1H), 4.92-4.99 (m, 1H), 7.21 (s, 1H), 7.29-7.38 (m, 2H), 7.73 (d, J=7.3 Hz, 1H), 7.83 (d, J=7.3 Hz, 1H).

Step 4: Preparation of Intermediate 1,2,3,4-tetrahydrobenzothiopheno[3,2-c]pyridin-4-ol hydrochloride (1d)

To a solution of intermediate (1c) (0.250 g, 1.29 mmol) in EtOH (20 mL) were added formaldehyde (37% wt solution in water, 0.145 mL, 1.94 mmol) and HCl 4N/dioxane (0.323 mL, 1.29 mmol). After stirring for 16 h at 80° C., conversion was not completed. So, formaldehyde 37% wt solution in water (0.250 mL, 3.36 mmol) was added and the mixture was heated at 80° C. for 16 h (operation was repeated until complete conversion). The mixture was cold and dried under nitrogen flux. The residue was triturated with $Et_2O$ to give intermediate (1d) (0.312 g, 1.29 mmol, quantitative). MS m/z ([M+H]$^+$) 206.

Step 5: Preparation of Intermediate tert-butyl 4-hydroxy-3,4-dihydro-1H-benzothiopheno[3,2-c]pyridine-2-carboxylate (1e)

To a solution of intermediate (1d) (0.312 g, 1.29 mmol) in DCM (13 mL) under argon atmosphere at 0° C. were successively added $Boc_2O$ (0.310 mg, 1.42 mmol) and TEA (0.450 mL, 3.23 mmol). After stirring for 18 h at rt, the mixture was evaporated under nitrogen flux and the residue was purified by column chromatography on silica gel (DCM/acetone 10/0 to 9/1) to give intermediate (1e) as a white solid (0.357 g, 1.17 mmol, 90%). MS m/z ([M+Na]$^+$) 328. $^1$H NMR (400 MHz, $CDCl_3$): δ (ppm) 1.52 (s, 9H), 3.81 (d, J=13.6 Hz, 1H), 3.99 (dd, J=4.8, 13.6 Hz, 1H), 4.53 (d, J=16.7 Hz, 1H), 4.84-4.93 (m, 2H), 7.35-7.41 (m, 2H), 7.59-7.64 (m, 1H), 7.83-7.85 (m, 1H).

Step 6: Preparation of Intermediate tert-butyl 4-(allyloxyamino)-3,4-dihydro-1H-benzothiopheno[3,2-c]pyridine-2-carboxylate (1f)

To a solution of intermediate (1e) (0.355 g, 1.16 mmol) in DCM (13 mL) under argon atmosphere at −78° C. were successively added TEA (0.650 mL, 4.64 mmol) and methanesulfonic anhydride (0.606 g, 3.48 mmol). After stirring for 1 h at −78° C., 0-allylhydroxylamine 60% (0.990 g, 8.14 mmol) in DCM (3.5 mL) was dropped into the mixture which was stirred for 20 min at −78° C. The temperature was then raised at rt for 2 h30. The mixture was quenched with saturated aqueous $NaHCO_3$ and extracted with DCM. The organic extract was dried over $Na_2SO_4$, filtered and concentrated. The residue was purified by column chromatography on silica gel (cyclohexane/EtOAc 100/0 to 95/5) to give intermediate (1f) (0.338 g, 0.938 mmol, 80%). MS m/z ([M+H]$^+$) 361. $^1$H NMR (300 MHz, $CDCl_3$): δ (ppm) 1.52 (s, 9H), 3.60-3.70 (m, 1H), 4.20-4.50 (m, 5H), 4.80-4.95 (m, 1H), 5.22 (d, J=10.4 Hz, 1H), 5.32 (d, J=16.3 Hz, 1H), 5.97 (ddt, J=5.9, 10.4, 16.3 Hz, 1H), 7.31-7.40 (m, 2H), 7.59-7.61 (m, 1H), 7.80-7.82 (m, 1H).

Step 7: Preparation of Intermediate tert-butyl 4-[allyloxy(chlorocarbonyl)amino]-3,4-dihydro-1H-benzothiopheno[3,2-c]pyridine-2-carboxylate (1q)

To a solution of intermediate (1f) (0.338 g, 0.94 mmol) in ACN (17 mL) under argon atmosphere at −10° C. were successively added TEA (0.393 mL, 2.82 mmol) and a solution of diphosgene (0.147 mL, 1.22 mmol) in ACN (2.3 mL). After stirring for 30 min at −10° C., the mixture was evaporated under nitrogen flux. The residue was triturated with DCM and evaporated under nitrogen flux again. The residue was triturated with $Et_2O$ and the insoluble was filtered off. The filtrate was concentrated to give intermediate (1 g) (0.280 g, 0.662 mmol, 70%) which was used in the next step without further purification. MS m/z ([M+Na]$^+$) 445.

Step 8: Preparation of Intermediate 4-allyloxy-2,5-methano-1,5-dihydrobenzothiopheno[2,3-e][1,3]diazepin-3-one (1 h)

To a solution of intermediate (1 g) (0.280 g, 0.662 mmol) in DCM (2.2 mL) under argon atmosphere at 0° C. was dropped HCl 4N in dioxane (6.6 mL, 40 mmol). After stirring for 1 h at rt, the mixture was evaporated under nitrogen flux. The residue was triturated with $Et_2O$ to give intermediate (1 h) as a brown oil (0.040 g, 0.140 mmol, 21%). MS m/z ([M+H]$^+$) 287.

Step 9: Preparation of Intermediate 4-hydroxy-2,5-methano-1,5-dihydrobenzothiopheno[2,3-e][1,3]diazepin-3-one (1i)

A solution of intermediate (1 h) (0.040 g, 0.140 mmol) in DCM (2 mL) was degassed 10 min under argon atmosphere.

AcOH (0.016 mL, 0.278 mmol) and Pd(PPh$_3$)$_4$ (0.081 g, 0.07 mmol) were successively added. After stirring for 30 min at rt, the mixture was evaporated under nitrogen flux. The residue was purified by column chromatography on silica gel (DCM/acetone 10/0 to 8/2). The fractions of interest are combined and concentrated. The residue was triturated with Et$_2$O to give intermediate (1i) as a yellow solid (0.013 g, 0.053 mmol, 38%). MS m/z ([M+H]$^+$) 247. $^1$H NMR (400 MHz, acetone-d$_6$): δ (ppm) 3.32 (d, J=10.9 Hz, 1H), 3.78 (dd, J=2.8, 10.9 Hz, 1H), 4.39 (d, J=16.6 Hz, 1H), 4.50 (d, J=2.8 Hz, 1H), 4.63 (d, J=16.6 Hz, 1H), 7.41-7.31 (m, 2H), 7.62-7.70 (m, 1H), 7.79-7.81 (m, 1H).

Step 10: Preparation of Sodium (2,5-methano-3-oxo-1,5-dihydrobenzothiopheno[2,3-e][1,3]diazepin-4-yl) sulfate, Example 1

To a solution of intermediate (1i) (0.013 g, 0.053 mmol) in anhydrous pyridine (0.6 mL) under inert atmosphere was added sulfur trioxide pyridine complex (0.050 g, 0.317 mmol). After stirring for 18 h, the heterogeneous mixture was concentrated in vacuum. DCM was added and the insoluble was filtered off. The filtrate concentrated. The residue was purified by flash chromatography on silica gel (DCM/acetone 10/0 to 0/10) to give Example 1 as pyridinium salt (6 mg, 0.018 mmol). The pyridinium salt was applied on a Dowex sodium form column (Dowex® 50WX8 hydrogen form stored with an aqueous solution of 2N NaOH and washed until neutral pH with water). The fractions containing the desired compound were combined, frozen and lyophilized. The solid was triturated with DCM to give Example 1 (2.7 g, 0.0083 mmol, 15%). MS m/z ([M−H]$^−$) 325. $^1$H NMR (400 MHz, D$_2$O): δ (ppm) 3.70 (d, J=11.4 Hz, 1H), 4.0 (dd, J=3.0, 11.4 Hz, 1H), 4.68 (s, 2H), 5.11 (d, J=2.9 Hz, 1H), 7.44-7.52 (m, 2H), 7.68-7.74 (m, 1H), 7.97-8.03 (m, 1H).

Example 2: Synthesis of sodium trans-(1-ethoxycarbonyl-2,5-methano-3-oxo-1,5-dihydrobenzothiopheno[2,3-e][1,3]diazepin-4-yl) sulfate

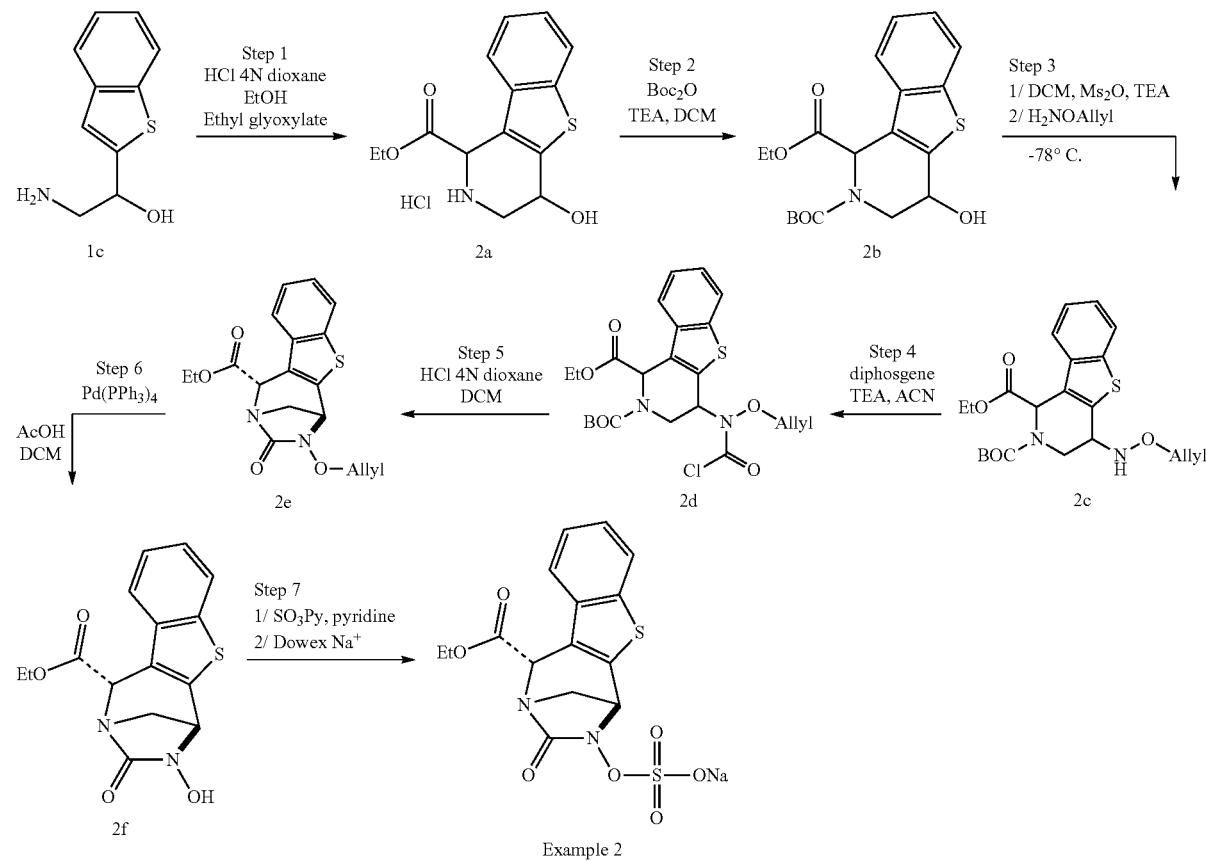

Example 2

Step 1: Preparation of Intermediate ethyl 4-hydroxy-1,2,3,4-tetrahydrobenzothiopheno[3,2-c]pyridine-1-carboxylate Hydrochloride (2a)

To a solution of intermediate (1c) (1 g, 5.17 mmol) into EtOH (51 mL) were added ethyl glyoxylate 50% solution in toluene (1.54 mL, 7.76 mmol) and HCl 4N in dioxane (1.30 mL, 5.17 mmol). After stirring for 16 h at 80° C., the mixture was cold and the precipitate was filtered to give intermediate (2a) as a white solid (1.19 g, 3.79 mmol, 73%). MS m/z ([M+H]$^+$) 278. $^1$H NMR (300 MHz, D$_2$O): δ (ppm) 1.23 (t, J=7.1 Hz, 3H), 3.64 (dd, J=9.0, 12.7 Hz, 1H), 3.95-4.03 (m, 1H), 4.24-4.42 (m, 2H), 5.40 (ddd, J=1.2, 6.0, 9.0 Hz, 1H), 5.84 (s, 1H), 7.51-7.60 (m, 2H), 8.02-8.04 (m, 2H).

Step 2: Preparation of Intermediate O2-tert-butyl O1-ethyl 4-hydroxy-3,4-dihydro-1H-benzothiopheno[3,2-c]pyridine-1,2-dicarboxylate (2b)

To a solution of intermediate (2a) (1.13 g, 3.60 mmol) in DCM (36 mL) under argon atmosphere at 0° C. were successively added Boc₂O (0.864 mg, 3.96 mmol) and TEA (1.25 mL, 9 mmol). After 16 h at rt, the mixture was washed with NaOH 1N and extracted with EtOAc. The organic layer was dried over Na₂SO₄, filtered and concentrated to give intermediate (2b) as a white solid (1.36 g, 3.60 mmol, quantitative, mixture of diastereoisomers). MS m/z ([M+Na]⁺) 400. ¹H NMR (400 MHz, CDCl₃): δ (ppm) 1.22 (q, J=6.9 Hz, 3H), 1.53 (s, 9H), 3.7-3.84 (m, 1H), 4.14-4.21 (m, 3H), 4.92-4.97 (m, 1H), 5.68 and 5.79 (2s, 1H), 7.35-7.45 (m, 2H), 7.84 (d, J=7.8 Hz, 1H), 8.00 (d, J=7.8 Hz, 1H).

Step 3: Preparation of Intermediate O2-tert-butyl O1-ethyl 4-(allyloxyamino)-3,4-dihydro-1H-benzothiopheno[3,2-c]pyridine-1,2-dicarboxylate (2c)

To a solution of intermediate (2b) (800 mg, 2.12 mmol) in DCM (24 mL) under argon atmosphere at −78° C. were successively added TEA (1.19 mL, 8.48 mmol) and methanesulfonic anhydride (1.11 g, 6.36 mmol). After stirring for 1 h at −78° C., 0-allylhydroxylamine 60% (1.80 g, 14.84 mmol) in DCM (6.4 mL) was dropped. The mixture was stirred for 1 h20 at −78° C. then the temperature was raised at rt for 1 h30. The mixture was diluted with DCM and washed with saturated aqueous NaHCO₃. The organic extract was dried over Na₂SO₄, filtered and concentrated. The residue was purified by column chromatography on silica gel (cyclohexane/EtOAc 10/0 to 95/5) to give intermediate (2c) as a colorless oil (0.762 g, 1.76 mmol, 83%). MS m/z ([M+H]⁺) 433. ¹H NMR (400 MHz, CDCl₃): δ (ppm) 1.22-1.28 (m, 3H), 1.50-1.54 (m, 9H), 3.68-4.76 (m, 7H), 5.21-5.43 (m, 2H), 5.69-6.00 (m, 2H), 7.32-7.44 (m, 2H), 7.78-7.83 (m, 1H), 8.01-8.08 (m, 1H).

Step 4: Preparation of Intermediate O2-tert-butyl O1-ethyl 4-[allyloxy(chlorocarbonyl)amino]-3,4-dihydro-1H-benzothiopheno[3,2-c]pyridine-1,2-dicarboxylate (2d)

To a solution of intermediate (2c) (0.758 g, 1.75 mmol) in ACN (32 mL) under argon atmosphere at −10° C. were successively added TEA (0.732 mL, 5.25 mmol) and a solution of diphosgene (0.275 mL, 2.28 mmol) in ACN (4.3 mL). After stirring for 30 min at −10° C., the mixture was evaporated under nitrogen flux. The residue was successively triturated with DCM and Et₂O. The residue was filtered off. The filtrate was evaporated to give intermediate (2d) which was used in the next step without further purification (0.866 g, 1.75 mmol, quantitative). MS m/z ([M+Na]⁺) 417.

Step 5: Preparation of Intermediate ethyl trans-4-allyloxy-2,5-methano-3-oxo-1,5-dihydrobenzothiopheno[2,3-e][1,3]diazepine-1-carboxylate (2e)

To a solution of intermediate (2d) (0.866 g, 1.75 mmol) in DCM (6 mL) under argon atmosphere at 0° C. was dropped HCl 4N in dioxane (17.5 mL, 70 mmol). After stirring for 1 h at 0° C. and for 1 h at rt, the mixture was evaporated under nitrogen flux. The residue was triturated with Et₂O to intermediate (2e) as a yellow oil (0.627 g, 1.75 mmol, quantitative). MS m/z ([M+H]⁺) 359. ¹H NMR (400 MHz, CDCl₃): δ (ppm) 1.35 (t, 3H), 3.67-3.70 (m, 1H), 4.02 (d, J=11.4 Hz, 1H), 4.27-5.35 (m, 2H), 4.40-4.54 (m, 3H), 5.28-5.38 (m, 3H), 5.94-6.08 (m, 1H), 7.32-7.39 (m, 2H), 7.75-7.81 (m, 2H).

Step 6: Preparation of Intermediate ethyl trans-4-hydroxy-2,5-methano-3-oxo-1,5-dihydrobenzothiopheno[2,3-e][1,3]diazepine-1-carboxylate (2f)

A solution of intermediate (2e) (0.250 g, 0.697 mmol) in DCM (15 mL) was degassed 10 min under argon atmosphere. AcOH (0.080 mL, 1.394 mmol) and Pd(PPh₃)₄ (0.403 g, 0.349 mmol) were successively added. After stirring for 30 min at rt, the mixture was evaporated under nitrogen flux. The residue was purified by column chromatography on silica gel (DCM/acetone 10/1 to 9/1). Fractions of interest are combined and concentrated. The residue was triturated with Et₂O to give intermediate (2f) as an orange solid (0.054 g, 0.167 mmol, 24%). MS m/z ([M+H]⁺) 319. ¹H NMR (300 MHz, acetone-d₆): δ (ppm) 1.32 (t, J=7.1 Hz, 3H), 3.66 (dd, J=3.0, 11.5 Hz, 1H), 3.95 (dd, J=0.3, 8.6 Hz, 1H), 4.30 (q, J=7.1 Hz, 2H), 4.69 (d, J=3.0 Hz, 1H), 5.29 (s, 1H), 7.45-7.36 (m, 2H), 7.81-7.85 (m, 1H), 7.94-7.97 (m, 1H), 8.89 (s, 1H).

Step 7: Preparation of sodium trans-(1-ethoxycarbonyl-2,5-methano-3-oxo-1,5-dihydrobenzothiopheno[2,3-e][1,3]diazepin-4-yl) sulfate, Example 2

To a solution of intermediate (2f) (0.044 g, 0.138 mmol) in anhydrous pyridine (1.5 mL) under inert atmosphere was added sulfur trioxide pyridine complex (0.132 g, 0.829 mmol). After stirring for 16 h, the mixture was concentrated in vacuum. DCM was added and the insoluble was filtered off. The filtrate was purified by flash chromatography on silica gel (DCM/acetone 10/0 to 0/10) to give Example 2 as pyridinium salt (0.074 g, 0.185 mmol). The sulfated product was applied on a Dowex sodium form column (Dowex® 50WX8 hydrogen form stored with an aqueous solution of 2N NaOH and washed until neutral pH with water). The fractions containing the desired compound were combined, frozen and lyophilized. The solid was triturated with DCM to give Example 2 as sodium salt (0.035 g, 0.083 mmol, 49%). MS m/z ([M+H]⁺) 399. ¹H NMR (400 MHz, D₂O): δ (ppm) 1.28 (t, J=7.1 Hz, 3H), 3.79 (d, J=11.9 Hz, 1H), 3.93 (dd, J=3.0, 11.9 Hz, 1H), 4.24-4.42 (m, 2H), 5.13 (d, J=3.0 Hz, 1H), 5.63 (s, 1H), 7.40-7.48 (m, 2H), 7.77-7.84 (m, 1H), 7.90-7.96 (m, 1H).

Example 3: synthesis of Sodium trans-(1-carbamoyl-2,5-methano-3-oxo-1,5-dihydrobenzothiopheno[2,3-e][1,3]diazepin-4-yl) sulfate

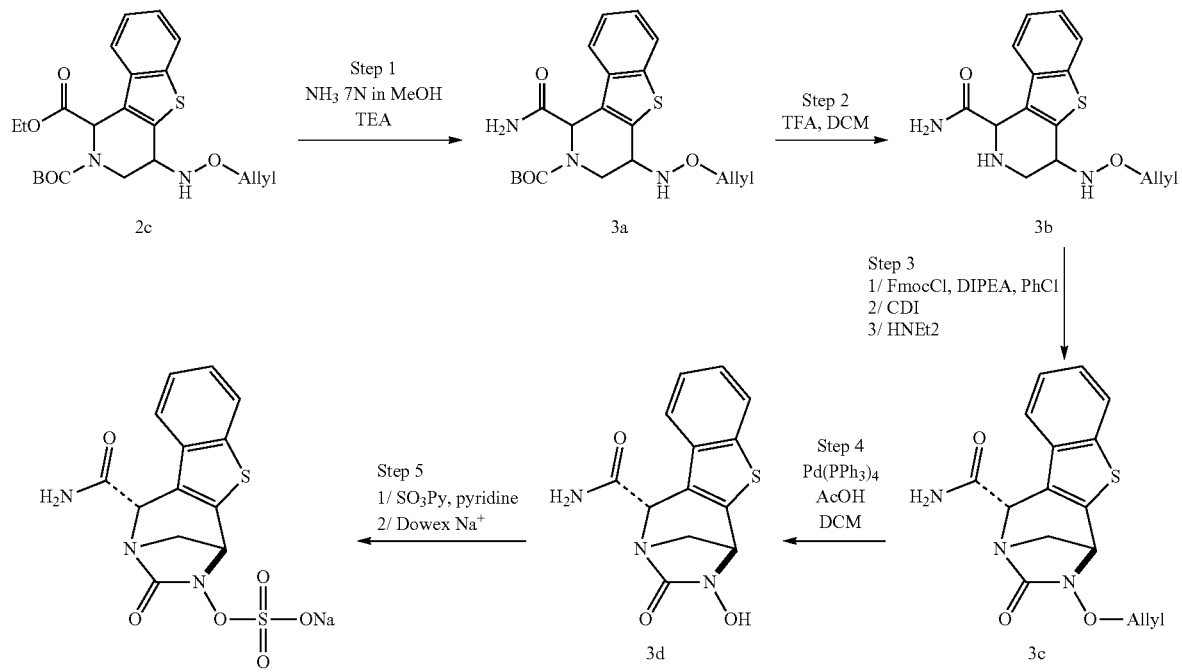

Step 1: Preparation of Intermediate tert-butyl 4-(allyloxyamino)-1-carbamoyl-3,4-dihydro-1H-benzothiopheno[3,2-c]pyridine-2-carboxylate (3a)

To a solution of intermediate (2c) (500 mg, 1.16 mmol) in MeOH (2 mL) was added $NH_3$ 7N in MeOH (15 mL, 105 mmol). After stirring for 18 h at 66° C., $NH_3$ aqueous 30% was added (4 mL) and the mixture was stirred for 6 days at 66° C. The solution was evaporated under nitrogen flux. The residue was diluted with DCM and washed with NaOH 1N. The organic layer was dried over $Na_2SO_4$, filtered and concentrated. The residue was purified by column chromatography on silica gel (DCM/acetone 10/0 to 9/1). The solid was triturated with $Et_2O$ to give intermediate (3a) as a mixture of both diastereoisomers (244 mg, 0.605 mmol, 52%). MS m/z ($[M+H]^+$) 404.

Step 2: Preparation of Intermediate 4-(allyloxyamino)-1,2,3,4-tetrahydrobenzothiopheno[3,2-c]pyridine-1-carboxamide (3b)

To a solution of intermediate (3a) (234 mg, 0.58 mmol) in DCM (6 mL) under argon atmosphere at 0° C. was dropped TFA (1.5 mL, 19.72 mmol). After stirring for 1 h at rt, the mixture was evaporated under nitrogen flux. The residue was purified by column chromatography on silica gel (DCM/MeOH 10/0 to 9/1) to give intermediate (3b) as a mixture of both diastereoisomers (249 mg, 0.821 mmol, quantitative). MS m/z ($[M+H]^+$) 304. $^1H$ NMR (400 MHz, $CDCl_3$): δ (ppm) 3.47-3.50 (m, 0.5H), 3.75-3.83 (m, 1.5H), 4.15 (t, J=5.4 Hz, 2H), 4.44-4.47 (m, 1H), 5.18 (d, J=9.6 Hz, 1H), 5.21-5.29 (m, 1H), 5.56 (d, J=15.7 Hz, 1H), 5.80-5.90 (m, 1H), 6.66 and 6.84 (2S, 1H), 7.31-7.45 (m, 2H), 7.62-7.76 (m, 1H), 7.79-7.87 (m, 1H).

Step 3: Preparation of Intermediate trans-4-allyloxy-2,5-methano-3-oxo-1,5-dihydrobenzothiopheno[2,3-e][1,3]diazepine-1-carboxamide (3c)

To a solution of intermediate (3b) (175 mg, 0.577 mmol) in chlorobenzene (1.6 mL) under argon atmosphere were successively added DIPEA (0.110 mL, 0.635 mmol) and a solution of Fmoc-Cl (151 mg, 0.582 mmol) in chlorobenzene (0.8 mL). After 1 h at rt, CDI (117 mg, 0.721 mmol) was added and the mixture was heated at 45° C. for 1 h. CDI was added and the mixture was heated at 45° C. until complete conversion. Then, the mixture was cold and $Et_2NH$ (0.240 mL, 2.31 mmol) was added. After 3 h at rt, the mixture was diluted with DCM. The organic layer was washed with HCl 1N and brine, dried over $Na_2SO_4$, filtered and concentrated. The residue was purified by column chromatography on silica gel (DCM/MeOH 10/0 to 9/1) to give intermediate (3c) (130 mg, 1.75 mmol, 22%). MS m/z ($[M+H]^+$) 330. $^1H$ NMR (400 MHz, $CDCl_3$): δ (ppm) 3.53 (d, J=11.1 Hz, 1H), 3.66 (dd, J=3.0, 11.1 Hz, 1H), 4.39-4.49 (m, 2H), 4.53 (d, J=2.7 Hz, 1H), 5.26 (s, 1H), 5.30-5.35 (m, 1H), 5.38 (dq, J=1.3, 17.3 Hz, 1H), 6.02 (ddt, J=6.3, 10.4, 16.9 Hz, 1H), 6.10 (bs, 1H), 6.94 (bs, 1H), 7.33 (dq, J=1.3, 7.1 Hz, 2H), 7.72-7.77 (m, 2H).

Step 4: Preparation of Intermediate trans-4-hydroxy-2,5-methano-3-oxo-1,5-dihydrobenzothiopheno[2,3-e][1,3]diazepine-1-carboxamide (3d)

A solution of intermediate (3c) (43 mg, 0.130 mmol) in DCM (2 mL) was degassed 10 min under argon atmosphere.

AcOH (0.015 mL, 0.26 mmol) and Pd(PPh$_3$)$_4$ (0.075 g, 0.065 mmol) were successively added. After stirring for 30 min at rt, the mixture was dried under nitrogen flux. The residue was purified by column chromatography on silica gel (DCM/acetone 10/0 to 0/10) to give intermediate (3d) (23 mg, 0.079 mmol, 60%). MS m/z ([M+H]$^+$) 290. $^1$H NMR (300 MHz, acetone-d$_6$): δ (ppm) 3.60 (dd, J=3.0, 11.2 Hz, 1H), 3.79 (d, J=11.2 Hz, 1H), 4.60 (d, J=3.0 Hz, 1H), 5.18 (s, 1H), 7.32-7.38 (m, 2H), 7.82-7.90 (m, 2H).

Step 5: Preparation of Sodium trans-(1-carbamoyl-2,5-methano-3-oxo-1,5-dihydrobenzothiopheno[2,3-e][1,3]diazepin-4-yl) sulfate, Example 3

To a solution of intermediate (3d) (23 mg, 0.079 mmol) in anhydrous pyridine (0.8 mL) under inert atmosphere was added sulfur trioxide pyridine complex (0.076 g, 0.476 mmol). After stirring for 18 h, the heterogeneous mixture was concentrated in vacuum. The residue was filtered and washed with DCM, acetone and IPA. The residue was solubilized with water and the aqueous solution was partially evaporated by nitrogen flux. The aqueous solution was applied on a Dowex sodium form column (Dowex® 50WX8 hydrogen form stored with an aqueous solution of 2N NaOH and washed until neutral pH with water). The fractions containing the desired compound were combined, frozen and lyophilized to give Example 3 as a white solid (0.011 g, 0.028 mmol, 35%). MS m/z ([M+H]$^+$) 370. MS m/z ([M−H]$^−$) 368. $^1$H NMR (400 MHz, D$_2$O): δ (ppm) 3.75 (d, J=11.9 Hz, 1H), 3.93 (dd, J=3.0, 11.9 Hz, 1H), 5.16 (d, J=2.6 Hz, 1H), 5.55 (s, 1H), 7.46-7.53 (m, 2H), 7.73-7.80 (m, 1H), 7.98-8.04 (m, 1H).

Example 4: Synthesis of sodium 1,4-methano-3-oxo-1,5-dihydro-[1,3]diazepino[5,6-b]quinolin-2-yl) sulfate Step 1: Preparation of Intermediate tert-butyl 4-oxo-1,3-dihydrobenzo[b][1,7]naphthyridine-2-carboxylate (4a)

A mixture of 2-nitrobenzaldehyde (600 mg, 3.97 mmol), N-Boc-piperidine-3,5-dione (1.01 g, 4.76 mmol) and iron (1.11 g, 19.85 mmol) in acetic acid (20 mL) was heated at 50° C. for 1 h. The mixture was concentrated in vacuo. The residue was dissolved in AcOEt and filtered over Celite®. The filtrate was carefully washed twice with a saturated solution of NaHCO$_3$. The organic layer was dried over Na$_2$SO$_4$, filtered and concentrated in vacuo. The residue was purified by flash chromatography on silica gel (Heptane/AcOEt 10/0 to 0/10) to provide intermediate (4a) as a yellow solid (448 mg, 1.50 mmol, 37%). MS m/z ([M+H]$^+$) 299. $^1$H NMR (400 MHz, CDCl$_3$): δ (ppm) 1.49 (s, 9H), 4.48 (s, 2H), 5.07 (s, 2H), 7.62 (ddd, J=1.2, 6.8, 8.1 Hz, 1H), 7.88 (ddd, J=1.5, 6.9, 8.5 Hz, 1H), 7.98 (d, J=8.0 Hz, 1H), 8.13 (d, J=8.6 Hz, 1H), 8.91 (s, 1H).

Step 2: Preparation of Intermediate tert-butyl 4-hydroxy-3,4-dihydro-1H-benzo[b][1,7]naphthyridine-2-carboxylate (4b)

To a solution of intermediate (4a) (445 mg, 1.49 mmol) in MeOH (5 mL) at 0° C. was portionwise added NaBH$_4$ (68 mg, 1.79 mmol). The reaction mixture was stirred for 45 min at 0° C., then hydrolyzed with water and concentrated in vacuo. The residue was solubilized in AcOEt. The layers were separated. The aqueous layer was extracted with AcOEt. The organic layers were combined, washed with brine, dried over Na$_2$SO$_4$, filtered and concentrated in vacuo to provide intermediate (4b) as a yellow foam (412 mg, 1.37 mmol, 91%). MS m/z ([M+H]$^+$) 301. $^1$H NMR (400 MHz, CDCl$_3$): δ (ppm) 1.51 (s, 9H), 3.77 (dd, J=6.4, 13.3 Hz, 1H),

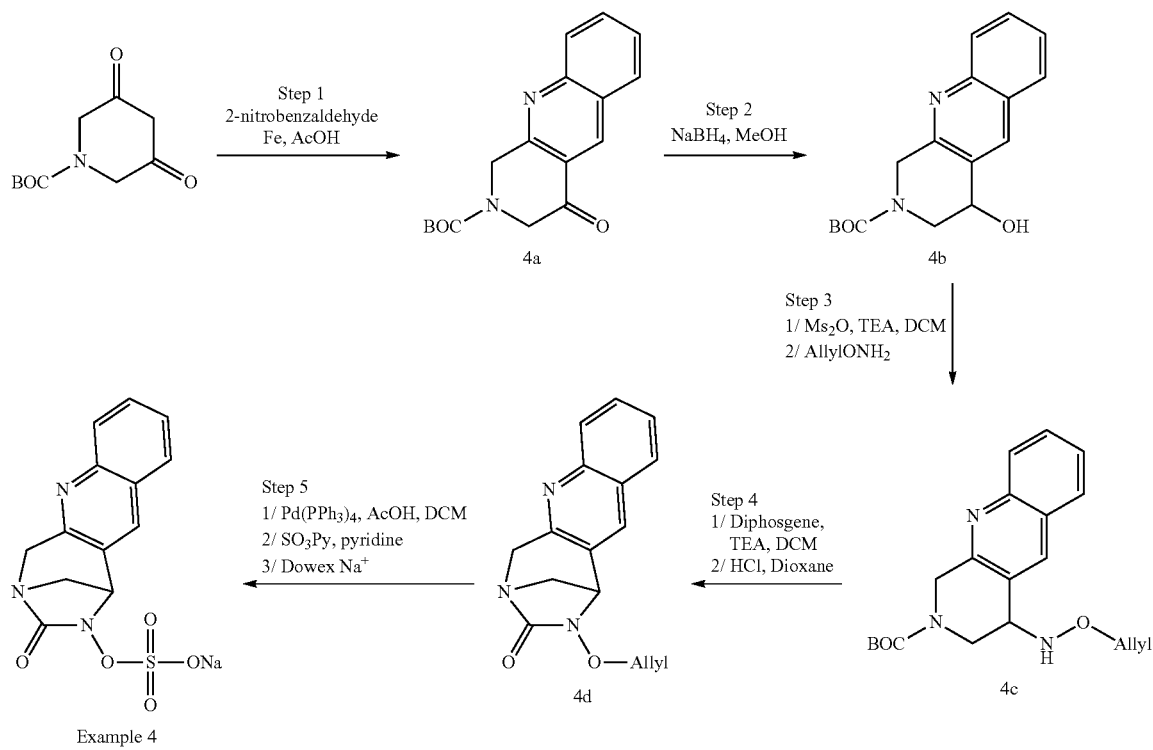

Example 4

3.94 (d, J=13.3 Hz, 1H), 4.78-5.08 (m, 3H), 7.53 (t, J=7.4 Hz, 1H), 7.72 (ddd, J=1.4, 6.8, 8.4 Hz, 1H), 7.83 (d, J=8.1 Hz, 1H), 8.05 (d, J=8.6 Hz, 1H), 8.34 (s, 1H).

Step 3: Preparation of Intermediate tert-butyl 4-(allyloxyamino)-3,4-dihydro-1H-benzo[b][1,7]naphthyridine-2-carboxylate (4c)

To a solution of intermediate (4b) (405 mg, 1.35 mmol) in DCM (5 mL) under inert atmosphere at −78° C. were successively added methanesulfonic anhydride (352 mg, 2.02 mmol) and TEA (0.552 mL, 3.96 mmol). The mixture was stirred at −78° C. for 90 min. A solution of 0-allylhydroxylamine 50% in DCM (985 mg, 6.74 mmol) was added and the mixture was stirred at rt overnight. Water was added and the layers were separated. The aqueous layer was extracted with DCM. The organic layers were combined, dried over Na$_2$SO$_4$, filtered and concentrated in vacuo. The residue was purified by flash chromatography on silica gel (heptane/AcOEt 10/0 to 0/10) to provide intermediate (4c) as a yellow oil (205 mg, 0.57 mmol, 42%). MS m/z ([M+H]$^+$) 356.

Step 4: Preparation of Intermediate 2-allyloxy-1,4-methano-1,5-dihydro-[1,3]diazepino[5,6-b]quinolin-3-one (4d)

To a solution of intermediate (4c) (200 mg, 0.563 mmol) in DCM (5 mL) at 0° C. were successively added TEA (118 µL, 0.844 mmol) and diphosgene (48 µL, 0.394 mmol). The mixture was stirred at 0° C. for 30 min before adding a saturated solution of NaHCO$_3$. The mixture was stirred for 5 min and the layers were separated. The aqueous layer was extracted with DCM. The organic layers were combined, dried over Na$_2$SO$_4$, filtered and concentrated in vacuo. The residue was dissolved in dioxane (1.5 mL) and a solution of hydrochloric acid 4N in dioxane (4 mL) was added. The mixture was stirred at rt for 50 min and concentrated in vacuo. The residue was solubilized in AcOEt (10 mL) and a saturated solution of NaHCO$_3$ (10 mL) was added. The aqueous layer was extracted with AcOEt. The organic layers were combined, dried over Na$_2$SO$_4$, filtered and concentrated in vacuo. The residue was purified by flash chromatography on silica gel (DCM/AcOEt 10/0 to 3/7) to provide intermediate (4d) as a yellow foam (102 mg, 0.362 mmol, 64%). MS m/z ([M+H]$^+$) 282. $^1$H NMR (400 MHz, CDCl$_3$): δ (ppm) 3.30 (d, J=11.3 Hz, 1H), 3.82 (ddd, J=1.3, 3.0, 11.4 Hz, 1H), 4.40-4.60 (m, 4H), 4.75 (dd, J=1.3, 17.8 Hz, 1H), 5.29-5.44 (m, 2H), 5.97-6.12 (m, 1H), 7.54 (ddd, J=1.2, 6.9, 8.1 Hz, 1H), 7.71 (ddd, J=1.5, 6.9, 8.5 Hz, 1H), 7.80 (dd, J=1.5, 8.2 Hz, 1H), 7.93 (s, 1H), 8.00 (d, J=8.5 Hz, 1H).

Step 5: Preparation of sodium 1,4-methano-3-oxo-1,5-dihydro-[1,3]diazepino[5,6-b]quinolin-2-yl) sulfate, Example 4

To a solution of intermediate (4d) (102 mg, 0.36 mmol) in anhydrous DCM (5 mL) under inert atmosphere were successively added AcOH (42 µL, 0.72 mmol) and Pd(PPh$_3$)$_4$ (210 mg, 0.18 mmol). After stirring at rt for 2 h, further Pd(PPh$_3$)$_4$ (105 mg, 0.09 mmol) was added and the stirring resumed for 1 h. Pyridine (3 mL) and sulfur trioxide-pyridine complex (289 mg, 1.81 mmol) were added. The mixture was stirred at rt overnight then concentrated in vacuo. DCM was added to the residue and the solids were filtered off. The filtrate was concentrated in vacuo. The crude was purified by flash chromatography on silica gel (DCM/acetone 10/0 to 0/10). The fractions containing the sulfated intermediate were combined and applied on a Dowex sodium form column (Dowex® 50WX8 hydrogen form stored with a 2N aqueous NaOH solution and washed until neutral pH with water). The fractions containing the desired compound were combined, frozen and lyophilized. The residue was purified by flash chromatography on C18 silica gel (water/ACN 10/0 to 0/10) to provide Example 4 as a white solid (38 mg, 0.11 mmol, 30%). MS m/z ([M+H]$^+$) 322. MS m/z ([M−H]$^-$) 320. $^1$H NMR (400 MHz, DMSO-d$_6$): δ (ppm) 3.51 (d, J=11.6 Hz, 1H), 3.67 (ddd, J=1.2, 3.1, 11.6 Hz, 1H), 4.33 (d, J=17.4 Hz, 1H), 4.57 (d, J=17.4 Hz, 1H), 4.95 (d, J=2.8 Hz, 1H), 7.60 (ddd, J=1.2, 6.8, 8.1 Hz, 1H), 7.75 (ddd, J=1.5, 6.9, 8.4 Hz, 1H), 7.93 (d, J=8.3 Hz, 1H), 8.03 (dd, J=1.2, 8.0 Hz, 1H), 8.13 (s, 1H).

Example 5: Synthesis of sodium (1,4-methano-3-oxo-1,5-dihydro-[1,3]diazepino[5,6-b][1,7]naphthyridin-2-yl) sulfate

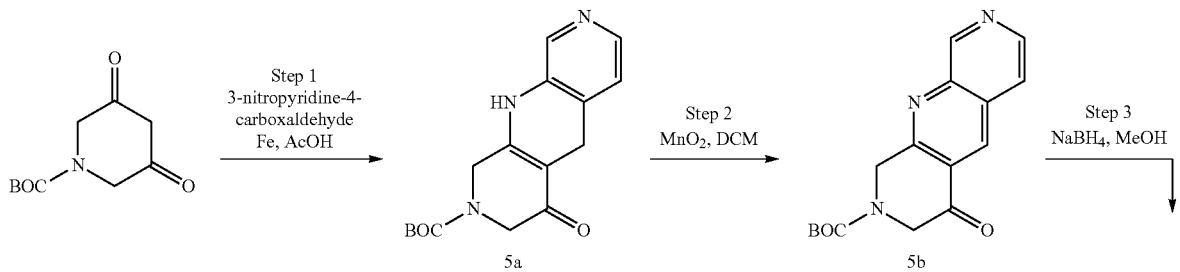

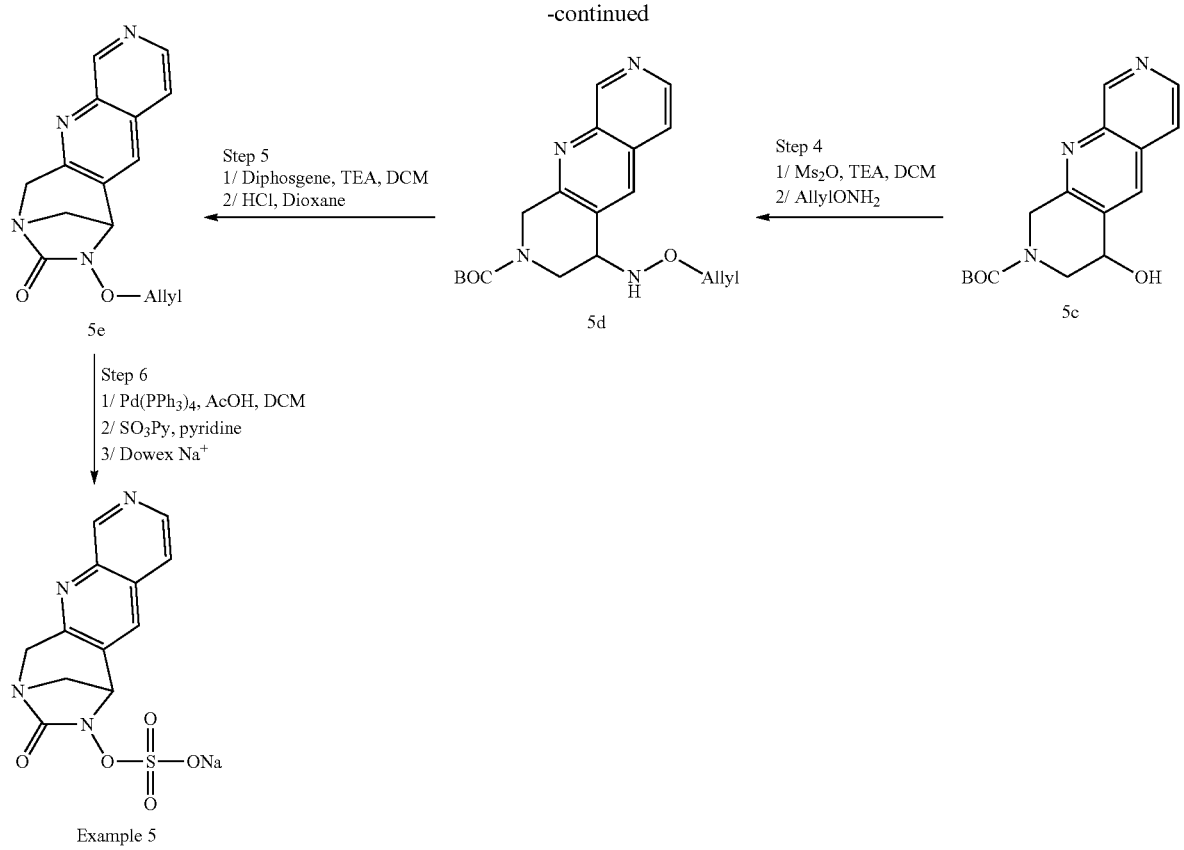

Example 5

Step 1: Preparation of Intermediate tert-butyl 4-oxo-1,3,5,10-tetrahydropyrido[3,4-b][1,7]naphthyridine-2-carboxylate (5a)

A mixture of 3-nitropyridine-4-carboxaldehyde (1.50 g, 9.86 mmol), N-Boc-piperidine-3,5-dione (2.52 g, 11.83 mmol) and iron (2.75 g, 49.3 mmol) in acetic acid (50 mL) was heated at 50° C. for 3 h. The mixture was concentrated in vacuo. The solution was co-evaporated twice with toluene. The residue was dissolved in AcOEt and a saturated solution of NaHCO$_3$. The mixture was filtered over Celite®. The layers of the filtrate was separated. The aqueous layer was extracted with AcOEt. The organic layers were combined, dried over Na$_2$SO$_4$, filtered and concentrated in vacuo. Acetone (20 mL) was added to the residue and the mixture refluxed for 30 min. The mixture was cooled at rt and filtrated to provide intermediate (5a) as an off-white solid (1.21 g, 4.01 mmol, 40%). MS m/z ([M+H]$^+$) 302. $^1$H NMR (400 MHz, DMSO-d$_6$): δ (ppm) 1.43 (s, 9H), 3.55 (s, 2H), 3.94 (s, 2H), 4.29 (s, 2H), 7.13 (d, J=4.9 Hz, 1H), 7.91-8.19 (m, 2H), 9.76 (s, 1H).

Step 2: Preparation of Intermediate tert-butyl 4-oxo-1,3-dihydropyrido[3,4-b][1,7]naphthyridine-2-carboxylate (5b)

To a suspension of intermediate (5a) (1.20 g, 3.98 mmol) in DCM (80 mL) at rt was added activated manganese dioxide (3.16 g, 35.8 mmol) in three portions every 20 min. The mixture was stirred at rt for 20 min then filtered over a pad of Celite®. The filtrate was concentrated in vacuo. The residue was purified by flash chromatography on silica gel (DCM/AcOEt 10/0 to 2/8) to provide intermediate (5b) as a yellow solid (645 mg, 2.15 mmol). MS m/z ([M+H]$^+$) 300. $^1$H NMR (400 MHz, DMSO-d$_6$): δ (ppm) 1.41 (s, 9H), 4.48 (s, 2H), 5.01 (s, 2H), 8.14 (dd, J=1.0, 5.6 Hz, 1H), 8.71 (d, J=5.6 Hz, 1H), 9.05 (d, J=0.9 Hz, 1H), 9.48 (s, 1H).

Step 3: Preparation of Intermediate tert-butyl 4-hydroxy-3,4-dihydro-1H-pyrido[3,4-b][1,7]naphthyridine-2-carboxylate (5c)

Using the procedure described in example 4 (step 2), intermediate (5b) (543 mg, 1.81 mmol) was converted into intermediate (5c) as a pale yellow solid (497 mg, 1.65 mmol, 90%) which was used without purification. MS m/z ([M+H]$^+$) 302. $^1$H NMR (400 MHz, Acetone-d$_6$): δ (ppm) 1.50 (s, 9H), 3.27-3.58 (m, 1H), 4.16 (bs, 1H), 4.73 (d, J=18.2 Hz, 1H), 4.84-5.18 (m, 3H), 7.84 (dd, J=1.0, 5.6 Hz, 1H), 8.47 (s, 1H), 8.56 (d, J=5.6 Hz, 1H), 9.30 (d, J=1.0 Hz, 1H).

Step 4: Preparation of Intermediate tert-butyl 4-(allyloxyamino)-3,4-dihydro-1H-benzo[b][1,7]naphthyridine-2-carboxylate (5d)

To a solution of intermediate (5c) (250 mg, 0.83 mmol) in DCM (10 mL) under inert atmosphere at −20° C. were successively added methanesulfonic anhydride (217 mg, 1.24 mmol) and TEA (0.226 mL, 1.66 mmol). The mixture was stirred at −20° C. for 20 min. Water was added. The layers were separated. The aqueous layer was extracted with DCM. The organic layers were combined, dried over Na$_2$SO$_4$, filtered and concentrated in vacuo. A solution of 0-allylhydroxyamine 50% in DCM (1.21 g, 8.3 mmol) was added to the residue and the mixture was heated at 40° C. for 30 min. The mixture was diluted with DCM and washed with a saturated solution of NaHCO$_3$. The organic layer was dried over Na$_2$SO$_4$, filtered and concentrated in vacuo. The residue was purified by flash chromatography on silica gel (DCM/AcOEt 10/0 to 0/10) to provide intermediate (5d) as a yellow oil (158 mg, 0.44 mmol, 53%). MS m/z ([M+H]$^+$) 357. 1H NMR (400 MHz, CDCl$_3$): δ (ppm) 1.49 (s, 9H), 3.44-3.59 (m, 1H), 4.14-4.44 (m, 4H), 4.67 (d, J=18.3 Hz, 1H), 5.01-5.20 (m, 2H), 5.24 (d, J=17.3 Hz, 1H), 5.66 (bs, 1H), 5.81-5.97 (m, 1H), 7.61 (d, J=5.6 Hz, 1H), 8.21 (s, 1H), 8.55 (d, J=5.6 Hz, 1H), 9.40 (s, 1H).

Step 5: Preparation of Intermediate 2-allyloxy-1,4-methano-1,5-dihydro-[1,3]diazepino[5,6-b][1,7]naphthyridin-3-one (5e)

To a solution of intermediate (5d) (158 mg, 0.443 mmol) in DCM (5 mL) at 0° C. were successively added TEA (93 μL, 0.664 mmol) and diphosgene (37 μL, 0.31 mmol). The mixture was stirred at 0° C. for 30 min before adding a saturated solution of NaHCO$_3$. The mixture was stirred for 5 min and the layers were separated. The aqueous layer was extracted with DCM. The organic layers were combined, dried over Na$_2$SO$_4$, filtered and concentrated in vacuo. The residue was dissolved in DCM (3 mL) and TFA (1 mL) was added. The mixture was stirred at rt for 3 h then concentrated in vacuo. The residue was solubilized in AcOEt (10 mL) and a saturated solution of NaHCO$_3$ (10 mL) was added. The aqueous layer was extracted with AcOEt. The organic layers were combined, dried over Na$_2$SO$_4$, filtered and concentrated in vacuo. The residue was purified by flash chromatography on silica gel (DCM/acetone 10/0 to 0/10) to provide intermediate (5e) as an orange oil (13 mg, 0.046 mmol, 10%). MS m/z ([M+H]$^+$) 283. $^1$H NMR (400 MHz, CDCl$_3$): δ (ppm) 3.30 (d, J=11.5 Hz, 1H), 3.84 (ddd, J=1.3, 3.0, 11.6 Hz, 1H), 4.40-4.51 (m, 2H), 4.54 (d, J=18.0 Hz, 1H), 4.59 (d, J=2.9 Hz, 1H), 4.74 (dd, J=1.2, 18.0 Hz, 1H), 5.30-5.43 (m, 2H), 5.96-6.09 (m, 1H), 7.64 (dd, J=0.8, 5.6 Hz, 1H), 7.92 (s, 1H), 8.61 (d, J=5.6 Hz, 1H), 9.39 (s, 1H).

Step 6: Preparation of sodium (1,4-methano-3-oxo-1,5-dihydro-[1,3]diazepino[5,6-b][1,7]naphthyridin-2-yl) sulfate, Example 5

To a solution of intermediate (5e) (13 mg, 0.046 mmol) in anhydrous DCM (1 mL) under inert atmosphere were successively added AcOH (5 μL, 0.092 mmol) and Pd(PPh$_3$)$_4$ (27 mg, 0.023 mmol). After stirring at rt for 30 min, further Pd(PPh$_3$)$_4$ (27 mg, 0.023 mmol) and AcOH (5 μL, 0.092 mmol) were added. The stirring resumed for 1 h. The precipitate was filtered and solubilized in pyridine (0.7 mL) before adding sulfur trioxide-pyridine complex (37 mg, 0.23 mmol). The mixture was stirred at rt for 4 h then concentrated in vacuo. DCM was added to the residue and the solids were filtered off. The filtrate was concentrated in vacuo. The crude was applied on a Dowex sodium form column (Dowex® 50WX8 hydrogen form stored with a 2N aqueous NaOH solution and washed until neutral pH with water). The fractions containing the desired compound were combined, frozen and lyophilized. The residue was purified by flash chromatography on C18 silica gel (water/ACN 99/1 to 10/90) to provide Example 5 as a white solid (1.5 mg, 0.0043 mmol, 9%). MS m/z ([M−H]$^-$) 321. $^1$H NMR (400 MHz, D$_2$O): δ (ppm) 3.69 (d, J=12.0 Hz, 1H), 4.03 (ddd, J=1.3, 3.1, 12.0 Hz, 1H), 4.65 (d, J=17.9 Hz, 1H), 4.77 (d, J=17.9 Hz, 1H), 5.21 (d, J=3.0 Hz, 1H), 7.82 (dd, J=0.8, 5.7 Hz, 1H), 8.33 (s, 1H), 8.48 (d, J=5.7 Hz, 1H), 9.14 (s, 1H).

Example 6: Synthesis of sodium [trans-1-ethoxycarbonyl-2,5-methano-6-methyl-3-oxo-1,5-dihydro-[1,3]diazepino[5,6-b]indol-4-yl] sulfate

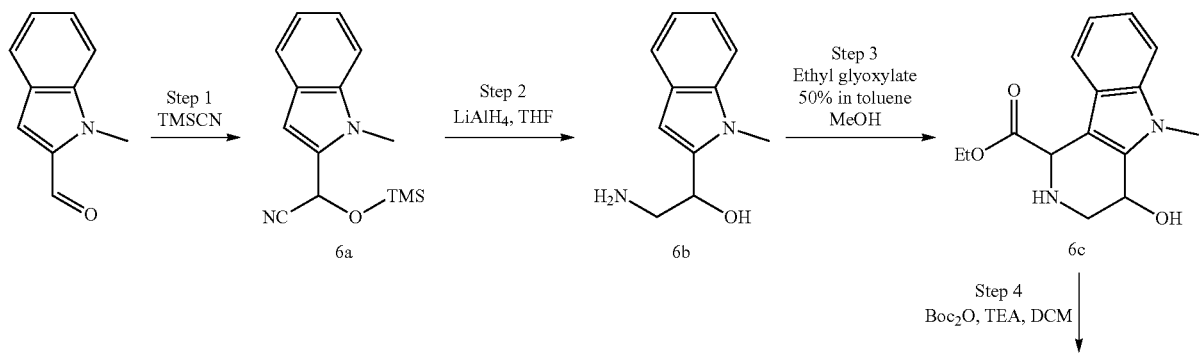

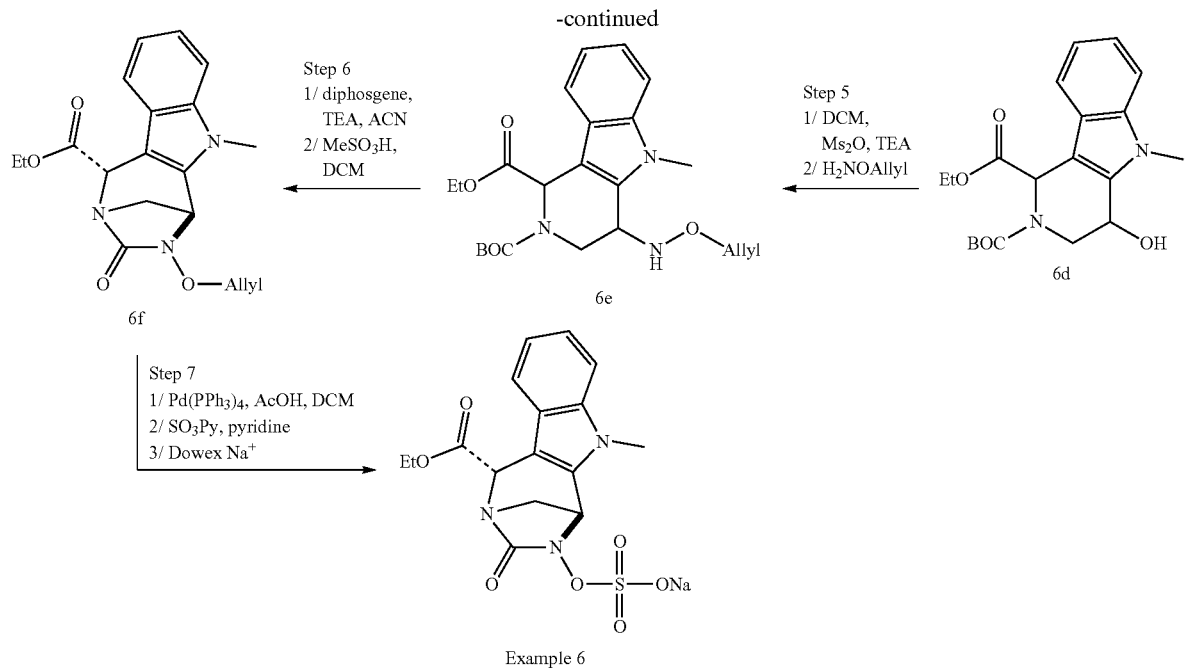

Example 6

Step 1: Preparation of Intermediate 2-(1-methylindol-2-yl)-2-trimethylsilyloxy-acetonitrile In a sealed tube, TMSCN (4 mL) was added to 1-methylindole-2-carbaldehyde (1.25 g, 7.85 mmol) and mixture was stirred at 80° C. for 48 h. The mixture was concentrated to give crude intermediate (6a) which was used without purification in the next step. MS m/z ([M+H]$^+$) 259.

Step 2: Preparation of Intermediate 2-amino-1-(1-methylindol-2-yl)ethanol (6b)

At 0° C., a solution of LiAlH$_4$ 2M in THF (7.85 mL, 15.7 mmol) was added dropwise to a solution of intermediate (6a) (7.85 mmol) in THF (5 mL) and the mixture was stirred at rt for 2 h. At 0° C., the mixture was quenched by addition of AcOEt (1 mL), water (0.6 mL), NaOH 10% (0.9 mL), and water (1.8 mL). After 15 min of stirring, solids were filtered off and washed with AcOEt. The filtrate was concentrated and the residue was triturated with DCM. The solid was filtered and dried under vacuum to give intermediate (6b) (890 mg, 4.68 mmol, 60% on 2 steps). MS m/z ([M−OH]$^+$) 173. $^1$H NMR (400 MHz, DMSO-d$_6$): δ (ppm) 1.50 (bs, 2H), 2.82-2.96 (m, 2H), 3.76 (s, 3H), 4.65 (t, J=6.3 Hz, 1H), 5.31 (bs, 1H), 6.34 (s, 1H), 6.99 (ddd, J=1.0, 7.0, 7.9 Hz, 1H), 7.10 (ddd, J=1.2, 7.0, 8.3 Hz, 1H), 7.40 (dd, J=1.0, 8.2 Hz, 1H), 7.48 (d, J=7.8 Hz, 1H).

Step 3: Preparation of Intermediate ethyl 4-hydroxy-5-methyl-1,2,3,4-tetrahydropyrido[4,3-b]indole-1-carboxylate (6c)

A solution of Ethyl glyoxylate 50% in Toluene (1.04 mL, 5.26 mmol) was added to a solution of intermediate (6b) (1.0 g, 5.26 mmol) in MeOH (5.2 mL). The mixture was stirred at rt for 18 h. The precipitate was filtered, washed with MeOH and dried under vacuum to give intermediate (6c) as a white solid (820 mg, 2.99 mmol, 57%, mixture of both diastereoisomers). MS m/z ([M+H]$^+$) 275. $^1$H NMR (400 MHz, DMSO-d$_6$): δ (ppm) 1.24 (t, J=7.1 Hz, 3H), 2.70 (bs, 1H), 3.03 (dd, J=4.4, 13.2 Hz, 1H), 3.15 (dd, J=4.5, 13.3 Hz, 1H), 3.76 (s, 3H), 4.10-4.24 (m, 2H), 4.64 (s, 1H), 4.65-4.72 (m, 1H), 5.41 (d, J=6.5 Hz, 1H), 6.98-7.05 (m, 1H), 7.11-7.17 (m, 1H), 7.43 (d, J=8.2 Hz, 1H), 7.53 (d, J=8.0 Hz, 1H).

Step 4: Preparation of Intermediate O2-tert-butyl O1-ethyl 4-hydroxy-5-methyl-3,4-dihydro-1H-pyrido[4,3-b]indole-1,2-dicarboxylate (6d)

TEA (0.84 mL, 5.98 mmol) and Boc$_2$O (652 mg, 2.99 mmol) were added to a solution of intermediate (6c) (820 mg, 2.99 mmol) in DCM (15 mL). After stirring for 2 h at rt, the mixture was diluted with DCM and washed with H$_2$O and brine. The organic layer was dried over Na$_2$SO$_4$, filtered and concentrated in vacuo. The crude product was purified by column chromatography on silica gel (DCM/Acetone: 10/0 to 6/4) to give intermediate (6d) (1.06 g, 2.83 mmol, 95%, mixture of both diastereoisomers). MS m/z ([M-OH]$^+$) 357. $^1$H NMR (400 MHz, CDCl$_3$): δ (ppm) 1.23 (t, J=7.1 Hz, 3H), 1.51 (s, 9H), 3.59-3.68 (m, 1H), 3.82 (s, 3H), 4.08-4.20 (m, 2H), 4.24-4.42 (m, 1H), 4.91-5.01 (m, 1H), 5.57-5.69 (m, 1H), 7.13-7.19 (m, 1H), 7.24-7.30 (m, 1H), 7.34 (d, J=8.3 Hz, 1H), 7.73 (d, J=8.0 Hz, 1H).

Step 5: Preparation of Intermediate O2-tert-butyl O1-ethyl 4-(allyloxyamino)-5-methyl-3,4-dihydro-1H-pyrido[4,3-b]indole-1,2-dicarboxylate (6e)

At −78° C., a solution of Ms$_2$O (700 mg, 4.02 mmol) in DCM (4 mL) was slowly added to a solution of TEA (0.75 mL, 5.36 mmol) and intermediate (6d) (500 mg, 1.34 mmol) in DCM (16 mL). The mixture was stirred for 45 min at −78° C. A solution of O-allylhydroxylamine (683 mg, 9.36 mmol) in DCM (4 mL) was then added. The mixture was slowly warmed to rt for 1 h. The mixture was diluted with DCM and washed with H$_2$O and brine. The organic layer was dried over Na$_2$SO$_4$, filtered and concentrated in vacuo. The crude product was purified by column chromatography on silica gel (DCM/Acetone: 10/0 to 8/2) to give intermediate (6e) (530 mg, 1.24 mmol, 93%, mixture of both diastereoisomers). MS m/z ([M+H]$^+$) 430.

Step 6: Preparation of Intermediate ethyl trans-4-allyloxy-2,5-methano-6-methyl-3-oxo-1,5-dihydro-[1,3]diazepino[5,6-b]indole-1-carboxylate (6f)

At 0° C., diphosgene (157 µL, 1.3 mmol) was added to a solution of TEA (279 µL, 2.0 mmol) and intermediate (6e) (430 mg, 1.0 mmol) in DCM (5 mL). The mixture was stirred at 0° C. for 45 min then a solution of MeSO$_3$H (973 µL, 15.0 mmol) in DCM (5 mL) was added. After 1 h at 0° C., TEA (6.95 mL, 50 mmol) was added and mixture was stirred at 70° C. for 18 h. The mixture was diluted with DCM and washed with H$_2$O and brine. The organic layer was dried over Na$_2$SO$_4$, filtered and concentrated in vacuo. The crude product was purified by column chromatography on silica gel (DCM/Acetone: 10/0 to 8/2) to give intermediate (6f) (252 mg, 0.71 mmol, 71%). MS m/z ([M+H]$^+$) 356. $^1$H NMR (400 MHz, CDCl$_3$): δ (ppm) 1.35 (t, J=7.1 Hz, 3H), 3.73 (s, 3H), 3.73-3.78 (m, 2H), 3.92 (d, J=11.4 Hz, 1H), 4.20-4.38 (m, 2H), 4.39-4.52 (m, 2H), 4.64 (d, J=2.5 Hz, 1H), 5.30-5.34 (m, 1H), 5.34-5.41 (m, 1H), 5.97-6.09 (m, 1H), 7.12 (ddd, J=1.1, 7.0, 8.0 Hz, 1H), 7.23 (ddd, J=1.2, 6.9, 8.3 Hz, 1H), 7.28-7.32 (m, 1H), 7.66-7.70 (m, 1H).

Step 7: Preparation of sodium [trans-1-ethoxycarbonyl-2,5-methano-6-methyl-3-oxo-1,5-dihydro-[1,3]diazepino[5,6-b]indol-4-yl] sulfate, Example 6

AcOH (15 µL, 0.25 mmol) and Pd(PPh$_3$)$_4$ (72 mg, 0.06 mmol) were successively added to a solution of intermediate (6f) (44 mg, 0.12 mmol) in anhydrous DCM (1.2 mL). After 2 h at rt, further AcOH (15 µL, 0.25 mmol) and Pd(PPh$_3$)$_4$ (72 mg, 0.06 mmol) were added and mixture was stirred for 18 h. Mixture was evaporated under flux of nitrogen. The residue was purified by flash chromatography on silica gel (DCM/acetone 10/0 to 6/4) to give the de-allylated intermediate (16 mg). Pyridine (1 mL) and sulfur trioxide pyridine complex (45 mg, 0.28 mmol) were added to the de-allylated intermediate and mixture was stirred at rt for 3 h. The mixture was diluted with DCM and the solids were filtered off. The filtrate was concentrated and the residue was purified by flash chromatography on silica gel (DCM/acetone 10/0 to 0/10). Desired fractions were concentrated in vacuo and residue was applied on a Dowex sodium form column (Dowex® 50WX8 hydrogen form stored with an aqueous solution of 2N NaOH and washed until neutral pH with water). The fractions containing the desired compound were combined, frozen and lyophilized to provide Example 6 as sodium salt (12 mg, 0.029 mmol, 24%). MS m/z ([M-H]$^-$) 394. $^1$H NMR (400 MHz, D$_2$O): δ (ppm) 1.33 (t, J=6.1 Hz, 3H), 3.75-3.77 (m, 1H), 3.82 (s, 3H), 3.95-3.97 (m, 1H), 4.25-4.45 (m, 2H), 5.32 (s, 1H), 5.61 (s, 1H), 7.25 (t, J=6.7 Hz, 1H), 7.37 (t, J=6.7 Hz, 1H), 7.56 (d, J=8.1 Hz, 1H), 7.77 (d, J=7.8 Hz, 1H).

Example 7: Synthesis of sodium [9-(diethylcarbamoyl)-2,5-methano-3-oxo-5,7,8,10-tetrahydro-1H-pyrido[3,4]thieno[1,3-d][1,3]diazepin-4-yl] sulfate

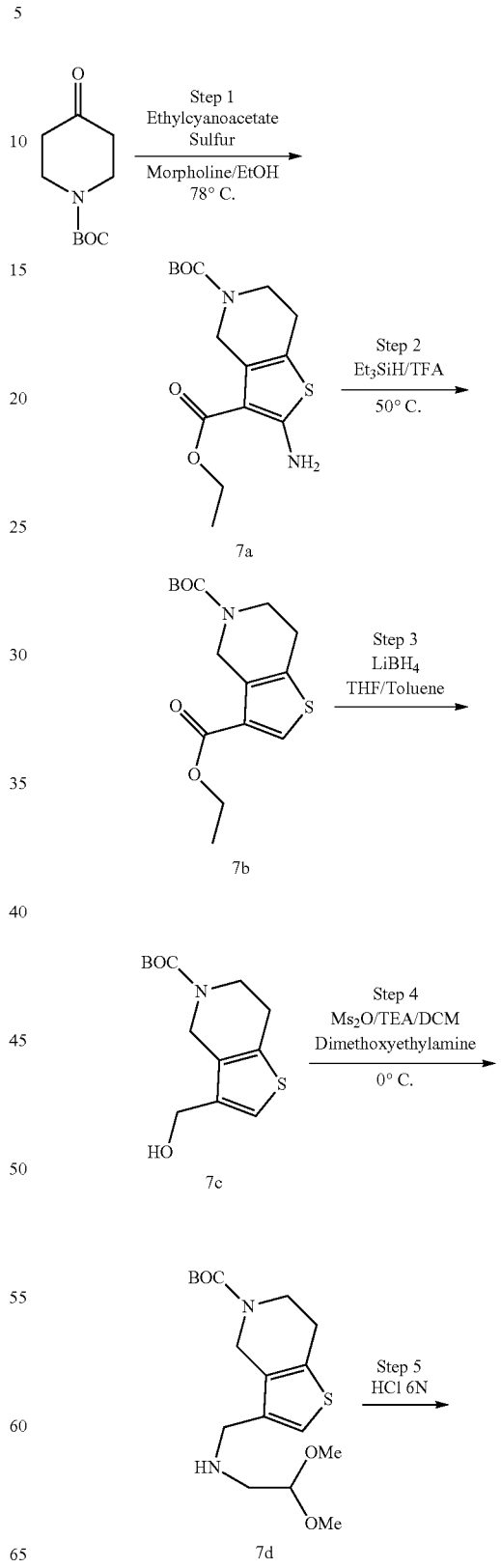

-continued

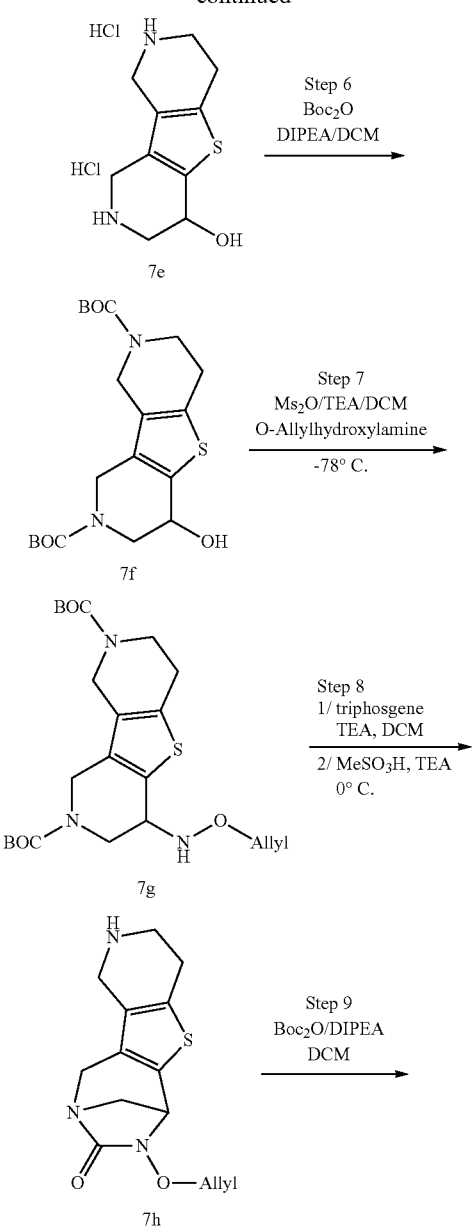

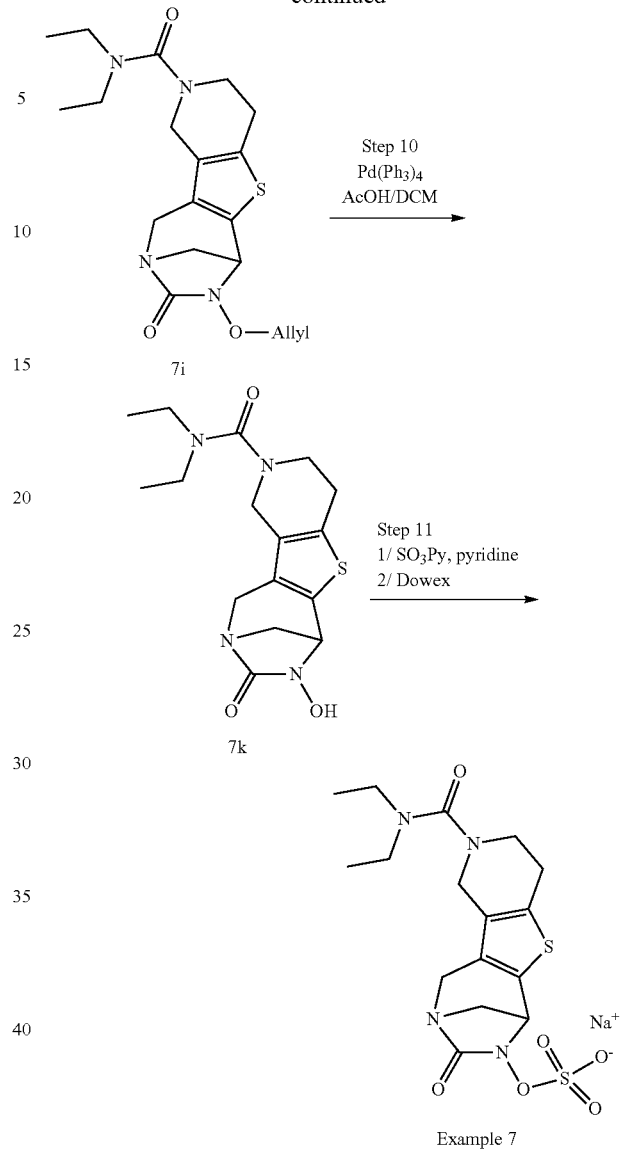

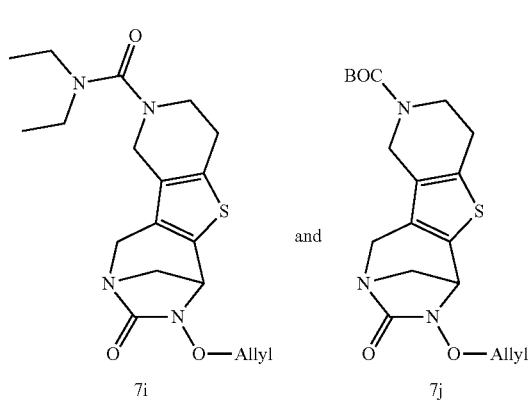

Step 1: Preparation of Intermediate O5-tert-butyl O3-ethyl 2-amino-6,7-dihydro-4H-thieno[3,2-c]pyridine-3,5-dicarboxylate (7a)

To a solution of N-tert-butoxycarbonyl-4-piperidone (1.0 g, 5.02 mmol) and ethylcyanoacetate (0.53 mL, 5.02 mmol) in absolute ethanol (25 mL) was added sulfur powder (160 mg, 5.02 mmol) and morpholine (437 mg, 5.02 mmol). The mixture was refluxed for 1 hour and then concentrated under reduced pressure to give intermediate 7a as yellow solid (1.60 g, 5.02 mmol, 100%) which was used without further purification. MS m/z ([M+H]$^+$) 327. $^1$H NMR (400 MHz, CDCl$_3$) δ (ppm): 1.33 (t, J=7.1 Hz, 3H), 1.47 (s, 9H), 2.80 (t, J=5.9 Hz, 2H), 3.61 (t, J=5.9 Hz, 2H), 4.26 (q, J=7.1 Hz, 2H), 4.35 (bs, 2H), 6.01 (bs, 2H).

Step 2: Preparation of Intermediate O5-tert-butyl O3-ethyl 6,7-dihydro-4H-thieno[3,2-c]pyridine-3,5-dicarboxylate (7b)

At 0° C., isoamyl nitrite (1.49 mL, 11.06 mmol) was added dropwise to a solution of intermediate (7a) (1.6 g, 5.02 mmol) in THF (8 mL). The mixture was then refluxed for 2 h, cooled to room temperature and concentrated under reduced pressure. The crude was purified by column chromatography on silica gel (petroleum ether/EtOAc: 10/1) to give intermediate (7b) as yellow powder (140 mg, 0.45 mmol, 10%). MS m/z ([M+Na]$^+$) 334. $^1$H NMR (400 MHz, CDCl$_3$) δ (ppm): 1.35 (m, J=7.1 Hz, 3H), 1.48 (s, 9H), 2.98 (t, J=5.9 Hz, 2H), 3.66 (t, J=5.8 Hz, 2H), 4.29 (q, J=7.1 Hz, 2H), 4.60 (s, 2H), 7.97 (s, 1H).

Step 3: Preparation of Intermediate tert-butyl 3-(hydroxymethyl)-6,7-dihydro-4H-thieno[3,2-c]pyridine-5-carboxylate (7c)

A suspension of intermediate (7b) (140 mg, 0.45 mmol) and lithium borohydride (40 mg, 1.8 mmol) in THF (0.5 mL) and toluene (1 mL) was heated at 100° C. for 1 h. The mixture was then cooled to room temperature and concentrated. The crude was purified by column chromatography on silica gel (heptane/ethyl acetate: 1/1) to give intermediate (7c) as colorless oil (90 mg, 0.33 mmol, 75%). MS m/z ([M+Na]$^+$) 292.

Step 4: Preparation of Intermediate tert-butyl 3-[(2,2-dimethoxyethylamino)methyl]-6,7-dihydro-4H-thieno[3,2-c]pyridine-5-carboxylate (7d)

At 0° C., to a solution of intermediate (7c) (900 mg, 3.66 mmol) in DCM (20 mL) were successively added TEA (1.5 mL, 10.98 mmol) and methanesulfonic anhydride (1.27 g, 7.33 mmol). The mixture was stirred 2 h at 0° C. Then, a solution of dimethoxyethylamine (2.4 mL, 21.96 mmol) in DCM (30 mL) was added dropwise. The mixture was stirred for 30 minutes then 16 h at rt. The mixture was diluted with DCM, washed with water and extracted twice with DCM. Organics were dried over Na$_2$SO$_4$, filtered and concentrated. The crude product was purified by column chromatography on silica gel (DCM/MeOH: 1/1) to give intermediate (7d) (0.84 g, 2.36 mmol, 64%). MS m/z ([M+H]$^+$) 357.

Step 5: Preparation of Intermediate 2-hydroxy-2,3,4,5,6,7,8,9-octahydrothieno[3,2-c:4,5-c]dipyridinium dihydrochloride (7e)

A solution of intermediate (7d) (0.840 g, 2.36 mmol) in HCl 6N (15 mL) was stirred for 1 h30 at 60° C. The mixture was concentrated to give intermediate (7e) (1.02 g) which was used without further purification. MS m/z ([M+H]$^+$) 211.

Step 6: Preparation of Intermediate 4,7-di-tert-butyl 2-hydroxy-2,3,8,9-tetrahydro-5,6H-thieno[3,2-c:4,5-c]dipyridine-4,7-dicarboxylate (7f)

To a solution of intermediate (7e) (1.02 g, 2.36 mmol) in DCM (40 mL) under argon atmosphere were successively added Boc$_2$O (2.7 g, 12.75 mmol) and DIPEA (4.95 mL, 28.32 mmol). After stirring for 2 days at rt, the mixture was concentrated. The residue was purified by column chromatography on silica gel (heptane/EtOAc: 1/1) to give intermediate (7f) as colorless oil (0.30 g, 0.73 mmol, 31%). MS m/z=([M+Na$^+$]) 433.

Step 7: Preparation of Intermediate 4,7-di-tert-butyl 2-(N-allyloxy)-2,3,8,9-tetrahydro-5,6H-thieno[3,2-c:4,5-c]dipyridine-4,7-dicarboxylate (7 g)

At −78° C., methanesulfonic anhydride (0.382 g, 2.19 mmol) was added to a solution of intermediate (7f) (0.30 g, 0.73 mmol) and TEA (0.408 mL, 2.92 mmol) in DCM (2 mL). After stirring for 1 h20 at −78° C., 0-allylhydroxylamine (0.534 g, 7.3 mmol) in DCM (2 mL) was added dropwise. The mixture was stirred for 20 min at −78° C. then 1 h at rt. The mixture was diluted with DCM, washed twice with water, dried over Na$_2$SO$_4$, filtered and concentrated. The crude was purified by column chromatography on silica gel (Heptane/EtOAc: 1/1) to give intermediate (7 g) (0.15 g, 0.32 mmol, 44%). MS m/z ([M+H]$^+$) 466.

Step 8: Preparation of 4-allyloxy-2,5-methano-1,5,7,8,9,10-hexahydropyrido[2,3]thieno[2,4-d][1,3]diazepin-3-one (7 h)

To a solution of intermediate (7 g) (0.15 g, 0.32 mmol) in DCM (2.5 mL) were successively added TEA (0.44 mL, 1.18 mmol) and triphosgene (49 mg, 0.46 mmol). The mixture was stirred for 5 min at rt. The mixture was cooled to 0° C. and methanesulfonic acid (0.62 mL, 3.9 mmol) was then added. The mixture was stirred for 1 h at rt. The mixture was cooled to 0° C. and TEA (0.73 mL, 1.95 mmol) was added. The mixture was stirred at rt for 1 h. The mixture was then diluted with DCM, washed with aq. NaHCO$_3$, dried over Na$_2$SO$_4$, filtered and concentrated. The crude was purified by column chromatography on silica gel (DCM/Acetone: 9/1) to give intermediate (7 h) as white powder (0.09 g, 0.31 mmol, 72%). MS m/z ([M+H]$^+$) 292.
$^1$H NMR (400 MHz, DMSO-d$_6$) δ (ppm): 2.98 (t, J=6.1 Hz, 2H), 3.14 (q, J=7.0 Hz, 1H), 3.25 (d, J=11.0 Hz, 1H), 3.40 (dt, J=5.7, 12.0 Hz, 1H), 3.54 (td, J=3.0, 11.2 Hz, 1H), 3.88-4.13 (m, 2H), 4.13-4.25 (m, 2H), 4.38 (d, J=6.0 Hz, 2H), 4.70-4.77 (m, 1H), 5.25 (dq, J=11.3, 10.5 Hz, 1H), 5.34 (dq, J=1.6, 17.3 Hz, 1H), 5.87-5.98 (m, 1H), 9.05 (bs, 1H).

Step 9: Preparation of Intermediates 4-allyloxy-N,N-diethyl-2,5-methano-3-oxo-5,7,8,10-tetrahydro-1H-pyrido[3,4]thieno[1,3-d][1,3]diazepine-9-carboxamide (7i) and tert-butyl 4-allyloxy-2,5-methano-3-oxo-5,7,8,10-tetrahydro-1H-pyrido[3,4]thieno[1,3-d][1,3]diazepine-9-carboxylate (7j)

To a solution of intermediate (7 h) (90 mg, 0.3 mmol) in DCM (4 mL) were successively added Boc$_2$O (120 mg, 0.55 mmol) and DIPEA (0.21 mL, 1.2 mmol). After stirring for 12 h at rt, the mixture was diluted with DCM. Organics were washed with water, dried over Na$_2$SO$_4$, filtered and concentrated. The residue was purified by column chromatography on silica gel (DCM/Acetone: 95/5) to intermediates (7i) (0.05 g, 0.13 mmol, 42%) and (7j) (0.04 g, 0.10 mmol, 34%).
Intermediate (7i): MS m/z ([M+H]$^+$) 391; $^1$H NMR (400 MHz, CDCl$_3$) δ (ppm): 1.13 (t, J=7.1 Hz, 6H), 2.84 (dtt, J=1.9, 3.9, 5.9 Hz, 2H), 3.16-3.27 (m, 5H), 3.37-3.54 (m, 2H), 3.71 (dd, J=3.1, 10.9 Hz, 1H), 3.99-4.12 (m, 3H), 4.27 (d, J=16.5 Hz, 1H), 4.36-4.49 (m, 3H), 5.25-5.32 (m, 1H), 5.36 (dq, J=1.4, 17.2 Hz, 1H), 6.01 (ddt, J=6.3, 10.3, 16.9 Hz, 1H).
Intermediate (7j): MS m/z ([M+H]$^+$) 392; $^1$H NMR (400 MHz, CDCl$_3$) δ (ppm): 1.46 (s, 9H), 2.75 (d, J=6.2 Hz, 2H), 3.21 (d, J=10.8 Hz, 1H), 3.71 (dd, J=3.1, 10.9 Hz, 2H), 4.05-4.31 (m, 4H), 4.34-4.49 (m, 4H), 5.26-5.31 (m, 1H), 5.35 (dq, J=1.5, 17.2 Hz, 1H), 5.90-6.12 (m, 1H).

Step 10: Preparation of Intermediate N,N-diethyl-4-hydroxy-2,5-methano-3-oxo-5,7,8,10-tetrahydro-1H-pyrido[3,4]thieno[1,3-d][1,3]diazepine-9-carboxamide (7k)

A solution of intermediate (7i) (0.050 g, 0.1128 mmol) in DCM (4 mL) was degassed 5 min under argon atmosphere.

Acetic acid (0.030 mL, 0.512 mmol) and Pd(PPh₃)₄ (0.1035 g, 0.09 mmol) were successively added. After stirring for 1 h at rt, the mixture was concentrated under nitrogen flux. The residue was purified on silica gel (DCM to DCM/acetone 8/2) to give intermediate (7k) (0.020 g, 0.057 mmol, 45%). MS m/z ([M+H]⁺) 351.

Step 11: Preparation of sodium [9-(diethylcarbamoyl)-2,5-methano-3-oxo-5,7,8,10-tetrahydro-1H-pyrido[3,4]thieno[1,3-d][1,3]diazepin-4-yl] sulfate, Example 7

To a solution of intermediate (7k) (0.020 g, 0.057 mmol) in anhydrous pyridine (2.5 mL) was added sulfur trioxide pyridine complex (0.102 g, 0.64 mmol). After stirring for 18 h, the heterogeneous mixture was concentrated under nitrogen flux. DCM was added and the insoluble was filtered off. The filtrate was concentrated and the residue was applied on a Dowex sodium form column (Dowex® 50WX8 hydrogen form stored with an aqueous solution of 2N NaOH and washed until neutral pH with water). The fractions containing the desired compound were combined, frozen and lyophilized. The solid was purified on C18 reversed-phase chromatography (H2O/MeCN 99/1 up to 90/10). The fractions containing the desired compound were combined, frozen and lyophilized to give Example 7 (0.0043 g, 0.009 mmol, 17%). MS m/z ([M+H]⁺) 431. MS m/z ([M−H]⁻) 429. ¹H NMR (400 MHz, D₂O) δ (ppm): 1.13 (t, J=7.1 Hz, 6H), 2.88-2.95 (m, 2H), 3.28 (q, J=7.1 Hz, 4H), 3.47-3.60 (m, 3H), 3.90 (dd, J=3.1, 11.4 Hz, 1H), 4.10-4.22 (m, 2H), 4.26-4.42 (m, 2H), 4.96 (d, J=2.9 Hz, 1H).

Example 8: Synthesis of (2,5-methano-3-oxo-1,5,7,8,9,10-hexahydropyrido[2,3]thieno[2,4-d][1,3]diazepin-4-yl) hydrogen Sulfate

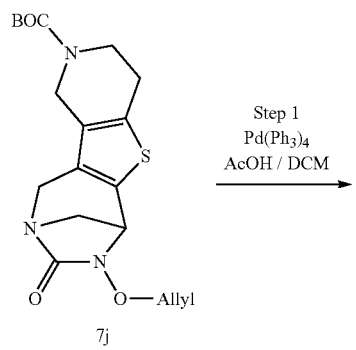

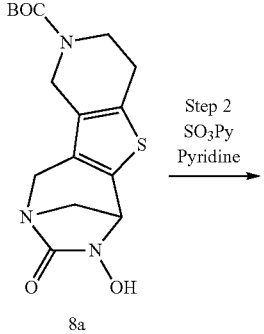

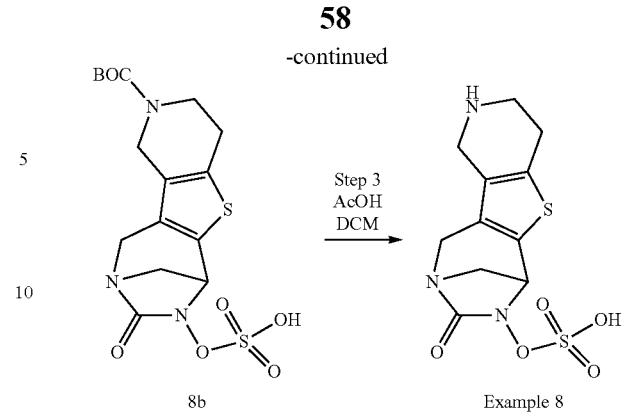

Step 1: Preparation of Intermediate tert-butyl 4-hydroxy-2,5-methano-3-oxo-5,7,8,10-tetrahydro-1H-pyrido[3,4]thieno[1,3-d][1,3]diazepine-9-carboxylate (8a)

A solution of intermediate (7j) (0.040 g, 0.10 mmol) in DCM (4 mL) was degassed 5 min under argon atmosphere. Acetic acid (0.023 mL, 0.40 mmol) and Pd(PPh₃)₄ (0.116 g, 0.10 mmol) were successively added. After stirring for 1 h at rt, the mixture was concentrated under nitrogen flux. The residue was purified on silica gel (DCM to DCM/acetone 8/2) to give intermediate (8a) (0.035 g, 0.01 mmol, 100%). MS m/z ([M+H]⁺) 352.

Step 2: Preparation of Intermediate tert-butyl 2,5-methano-3-oxo-4-sulfooxy-5,7,8,10-tetrahydro-1H-pyrido[3,4]thieno[1,3-d][1,3]diazepine-9-carboxylate (8b)

To a solution of intermediate (8a) (35 mg, 0.01 mmol) in anhydrous pyridine (2.5 mL) was added sulfur trioxide pyridine complex (0.079 g, 0.50 mmol). After stirring for 18 h, the heterogeneous mixture was concentrated under nitrogen flux. DCM was added and the insoluble was filtered off. The filtrate was concentrated. The residue was purified by column chromatography on silica gel (DCM/acetone 8/2 to 2/8) to give intermediate (8b) (18.5 mg, 0.04 mmol, 43%). MS m/z ([M−H]⁻) 430.

Step 3: Preparation of (2,5-methano-3-oxo-1,5,7,8,9,10-hexahydropyrido[2,3]thieno[2,4-d][1,3]diazepin-4-yl) hydrogen sulfate, Example 8

At 0° C., acetic acid (1 mL) was added to a solution of intermediate (8b) in DCM (1 ml. The mixture was stirred at 0° C. for 30 minutes. Heptane (4 mL) was added and mixture was concentrated. The residue was triturated four times with ACN (2 mL). The solid was filtered and dried under vacuum to give Example 8 (0.004 g, 0.015 mmol, 37%). MS m/z ([M+H]⁺) 332. MS m/z ([M−H]⁻) 330. ¹H NMR (400 MHz, D₂O) δ (ppm): 3.16-3.22 (m, 2H), 3.51-3.68 (m, 3H), 3.91 (dd, J=3.2, 11.5 Hz, 1H), 4.13-4.20 (m, 2H), 4.30 (d, J=16.6 Hz, 1H), 4.38 (d, J=16.6 Hz, 1H), 4.99 (d, J=2.9 Hz, 1H).

Example 9: Synthesis of sodium (6,9-methano-4-methyl-7-oxo-5,9-dihydrothiazolo[3,4]pyrrolo[1,3-d][1,3]diazepin-8-yl) sulfate
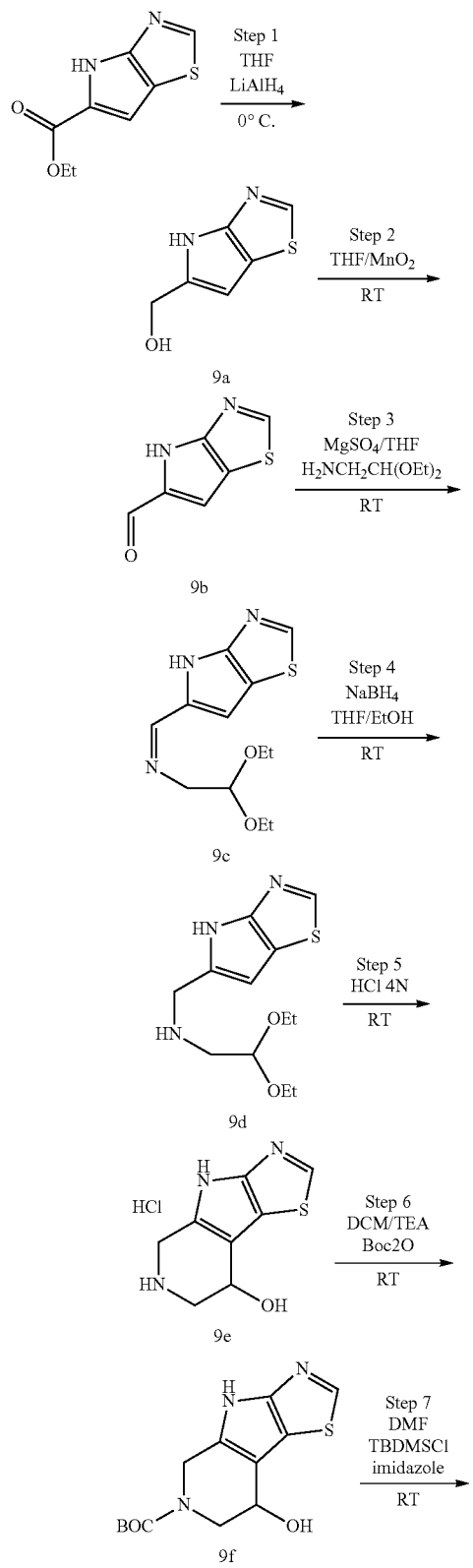
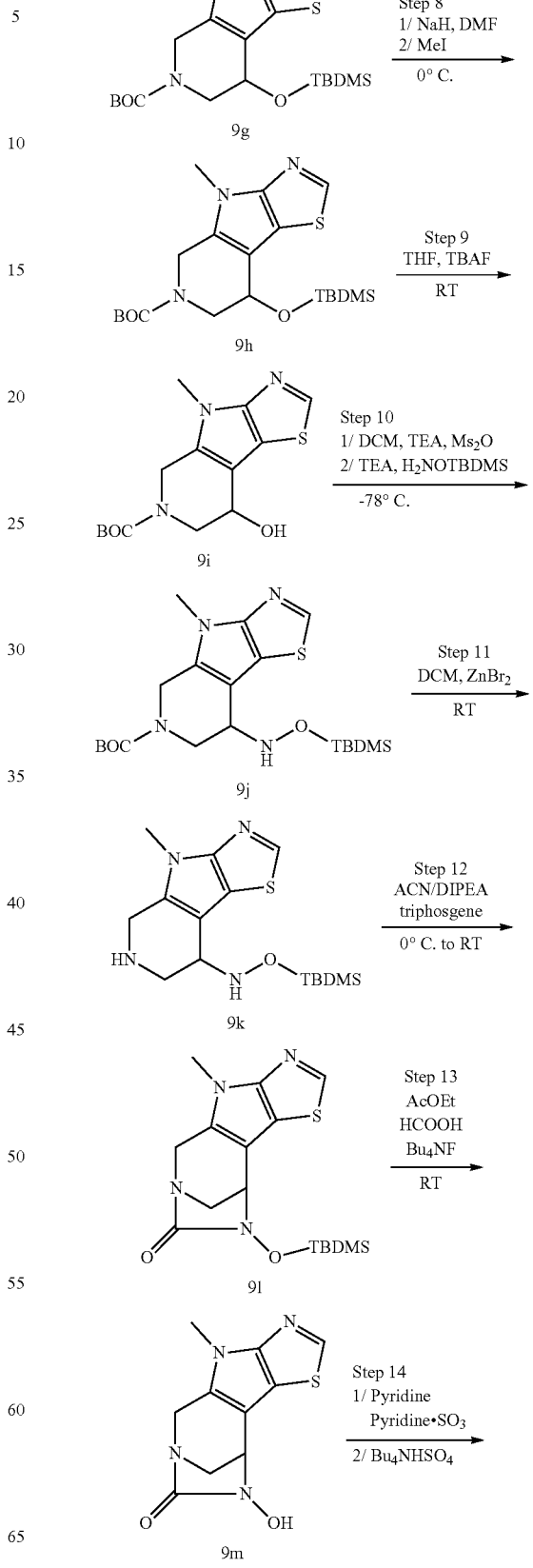

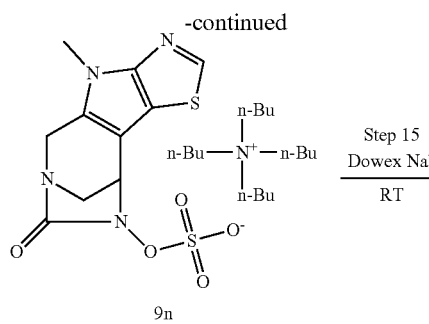

9n

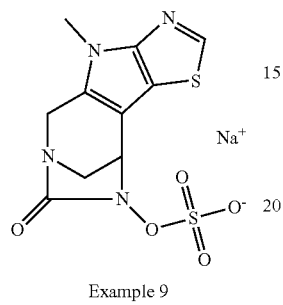

Example 9

Step 1: Preparation of Intermediate 4H-pyrrolo[2,3-d]thiazol-5-ylmethanol (9a)

At 0° C., LiAlH4 (2M in THF, 19.11 mL) was slowly added to a solution of ethyl 4H-pyrrolo[2,3-d][1,3]thiazole-5-carboxylate (5 g, 25.48 mmol) in THF (100 mL). The mixture was stirred at 0° C. for 5 h. The mixture was quenched with NaOH 2N (4.5 mL). The precipitate was filtered off and washed with Et$_2$O. The filtrate was concentrated to give intermediate (9a) which was used without further purification (2.4 g, 15.56 mmol, 61%). MS m/z ([M+H]$^+$) 155. $^1$H NMR (400 MHz, DMSO-d$_6$) δ 4.49 (dd, J=0.6, 5.5 Hz, 2H), 5.08 (t, J=5.5 Hz, 1H), 6.27 (d, J=1.8 Hz, 1H), 8.66 (s, 1H), 11.75 (bs, 1H).

Step 2: Preparation of Intermediate 4H-pyrrolo[2,3-d]thiazole-5-carbaldehyde (9b)

At rt, a solution of intermediate (9a) (2.4 g, 15.56 mmol) and manganese oxide(II) (9.47 g, 108.96 mmol) in THF (100 mL) was stirred for 16 h. The mixture was filtered on a pad of Célite® which was washed with THF. The filtrate was concentrated to give intermediate (9b) which was used without further purification. MS m/z ([M+H]$^+$) 153.

Step 3: Preparation of Intermediate N-(2,2-diethoxyethyl)-1-(4H-pyrrolo[2,3-d]thiazol-5-yl)methanimine (9c)

Intermediate (9b) was solubilized in THF (50 mL) and stirred in presence of aminoacetaldehyde diethyl acetal (3.39 mL, 23.35 mmol) and magnesium sulfate (13.1 g, 108.96 mmol) for 24 h. The mixture was filtered on a pad of Célite®. The filtrate containing intermediate (9c) was directly used without further work-up.

Step 4: Preparation of Intermediate 2,2-diethoxy-N-(4H-pyrrolo[2,3-d]thiazol-5-ylmethyl)ethanamine (9d)

The filtrate of step 3 containing intermediate (9c) was diluted with ethanol (10 mL). Sodium borohydride (883 mg, 23.35 mmol) was slowly added at 0° C. The mixture was stirred for 2 h, then quenched with acetone and water and concentrated. The crude was purified by chromatography on silica gel (DCM/Acetone: 7/3 to 3/7) to give intermediate (9d) (1.05 g, 3.89 mmol, 25%). MS m/z ([M+H]$^+$) 270. $^1$H NMR (400 MHz, CDCl$_3$) δ 1.19-1.23 (m, 6H), 2.78 (d, J=5.3 Hz, 2H), 3.39 (d, J=3.9 Hz, 1H), 3.49-3.74 (m, 4H), 3.95 (s, 2H), 4.59 (d, J=5.3 Hz, 1H), 6.25 (s, 1H), 8.44 (s, 1H), 9.63 (bs, 1H).

Step 5: Preparation of Intermediate 5,6,7,8-tetrahydro-4H-thiazolo[3,4]pyrrolo[1,3-b]pyridin-8-ol hydrochloride salt (9e)

A solution of intermediate (9d) (1.05 g, 3.9 mmol) in HCl 4N (12 mL) was stirred at rt for 3 days. The mixture was then concentrated by co-evaporation with EtOH. The crude containing intermediate (9e) as hydrochloride salt was used in the next step without further purification.

Step 6: Preparation of Intermediate tert-butyl 8-hydroxy-4,5,7,8-tetrahydrothiazolo[3,4]pyrrolo[1,3-b]pyridine-6-carboxylate (9f)

The crude containing intermediate (9e) obtained in step 5 was suspended in DCM (50 mL). TEA (8.8 mL, 63.36 mmol) was added and then Boc$_2$O (851 mg, 3.9 mmol). The mixture was stirred at rt for 10 min. The mixture was washed with NaHCO$_3$ 50% aq, dried over Na$_2$SO$_4$, filtered and concentrated. The crude containing intermediate (9f) was used in the next step without further purification.

Step 7: Preparation of Intermediate tert-butyl 8-[tert-butyl(dimethyl)silyl]oxy-4,5,7,8-tetrahydrothiazolo[3,4]pyrrolo[1,3-b]pyridine-6-carboxylate (9 g)

The crude containing intermediate (9f) obtained in step 6 was suspended in DMF (10 mL). TBDMSCl (705 mg, 4.7 mmol) and imidazole (531 mg, 7.8 mmol) were added and the mixture was stirred for 16 h at rt. The mixture was diluted with AcOEt (60 mL), washed with NaCl 25% (6×10 mL), dried over Na$_2$SO$_4$, filtered and concentrated. The crude was purified by column chromatography on silica gel (eluent: n-heptane/AcOEt 7/3 isochratic) to give intermediate (9 g) (1.1 g, 2.68 mmol, 69% over steps 5 to 7). MS m/z ([M+H]$^+$) 410. $^1$H NMR (400 MHz, CDCl$_3$) δ 0.22 and 0.25 (2s, 6H), 0.97 (s, 9H), 1.51 (s, 9H), 3.29-3.39 (m, 1H), 4.01-4.15 (m, 1H), 4.51 (d, J=16.1 Hz, 1H), 4.68-4.81 (m, 1H), 4.93 (bs, 1H), 8.08 and 8.44 (2s, 1H), 9.07 and 9.40 (2bs, 1H).

Step 8: Preparation of Intermediate tert-butyl 8-[tert-butyl(dimethyl)silyl]oxy-4-methyl-7,8-dihydro-5H-thiazolo[3,4]pyrrolo[1,3-b]pyridine-6-carboxylate (9 h)

At rt, sodium hydride 60% in mineral oil (161 mg, 4.03 mmol) was added to a solution of intermediate (9 g) (1.1 g, 2.69 mmol) in DMF (5 mL). The mixture was stirred for 15 min then methyl iodide (502 μL, 8.06 mmol) was added. The mixture was stirred for 1 h40. The mixture was quenched with aq. NaCl 25% and diluted with AcOEt. The organic layer was washed with aq. NaCl 25% (4×10 mL), dried over Na$_2$SO$_4$, filtered and concentrated. The crude containing intermediate (9 h) was used in the next step without further purification.

Step 9: Preparation of Intermediate tert-butyl 8-hydroxy-4-methyl-7,8-dihydro-5H-thiazolo[3,4]pyrrolo[1,3-b]pyridine-6-carboxylate (9i)

The crude containing intermediate (9h) obtained in step 8 was diluted with THF (5 mL) and a solution of tetrabutylammonium fluoride 1M in THF (3.22 mL, 3.22 mmol) was added. The mixture was stirred for 20 min. The mixture was hydrolyzed with water (50 µL) and concentrated. The crude was purified by column chromatography on silica gel (eluent: n-heptane/AcOEt 5/5 isochratic) to give intermediate (9i) (650 mg, 2.1 mmol, 78% over steps 8 and 9). MS m/z ([M+H]$^+$) 310. $^1$H NMR (400 MHz, DMSO-d$_6$) δ 1.44 (s, 9H), 3.35 (bs, 1H), 3.71 (s, 3H), 3.75-3.79 (m, 1H), 4.48-4.57 (m, 2H), 4.63 (q, J=5.9 Hz, 1H), 5.26 (d, J=6.1 Hz, 1H), 8.70 (s, 1H).

Step 10: Preparation of Intermediate tert-butyl 8-[[tert-butyl(dimethyl)silyl]oxyamino]-4-methyl-7,8-dihydro-5H-thiazolo[3,4]pyrrolo[1,3-b]pyridine-6-carboxylate (9j)

At −78° C., a solution of methanesulfonic anhydride (1.098 g, 6.3 mmol) in DCM (8 mL) was dropped to a solution of intermediate (9i) (650 mg, 2.1 mmol) in DCM (24 mL). The mixture was stirred at −78° C. for 1 h. At −78° C., a solution of O-(tert-Butyldimethylsilyl)hydroxylamine (2.47 g, 16.8 mmol) in DCM (8 mL) was dropped to the mixture which was then warmed to rt for 2 h. The mixture was washed with Na$_2$CO$_3$ 50%, dried over Na$_2$SO$_4$, filtered and concentrated. The crude was purified by column chromatography on silica gel (n-heptane/AcOEt 7/3 isochratic) to give intermediate (9j) (730 mg, 1.66 mmol, 79%). MS m/z ([M+Na]$^+$) 461. $^1$H NMR (400 MHz, CDCl$_3$) δ 0.15 and 0.17 (2, 6H), 0.97 (s, 9H), 1.50 (s, 9H), 3.30-3.44 (m, 1H), 3.75 (s, 3H), 3.96-4.09 (m, 1H), 4.26-4.44 (m, 2H), 4.89-4.94 (m, 1H), 8.42 (s, 1H).

Step 11: Preparation of Intermediate N-[tert-butyl(dimethyl)silyl]oxy-4-methyl-5,6,7,8-tetrahydrothiazolo[3,4]pyrrolo[1,3-b]pyridin-8-amine (9k)

At rt, zinc(II) bromide (1.5 g, 6.65 mmol) was added to a solution of intermediate (9j) (730 mg, 1.66 mmol) in DCM (20 mL). The mixture was stirred at rt for 48 h. The mixture was filtered and the solid was diluted with water. The solution was basified with NaHCO$_3$ and extracted twice with DCM. Organics were dried over Na$_2$SO$_4$, filtered and concentrated. The crude was purified by column chromatography on silica gel (eluent: DCM/MeOH 95/5 isochratic) to give intermediate (9k) (330 mg, 0.97 mmol, 59%). MS m/z ([M+H]$^+$) 339. $^1$H NMR (400 MHz, CDCl$_3$) δ 0.10 and 0.11 (2, 6H), 0.93 (s, 9H), 2.63 (bs, 1H), 2.77 (dd, J=3.2, 13.5 Hz, 1H), 3.15 (d, J=13.5 Hz, 1H), 3.64 (s, 3H), 3.71-3.75 (m, 2H), 3.83 (d, J=16.1 Hz, 1H), 6.09 (d, J=11.4 Hz, 1H), 8.62 (s, 1H).

Step 12: Preparation of Intermediate 8-[tert-butyl(dimethyl)silyl]oxy-6,9-methano-4-methyl-5,9-dihydrothiazolo[3,4]pyrrolo[1,3-d][1,3]diazepin-7-one (9l)

At 0° C., intermediate (9k) (330 mg, 0.975 mmol) and DIPEA (679 µL, 3.9 mmol) were solubilized in ACN (7 mL). A solution of triphosgene (101 mg, 0.341 mmol) in ACN (1 mL) was slowly added at 0° C. and the mixture was then stirred at rt for the night. The mixture was concentrated. The crude was solubilized in DCM and washed with NaHCO$_3$ 25%, dried over Na$_2$SO$_4$, filtered and concentrated. The crude was purified by column chromatography on silica gel (eluent: DCM/acetone 95/5 to 45/55) to give intermediate (9l) (65 mg, 0.178 mmol, 18%). MS m/z ([M+H]$^+$) 365. $^1$H NMR (400 MHz, CDCl$_3$) δ 0.20 (s, 3H), 0.21 (s, 3H), 0.94 (s, 9H), 3.27 (d, J=10.8 Hz, 1H), 3.70 (s, 3H), 3.71 (dd, J=2.9, 10.8 Hz, 1H), 4.35 (d, J=16.1 Hz, 1H), 4.36 (d, J=2.8 Hz, 1H), 4.56 (d, J=16.1 Hz, 1H), 8.38 (s, 1H).

Step 13: Preparation of Intermediate 8-hydroxy-6,9-methano-4-methyl-5,9-dihydrothiazolo[3,4]pyrrolo[1,3-d][1,3]diazepin-7-one (9m)

At rt, a solution of tetrabutylammonium fluoride 1N in THF (123 µL, 0.123 mmol) was added to a solution of intermediate (9l) (45 mg, 0.123 mmol) and formic acid (9 µL, 0.247 mmol) in AcOEt (2 mL). A white precipitate was appeared after 10 min. The precipitate was filtered, washed with AcOEt and dried under vacuum to give intermediate (9m) as white powder (23 mg, 0.091 mmol, 75%). MS m/z ([M+H]$^+$) 251.

Step 14: Preparation of Intermediate n-tetrabutylammonium (6,9-methano-4-methyl-7-oxo-5,9-dihydrothiazolo[3,4]pyrrolo[1,3-d][1,3]diazepin-8-yl) sulfate (9n)

At rt, a suspension of intermediate (9m) (23 mg, 0.091 mmol) and sulfur trioxide pyridine complex (98 mg, 0.617 mmol) in pyridine (5 mL) was stirred for 4 h. The mixture was concentrated. The crude was suspended in DCM and filtered. The solid was washed with DCM and dried under vacuum. The solid was solubilized in water (5 mL) and tetrabutylammonium hydrogensulfate (42 mg, 0.123 mmol) was added for pyridinium/tetrabutylammonium cation exchange. Organics were extracted twice with DCM, dried over Na$_2$SO$_4$, filtered and concentrated to give intermediate (9n) as tetrabutylammonium salt which was used in the next step without further purification.

Step 15: Preparation of sodium (6,9-methano-4-methyl-7-oxo-5,9-dihydrothiazolo[3,4]pyrrolo[1,3-d][1,3]diazepin-8-yl) sulfate, Example 9

Intermediate (9n) obtained in step 14 was applied on a Dowex sodium form column (Dowex® 50WX8 hydrogen form stored with an aqueous solution of 2N NaOH and washed until neutral pH with H$_2$O). Fractions of interest are combined, concentrated under nitrogen flux to remove ACN, frozen and lyophilized to give Example 9 as sodium salt (6 mg, 0.017 mmol, 14%). MS m/z ([M−H]$^−$) 329. $^1$H NMR (400 MHz, DMSO-d$_6$) δ 3.28 (d, J=10.9 Hz, 1H), 3.54 (dd, J=3.0, 10.9 Hz, 1H), 3.66 (s, 3H), 4.37 (d, J=16.3 Hz, 1H), 4.44 (d, J=16.3 Hz, 1H), 4.79 (d, J=3.0 Hz, 1H), 8.70 (s, 1H).

Biological Activity

Method 1: β-Lactamase Inhibitory Activity, Determination of IC$_{50}$ (Table 1)

Enzyme activity was monitored by spectrophotometric measurement of nitrocefin (NCF—TOKU-E, N005) hydrolysis at 485 nm, at room temperature and in assay buffer A: 100 mM Phosphate pH7, 2% glycerol and 0.1 mg/mL Bovine serum albumin (Sigma, B4287). Enzymes were cloned in E. coli expression vector, expressed and purified in house using classical procedures. To a transparent polystyrene plate (Corning, 3628) were added in each well 5 µL DMSO or inhibitor dilutions in DMSO and 80 µL enzyme in buffer A. Plates were immediately read at 485 nm in a microplate spectrophotometer (BioTek, PowerWave HT) to enable background subtraction. After 30 min of pre-incubation at room temperature, 15 µL of NCF (200 µM final) were finally added in each well. Final enzyme concentrations were 0.1 nM (TEM-1), 0.075 nM (SHV-1), 0.4 nM (CTX-M-15), 1 nM (KPC-2), 0.2 nM (P99 AmpC), 0.2 nM (CMY-37), 0.4 nM (AmpC *P. aeruginosa*), 0.2 nM (OXA-1), 1.2 nM (OXA-11), 0.4 nM (OXA-15) and 0.3 nM (OXA-48). After 20 min incubation at room temperature, plates were once again read at 485 nm. Enzyme activity was obtained by subtracting the final signal by the background, and was converted to enzyme inhibition using non inhibited wells. $IC_{50}$ curves were fitted to a classical Langmuir equilibrium model with Hill slope using XLFIT (IDBS).

TABLE 2

Bacterial isolate used in MIC determination

| Strain | | Resistance mechanism |
|---|---|---|
| *E. coli* | ECO 190317 | TEM-1, SHV-12, CTX-M-15, OXA-1 |

TABLE 3

MIC of Ceftazidime (CAZ) and compounds alone (µg/mL)

| Compounds | MIC compounds of the invention alone (µg/mL) ECO 190317 |
|---|---|
| CAZ | 128 |
| 1 | 16 |

TABLE 1

$IC_{50}$ (µM) for β-lactamase Inhibitory Activity

BLA IC50 compounds of the invention (µM)

| | (A) | | | (C) | | | | (D) | | |
|---|---|---|---|---|---|---|---|---|---|---|
| Example | TEM-1 | SHV-1 | CTX-M-15 | KPC-2 | AmpC (P99) | CMY-37 | AmpC (PAE) | OXA-1 | OXA-11 | OXA-15 | OXA-48 |
| 1 | 0.00065 | 0.0041 | 0.0010 | 0.026 | 0.017 | 0.013 | 0.0088 | 0.12 | 0.041 | 3.4 | 0.0011 |
| 2 | 0.00022 | 0.00043 | 0.0026 | 0.00094 | 0.00051 | 0.0012 | 0.0025 | 0.037 | 0.0022 | 0.83 | 0.00066 |
| 3 | 0.0013 | 0.0022 | 0.0025 | 0.0093 | 0.0045 | 0.0094 | 0.062 | 0.19 | 0.031 | 7.1 | 0.0048 |
| 4 | 0.036 | 0.15 | 0.0099 | 0.37 | 0.12 | 0.36 | 2.8 | 4.1 | 0.59 | 13 | 0.0015 |
| 5 | 0.014 | 0.077 | 0.014 | 0.16 | 0.10 | 0.81 | 3.6 | 1.7 | 0.19 | 1.8 | 0.0010 |
| 6 | 0.00020 | 0.00025 | 0.0015 | 0.0042 | 0.0020 | 0.0043 | 0.0036 | 1.3 | 0.16 | 6.5 | 0.0046 |
| 7 | 0.043 | 0.013 | 0.0013 | 0.026 | 0.078 | 0.18 | 0.55 | 5.1 | 0.11 | 14 | 0.0068 |
| 8 | 0.0096 | 0.026 | 0.0061 | 1.3 | 1.6 | 1.8 | 8.6 | 15 | 0.84 | 30 | 0.018 |
| 9 | 0.00049 | 0.00057 | 0.0011 | 0.026 | 0.12 | 0.089 | 0.59 | 0.29 | 0.062 | 0.94 | 0.0012 |

Method 2: MIC of Compounds and Synergy with Ceftazidime Against a Bacterial Isolate (Tables 3 and 4)

Compounds of the present invention were assessed against a genotyped bacterial strain alone or in combination with the β-lactam ceftazidime. In the assays, MICs of said compounds, or of ceftazidime at fixed concentrations of said compounds were determined by the broth microdilution method according to the Clinical Laboratory Standards Institute (CLSI—M7-A7). Briefly, compounds alone according to the invention were prepared in DMSO and spotted (2 µL each) on sterile polystyrene plates (Corning, 3788). Compounds and ceftazidime dilutions were prepared in DMSO and spotted (1 µL each) on sterile polystyrene plates (Corning, 3788). Log phase bacterial suspensions were adjusted to a final density of $5 \times 10^5$ cfu/mL in cation-adjusted Mueller-Hinton broth (Becton-Dickinson) and added to each well (98 µL). Microplates were incubated for 16-20 h at 35° C. in ambient air. The MIC of the compounds was defined as the lowest concentration of said compounds that prevented bacterial growth as read by visual inspection. The MIC of ceftazidime at each compound concentration was defined as the lowest concentration of ceftazidime that prevented bacterial growth as read by visual inspection.

TABLE 3-continued

MIC of Ceftazidime (CAZ) and compounds alone (µg/mL)

| Compounds | MIC compounds of the invention alone (µg/mL) ECO 190317 |
|---|---|
| 2 | >32 |
| 3 | 8 |
| 4 | 8 |
| 5 | 4 |
| 6 | >32 |
| 7 | >32 |
| 8 | 1 |
| 9 | >32 |

TABLE 4

MIC of Ceftazidime (CAZ) alone and CAZ/compound combinations

| Compounds | Combination of CAZ and compounds of the invention at 4 µg/mL: MIC (µg/mL) ECO 190317 |
|---|---|
| CAZ | 128 |
| CAZ + 1 | 1 |
| CAZ + 2 | 4 |
| CAZ + 3 | 32 |
| CAZ + 4 | <=0.125 |

TABLE 4-continued

MIC of Ceftazidime (CAZ) alone
and CAZ/compound combinations

| Compounds | Combination of CAZ and compounds of the invention at 4 μg/mL: MIC (μg/mL) ECO 190317 |
|---|---|
| CAZ + 5 | <0.125 |
| CAZ + 6 | 8 |
| CAZ + 7 | 64 |
| CAZ + 8 | <0.125 |
| CAZ + 9 | 64 |

The invention claimed is:

1. A compound of formula (I)

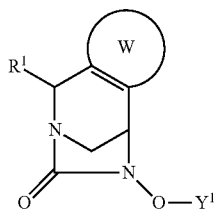

(I)

wherein:
- W represents an 8- to 10-membered aromatic or partially unsaturated bicycle optionally having one or more heteroatoms chosen independently from the group consisting of O, N, N($T^2$), S and/or optionally substituted by one or more $T^1$;
- $R^1$ is chosen from the group consisting of H, $(CH_2)_m CN$, $(CH_2)_m C(=O)NR^2R^3$, $(CH_2)_m C(=O)NR^4NR^2R^3$, $(CH_2)_m C(=O)NR^2OR^3$, $(CH_2)_p OR^2$, $(CH_2)_p NR^2R^3$, $(CH_2)_p NR^4C(=NR^4)N(R^4)_2$, $(CH_2)_m C(=NOZ^4)NZ^1Z^2$ and $(CH_2)_p$-(5 to 6-membered heteroaryl 1 or 4 heteroatoms independently chosen from the group consisting of N, O or S);
- m is an integer from 0 to 6;
- p is an integer from 1 to 6;
- $R^2$ and $R^3$, identical or different, are chosen from the group consisting of H, linear or branched (C1-C6) alkyl, (C3-C11)cycloalkyl, (C6-C10)aryl, 4- to 6-membered heterocyclyl having 1 to 2 heteroatoms chosen independently from the group consisting of N, O or S, 5- to 10-membered heteroaryl having 1 to 4 heteroatoms chosen independently from the group consisting of N, O or S, C(=O) (linear or branched C1-C6)alkyl, C(=O)(4 to 6-membered heterocyclyl having 1 to 2 heteroatoms chosen independently from the group consisting of N, O or S) or form together with the nitrogen atom to which they are linked a 4- to 6-membered heterocyclyl having 1 to 2 heteroatoms chosen independently from the group consisting of N, O or S, wherein alkyl, cycloalkyl, aryl, heterocyclyl and heteroaryl are optionally substituted by one or more $R^5$;
- $R^4$, each identical or different, is independently chosen from the group consisting of H and linear or branched (C1-C6)alkyl, wherein alkyl is optionally substituted by one or more $R^5$;
- $R^5$, each identical or different, is chosen from the group consisting of OH, O-(linear or branched-C1-C6)alkyl, $NH_2$, NH(linear or branched C1-C6) alkyl, N[(linear or branched C1-C6)Alkyl]$_2$, $C(=O)NH_2$, $C(=O)NH$ (linear or branched C1-C6)alkyl and $C(=ON[$linear or branched(C1-C6)alkyl]$_2$;
- $Y^1$ is chosen from the group consisting of $SO_3H$, $CHFC(=O)Y^2$, $CF_2C(=O)Y^2$, and $SO_3(C1-C6)alkyl-C(=O)O(C1-C6)alkyl$;
- $Y^2$ is chosen from the group consisting of OH, O(C1-C6)alkyl, linear or branched, O(C3-C11) cycloalkyl, O-(4 to 6-membered heterocyclyl having 1 or 2 heteroatoms chosen independently from the group consisting of N, O and S), and $NY^3Y^4$, wherein alkyl, cycloalkyl and heterocyclyl are optionally substituted by one or more $Y^5$;
- $Y^3$ and $Y^4$, each identical or different, is chosen from the group consisting of linear or branched (C1-C6)alkyl, linear or branched O(C1-C6)alkyl, (C3-C11)cycloalkyl, 4 to 6-membered heterocyclyl having 1 or 2 heteroatoms chosen independently from the group consisting of N, O or S, or form together with the nitrogen atom to which they are linked a 4- to 6-membered heterocyclyl having 1 or 2 heteroatoms chosen independently from the group consisting of N, O or S, wherein alkyl, cycloalkyl and heterocyclyl is optionally substituted by one or more $Y^5$; and
- $Y^5$, each identical or different, is chosen from the group consisting of linear or branched (C1-C6) alkyl, (C3-C6)cycloalkyl, linear or branched O(C1-C6)alkyl, linear or branched O(C1-C6)alkyl-O(C1-C6)alkyl, linear or branched (C1-C6) alkyl-O(C1-C6)alkyl; and O(C3-C6)cycloalkyl;
- $T^1$ is chosen from the group consisting of halogen, $(CH_2)_m$-CN, $(CH_2)_m$-$OX^1$, $(CH_2)_m$-$C(=O)NX^1X^2$, $(CH_2)_m$-$C(=O)NX^1OX^2$, $(CH_2)_m$-$C(=O)NX^1NX^2X^3$, $(CH_2)_m$-$C(=NOX^1)X^2$, $(CH_2)_m$-$C(=NX^1)NX^2X^3$, $(CH_2)_m$-$NX^1X^2$, $(CH_2)_m$-$NX^1C(=O)X^2$, $(CH_2)_m$-$NX^1C(=O)NX^2X^3$, $(CH_2)_m$-$NX^1S(=O)_2NX^2X^3$, $(CH_2)_m$-$NX^1S(=O)_2X^2$, $(CH_2)_m$-$NX^1C(=NX^2)NHX^3$, $(CH_2)_m$-$NX^1C(=NX^2)X^2$, $(CH_2)_m$-$S(=O)_2NX^1X^2$, linear or branched (C1-C6)alkyl, (C3-C6)cycloalkyl, $(CH_2)_m$-aryl, $(CH_2)_m$-(5- to 6-membered heteroaryl having from 1 to 4 heteroatoms chosen independently from the group consisting of N, O or S), and $(CH_2)_m$-(4- to 6-membered heterocyclyl having from 1 to 2 heteroatoms chosen independently from the group consisting of N, O or S), wherein alkyl, cycloalkyl, aryl, heteroaryl and heterocyclyl are optionally substituted by one or more $X^4$;
- $T^2$ is chosen from the group consisting of H, $(CH_2)_n$-CN, $(CH_2)_n$-$OX^1$, $(CH_2)_m$-$C(=O)X^1$, $(CH_2)_m$-$C(=O)NX^1X^2$, $(CH_2)_m$-$C(=O)NX^1OX^2$, $(CH_2)_m$-$C(=O)NX^1NX^2X^3$, $(CH_2)_m$-$C(=NOX^1)X^2$, $(CH_2)_m$-$C(=NX^1)NX^2X^3$, $(CH_2)_n$-$NX^1X^2$, $(CH_2)_n$-$NX^1C(=O)X^2$, $(CH_2)_n$-$NX^1C(=O)NX^2X^3$, $(CH_2)_n$-$NX^1S(=O)_2NX^2X^3$, $(CH_2)_n$-$NX^1S(=O)_2X^2$, $(CH_2)_n$-$NX^1C(=NX^2)NHX^3$, $(CH_2)_n$-$NX^1C(=NX^2)X^2$, $(CH_2)_m$-$S(=O)_2NX^2X^3$, linear or branched (C1-C6) alkyl, (C3-C6)cycloalkyl, $(CH_2)_m$-aryl, $(CH_2)_m$-(5- to 6-membered heteroaryl having from 1 to 4 heteroatoms chosen independently from the group consisting of N, O or S), and $(CH_2)_m$-(4- to 6-membered heterocyclyl having 1 to 2 heteroatoms chosen independently from the group consisting of N, O or S), wherein alkyl, cycloalkyl, aryl, heteroaryl and heterocyclyl are optionally substituted by one or more $X^4$;

$X^1$, $X^2$ and $X^3$, each identical or different, are chosen from the group consisting of H, linear or branched (C1-C6)alkyl, (C3-C6)cycloalkyl, (C2-C6)alkyl-$NZ^1Z^2$, (C2-C6)alkyl-NHC(=$NZ^1$)$NHZ^2$, (C2-C6)alkyl-NHC(=$NZ^1$)$Z^2$, (C2-C6)alkyl-$NZ^1$C(=O)$Z^2$, (C2-C6)alkyl-$OZ^1$, (C1-C6)alkyl-C(=$NZ^1$)$NHZ^2$, (C1-C6)alkyl-$OZ^1$, (C1-C6)alkyl-$CONZ^1Z^2$, (C1-C6)alkyl-$COOZ^1$, $(CH_2)_m$-aryl, $(CH_2)_m$-(5- to 6-membered heteroaryl having from 1 to 4 heteroatoms chosen independently from the group consisting of N, O and S), and $(CH_2)_m$-(4- to 6-membered heterocyclyl having from 1 to 2 heteroatoms chosen independently from the group consisting of N, O and S), or form together with the nitrogen atom to which they are linked a 4- to 6-membered heterocyclyl having 1 or 2 heteroatoms chosen independently from the group consisting of N, O or S, wherein alkyl, cycloalkyl, aryl, heteroaryl and heterocyclyl are optionally substituted by one or more $Z^3$;

$X^4$, each identical or different, is chosen from the group consisting of H, halogen, linear or branched (C1-C6) alkyl, (C3-C6)cycloalkyl, $(CH_2)_m$-$NZ^1Z^2$, $(CH_2)_m$-NHC(=$NZ^1$)$NHZ^2$, $(CH_2)_m$-NHC(=$NZ^1$)H, $(CH_2)_m$-$NZ^1$C(=O)$Z^2$, $(CH_2)_m$-$OZ^1$, $(CH_2)_m$-C(=$NZ^1$)$NHZ^2$, $(CH_2)_m$-$CONZ^1Z^2$, $(CH_2)_m$-$COOZ^1$, $(CH_2)_m$-aryl, $(CH_2)_m$-(5- to 6-membered heteroaryl having from 1 to 4 heteroatoms chosen independently from the group consisting of N, O and S), and $(CH_2)_m$-(4- to 6-membered heterocyclyl having from 1 to 2 heteroatoms chosen independently from the group consisting of N, O and S), wherein alkyl, cycloalkyl, aryl, heteroaryl and heterocyclyl are optionally substituted by one or more $Z^3$;

$Z^1$ and $Z^2$, identical or different, are chosen from the group consisting of H, linear or branched (C1-C6) alkyl, (C3-C6)cycloalkyl, (C2-C6)alkyl-N($Z^4$)$_2$, (C2-C6)alkyl-$NZ^4$C(=O)$Z^4$, (C2-C6)alkyl-$OZ^4$, (C1-C6)alkyl-C(=NH)$NHZ^4$, (C1-C6)alkyl-CON($Z^4$)$_2$, and (C1-C6)alkyl-$COOZ^4$;

$Z^3$, each identical or different, is chosen from the group consisting of H, halogen, linear or branched (C1-C6) alkyl, (C3-C6)cycloalkyl, $(CH_2)_m$-N($Z^4$)$_2$, $(CH_2)_m$-$OZ^4$C(=O)$Z^4$, $(CH_2)_m$-$OZ^4$, $(CH_2)_m$-CON($Z^4$)$_2$, and $(CH_2)_m$-$COOZ^4$;

$Z^4$, each identical or different, is chosen from the group consisting of H, linear or branched (C1-C6)alkyl, and (C3-C6)cycloalkyl, n is an integer from 2 to 6;

any sulphur atom present within a heterocycle can be oxidized to form a S=O group or a $S(O)_2$ group;

any nitrogen atom present within a heterocycle or present within group wherein it is trisubstituted thus forming a tertiary amino group, can be further quaternized by a methyl group; or a racemate, an enantiomer, a diastereoisomer, or a pharmaceutically acceptable salt thereof.

2. The compound according to claim 1, wherein:

$R^1$ is chosen from the group consisting of H, $(CH_2)_m$CN, $(CH_2)_m$C(=O)$NR^2R^3$, $(CH_2)_m$C(=O)$NR^4NR^2R^3$, $(CH_2)_m$C(=O)$NR^2OR^3$, $(CH_2)_p$$OR^2$, $(CH_2)_p$$NR^2R^3$, $(CH_2)_p$$NR^4$C(=$NR^4$)N($R^4$)$_2$, and $(CH_2)_p$-(5 to 6-membered heteroaryl having 1 or 4 heteroatoms independently chosen from the group consisting of N, O or S); and/or $Y^1$ is chosen from the group consisting of $SO_3H$, $CHFC(=O)Y^2$, and $CF_2C(=O)Y^2$.

3. The compound according to claim 1, wherein the compound is of formula (IA)

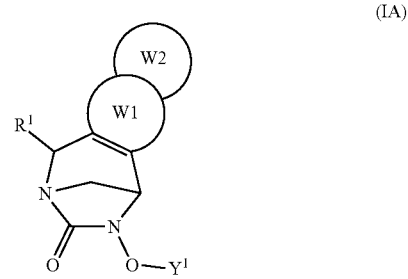

(IA)

wherein:
W1 is a 5- to 6-membered ring, aromatic or partially unsaturated, optionally substituted by one or more $T^1$ and having optionally one or more heteroatoms independently selected from the group consisting of O, N, N($T^2$) and S; and W2 is a 5- to 6-membered ring, aromatic or partially unsaturated, optionally substituted by one or more $T^1$ and having optionally one or more heteroatoms independently selected from the group consisting of O, N, N($T^2$) and S.

4. The compound according to claim 3, wherein:

W1 represents a 5-membered ring, aromatic or partially unsaturated, optionally substituted by one or more $T^1$ and having 1 or 2 heteroatoms independently selected from the group consisting of O, N, N($T^2$), S; and W2 represents a 5- to 6-membered ring, aromatic or partially unsaturated, optionally substituted by one or more $T^1$ and having optionally one or more heteroatoms independently selected from the group consisting of O, N, N($T^2$) and S;

or

W1 represents a 6-membered ring, aromatic or partially unsaturated, optionally substituted by one or more $T^1$ and having optionally 1 or 2 heteroatoms independently selected from the group consisting of O, N, N($T^2$) and S; and W2 represents a 5- to 6-membered ring, aromatic or partially unsaturated, optionally substituted by one or more $T^1$ and having optionally one or more heteroatoms independently selected from the group consisting of O, N, N($T^2$) and S;

or

W1 represents a thiazole, thiophene, pyrrole, pyrrole for which one N atom is substituted by $T^2$ or imidazole, optionally substituted by one or more $T^1$; and W2 represents a 5- to 6-membered ring, aromatic or partially unsaturated, optionally substituted by one or more $T^1$ and having optionally one or more heteroatoms independently selected from the group consisting of O, N, N($T^2$) and S;

or

W1 represents a phenyl, pyridine, pyrazine or thiazine, optionally substituted by one or more $T^1$; and W2 represents a 5- to 6-membered ring, aromatic or partially unsaturated, optionally substituted by one or more $T^1$ and having optionally one or more heteroatoms independently selected from the group consisting of O, N, N($T^2$) and S;

or
- W1 represents a thiazole, thiophene, pyrrole, pyrrole for which one N atom is substituted by $T^2$ or imidazole, optionally substituted by one $T^1$; and
- W2 represents a imidazole, imidazole for which one N atom is substituted by $T^2$, triazole, triazole for which one N atom is substituted by $T^2$, pyrrole, pyrrole for which one N atom is substituted by $T^2$, pyrazole, pyrazole for which one N atom is substituted by $T^2$, dihydropyrrole, dihydropyrrole for which one N atom is substituted by $T^2$, and thiazole optionally substituted by one or more $T^1$;

or
- W1 represents a thiazole, thiophene, pyrrole, pyrrole for which one N atom is substituted by $T^2$ or imidazole, optionally substituted by one $T^1$; and
- W2 represents a phenyl, pyridine, pyridazine, pyrimidine, pyrazine or tetrahydropyridine for which one N atom is substituted by $T^2$, optionally substituted by one $T^1$;

or
- W1 represents a phenyl, pyridine, pyrazine or thiazine, optionally substituted by one or more $T^1$; and
- W2 represents a imidazole, imidazole for which one N atom is substituted by $T^2$, triazole, triazole for which one N atom is substituted by $T^2$, pyrrole, pyrrole for which one N atom is substituted by $T^2$, pyrazole, pyrazole for which one N atom is substituted by $T^2$, dihydropyrrole, dihydropyrrole for which one N atom is substituted by $T^2$, and thiazole optionally substituted by one or more $T^1$;

or
- W1 represents a phenyl, pyridine, pyrazine or thiazine, optionally substituted by one or more $T^1$; and
- W2 represents a phenyl, pyridine, pyridazine, pyrimidine, pyrazine or tetrahydropyridine for which one N atom is substituted by $T^2$, optionally substituted by one $T^1$.

5. The compound according to claim 1, chosen among the following:

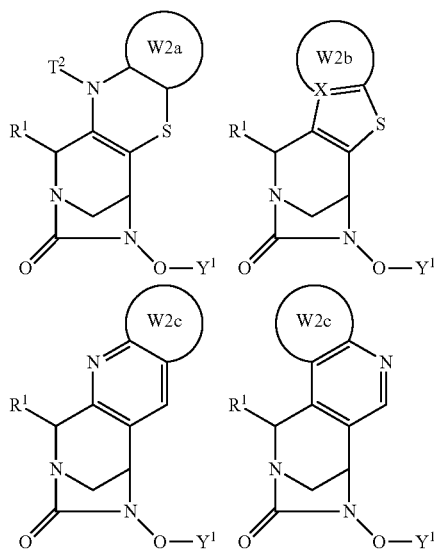

-continued

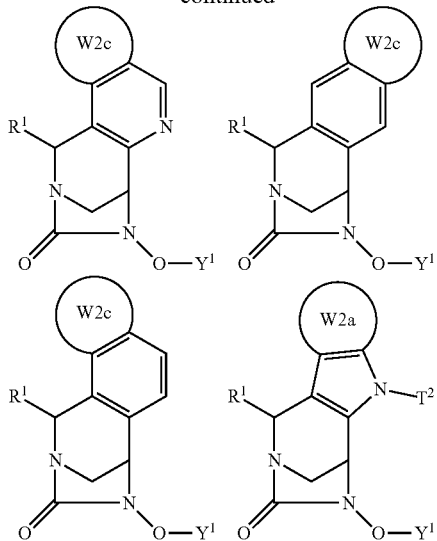

wherein:
- W2a, W2b and W2c are independently chosen among 5- to 6-membered ring, aromatic or partially unsaturated, optionally substituted by one or more $T^1$ and having optionally one or more heteroatoms independently selected from the group consisting of O, N, $N(T^2)$ and S; and
- X is chosen from C or N.

6. The compound according to claim 5, wherein:
- W2a is chosen from the group consisting of phenyl or pyridinyl; and
- W2b and W2c are chosen in from the group consisting of phenyl and 5 to 6-membered heterocycle, aromatic or partially unsaturated, optionally substituted by one or more $T^1$, having 1 to 3 heteroatoms independently chosen from the group consisting of $N(T^2)$, N or S.

7. The compound according to claim 5, chosen among the following:

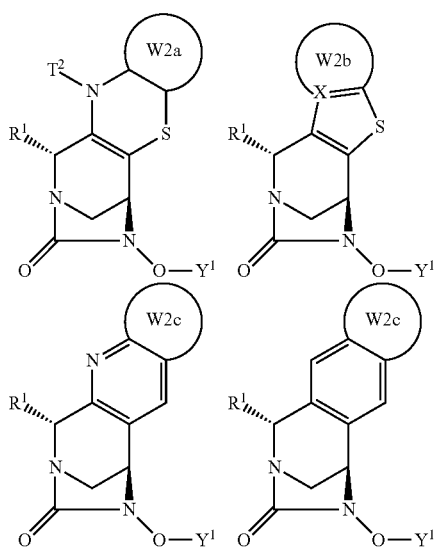

-continued

[chemical structure showing W2a ring system with R¹, T², N, O, Y¹ substituents]

8. The compound according to claim 1, wherein:
R¹ is chosen from the group consisting of H, CN, C(=O)NR²R³, C(=O)NHNHR², C(=O)NHOR², (CH₂)OR², (CH₂)NHR², (CH₂)NR⁴C(=NR⁴)N(R⁴)₂, C(=NOZ⁴)NZ¹Z², and (CH₂)(5- to 6-membered heteroaryl having 1 to 4 heteroatoms independently chosen from the group consisting of N, O or S);
R² and R³, identical or different, are chosen from the group consisting of H, linear or branched (C1-C6)alkyl, (4- to 6-membered heterocyclyl having 1 or 2 heteroatoms independently chosen from the group consisting of N, O or S), and C(=O)(4- to 6-membered heterocyclyl comprising having 1 or 2 heteroatoms independently chosen from the group consisting of N, O or S);
R⁴, each identical or different, is independently chosen from the group consisting of H and linear or branched (C1-C6)alkyl, wherein alkyl is optionally substituted by one or more R⁵;
R⁵, each identical or different, is chosen from the group consisting of OH, O(linear or branched-C1-C6)alkyl, NH₂, NH(linear or branched C1-C6)alkyl, N[(linear or branched C1-C6)Alkyl]₂, C(=O)NH₂, C(=O)NH(linear or branched C1-C6)alkyl, C(=O)N[linear or branched (C1-C6)alkyl]₂;
Y² is chosen in from the group consisting of OH, O(C1-C6)alkyl, linear or branched, O-(4- to 6-membered heterocyclyl having 1 or 2 heteroatoms chosen from the group consisting of N, O and S, wherein alkyl and heterocyclyl are optionally substituted by one or more Y⁵; and
Y⁵, each identical or different, is chosen from the group consisting of linear or branched (C1-C6)alkyl, linear or branched O(C1-C6)alkyl, linear or branched O(C1-C6)alkyl-O(C1-C6)alkyl, linear or branched (C1-C6)alkyl-O(C1-C6)alkyl.

9. The compound according to claim 1, wherein:
R¹ is chosen from the group consisting of H, CN, C(=O)NR²R³, C(=O)NHNHR², C(=O)NHOR², (CH₂)OR², (CH₂)NHR², (CH₂)NR⁴C(=NR⁴)N(R⁴)₂, and (CH₂)(5- to 6-membered heteroaryl having 1 to 4 heteroatoms independently chosen from the group consisting of N, O or S);
R² and R³, identical or different, are chosen from the group consisting of H,
linear or branched (C1-C6)alkyl, (4- to 6-membered heterocyclyl having 1 or 2 heteroatoms independently chosen from the group consisting of N, O or S), and C(=O)(4- to 6-membered heterocyclyl having 1 or 2 heteroatoms independently chosen from the group consisting of N, O or S);
R⁴, each identical or different, is independently chosen from the group consisting of H and linear or branched (C1-C6)alkyl, wherein alkyl is optionally substituted by one or more R⁵;
R⁵, each identical or different, is chosen from the group consisting of OH, O(linear or branched-C1-C6)alkyl, NH₂, NH(linear or branched C1-C6)alkyl, N[(linear or branched C1-C6)Alkyl]₂, C(=O)NH₂, C(=O)NH(linear or branched C1-C6)alkyl, C(=O)N[linear or branched (C1-C6)alkyl]₂;
Y² is chosen in from the group consisting of OH, O(C1-C6)alkyl, linear or branched, O-(4- to 6-membered heterocyclyl having 1 or 2 heteroatoms chosen from the group consisting of N, O and S, wherein alkyl and heterocyclyl are optionally substituted by one or more Y⁵; and
Y⁵, each identical or different, is chosen from the group consisting of linear or branched (C1-C6)alkyl, linear or branched O(C1-C6)alkyl, linear or branched O(C1-C6)alkyl-O(C1-C6)alkyl, linear or branched (C1-C6)alkyl-O(C1-C6)alkyl.

10. A pharmaceutical composition comprising a compound according to claim 1 and a pharmaceutically acceptable excipient.

11. The pharmaceutical composition according to claim 10 further comprising an antibacterial compound.

12. The pharmaceutical composition according to claim 11, wherein the antibacterial compound is selected from aminoglycosides, β-lactams, glycylcyclines, tetracyclines, quinolones, fluoroquinolones, glycopeptides, lipopeptides, macrolides, ketolides, lincosamides, streptogramins, oxazolidinones, polymyxins and mixtures thereof.

13. The pharmaceutical composition according to claim 10 further comprising a β-lactam compound.

14. The pharmaceutical composition according to claim 13, wherein the β-lactam compound is selected from penicillin, cephalosporins, penems, carbapenems, monobactam, and combinations thereof.

15. A pharmaceutical composition comprising at least a compound according to claim 1 and ceftazidime.

16. A kit comprising:
a first pharmaceutical composition that comprises a first pharmaceutically active compound and a first pharmaceutically acceptable excipient; and
a second pharmaceutical composition that comprises a second pharmaceutically active compound and second pharmaceutically acceptable excipient;
wherein the first and second pharmaceutically active compounds are different compounds according to claim 1.

17. A kit comprising:
a first pharmaceutical composition comprising at least a compound according to claim 1; and
a second pharmaceutical composition comprising ceftazidime.

18. A method for treating a bacterial infection caused by bacteria producing one or more β-lactamase, the method comprising the administration to a patient in need thereof an effective amount of a compound according to claim 1.

19. The method according to claim 18, wherein the bacteria is a gram-positive bacteria or gram-negative bacteria.

20. The method according to claim 18, wherein the bacteria is a gram-negative bacteria.

21. A method for treating a bacterial infection, the method comprising the simultaneous, separate or sequential administration to a patient in need thereof an effective amount of the first and second pharmaceutically acceptable active compounds of a kit according to claim 16.

22. The compound according to claim 1, chosen among the following:

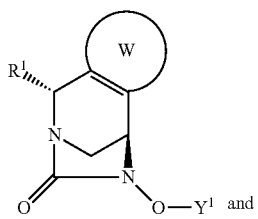
(I*)

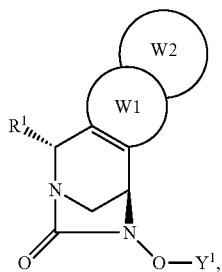
(IA*)

wherein:
W1 is a 5- to 6-membered ring, aromatic or partially unsaturated, optionally substituted by one or more $T^1$ and having optionally one or more heteroatoms independently selected from the group consisting of O, N, $N(T^2)$, and S; and
W2 is a 5- to 6-membered ring, aromatic or partially unsaturated, optionally substituted by one or more $T^1$ and having optionally one or more heteroatoms independently selected from the group consisting of O, N, $N(T^2)$, and S.

* * * * *